(12) United States Patent
Peled et al.

(10) Patent No.: US 9,567,569 B2
(45) Date of Patent: Feb. 14, 2017

(54) METHODS OF CULTURING AND EXPANDING MESENCHYMAL STEM CELLS

(71) Applicant: Gamida Cell Ltd., Jerusalem (IL)

(72) Inventors: Tony Peled, Mevaseret Zion (IL); Yair Steinhardt, Kfar-Saba (IL)

(73) Assignee: Gamida Cell Ltd., Jerusalem (IL)

( * ) Notice: Subject to any disclaimer, the term of this patent is extended or adjusted under 35 U.S.C. 154(b) by 427 days.

(21) Appl. No.: 13/946,272

(22) Filed: Jul. 19, 2013

(65) Prior Publication Data

US 2014/0023623 A1 Jan. 23, 2014

Related U.S. Application Data

(60) Provisional application No. 61/674,428, filed on Jul. 23, 2012.

(51) Int. Cl.
*C12N 5/00* (2006.01)
*C12N 5/0775* (2010.01)
*A61K 35/28* (2015.01)

(52) U.S. Cl.
CPC .......... *C12N 5/0675* (2013.01); *C12N 5/0663* (2013.01); *A61K 35/28* (2013.01); *C12N 2501/38* (2013.01); *C12N 2501/60* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 3,715,345 A | 2/1973 | Smith |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,863,008 A | 1/1975 | Grant |
| 3,867,517 A | 2/1975 | Ling |
| 3,876,623 A | 4/1975 | Jackson et al. |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. |
| 4,666,828 A | 5/1987 | Gusella |
| 4,683,202 A | 7/1987 | Mullis |
| 4,687,808 A | 8/1987 | Jarrett et al. |
| 4,801,531 A | 1/1989 | Frossard |
| 4,806,484 A | 2/1989 | Petrossian et al. |
| 4,816,567 A | 3/1989 | Cabilly et al. |
| 4,866,052 A | 9/1989 | Hider et al. |
| 4,868,116 A | 9/1989 | Morgan et al. |
| 4,879,219 A | 11/1989 | Wands et al. |
| 4,946,778 A | 8/1990 | Ladner et al. |
| 4,980,286 A | 12/1990 | Morgan et al. |
| 5,011,771 A | 4/1991 | Bellet et al. |
| 5,013,830 A | 5/1991 | Ohtsuka et al. |
| 5,023,243 A | 6/1991 | Tullis |
| 5,034,506 A | 7/1991 | Summerton et al. |
| 5,081,035 A | 1/1992 | Halberstadt et al. |
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,278,302 A | 1/1994 | Caruthers et al. |

(Continued)

FOREIGN PATENT DOCUMENTS

| | | |
|---|---|---|
| AU | 759522 B2 | 4/2003 |
| AU | 770896 B2 | 3/2004 |

(Continued)

OTHER PUBLICATIONS

Bachanova et al. "Allogeneic Natural Killer Cells for Refractory Lymphoma." *Cancer Immunol. Immunother.* 59(2010):1739-1744.
Beider et al. "Involvement of CXCR4 and IL-2 in the Homing and Retention of Human NK and NK T Cells to the Bone Marrow and Spleen of NOD/SCID Mice." *Blood.* 102.6(2003):1951-1958.
Berg et al. "Clinical-Grade ex vivo—Expanded Human Natural Killer Cells Up-Regulate Activating Receptors and Death Receptor Ligands and Have Enhanced Cytolytic Activity Against Tumor Cells." *Cythotherapy.* 11.3(2009):341-355.
Bernardini et al. "CCL3 and CXCL12 Regulate Trafficking of Mouse Bone Marrow NK Cell Subsets." *Blood.* 111.7(2008):3626-3634.
Caligiuri. "Human Natural Killer Cells." *Blood.* 112.3(2008):461-469.
Cho et al. "Expansion and Activation of Natural Killer Cells for Cancer Immunotherapy." *Korean J. Lab. Med.* 29.2(2009):89-96.

(Continued)

*Primary Examiner* — Blaine Lankford
(74) *Attorney, Agent, or Firm* — Ivor R. Elrifi; Matthew Pavao Cooley LLP

(57) ABSTRACT

A method of culturing mesenchymal stem cells (MSCs) is provided. The method comprising culturing a population of the MSCs in a medium comprising an aryl hydrocarbon receptor antagonist, thereby culturing MSCs.

19 Claims, 5 Drawing Sheets

(56) References Cited

U.S. PATENT DOCUMENTS

| | | |
|---|---|---|
| 5,281,521 A | 1/1994 | Trojanowski et al. |
| 5,286,717 A | 2/1994 | Cohen et al. |
| 5,320,963 A | 6/1994 | Knaack et al. |
| 5,321,131 A | 6/1994 | Agrawal et al. |
| 5,342,781 A | 8/1994 | Su |
| 5,366,878 A | 11/1994 | Pederson et al. |
| 5,378,725 A | 1/1995 | Bonjouklian et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,437,994 A | 8/1995 | Emerson et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,480,906 A | 1/1996 | Creemer et al. |
| 5,486,359 A | 1/1996 | Caplan et al. |
| 5,489,677 A | 2/1996 | Sanghvi et al. |
| 5,491,133 A | 2/1996 | Walder et al. |
| 5,504,103 A | 4/1996 | Bonjouklian et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,612,211 A | 3/1997 | Wilson et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,625,126 A | 4/1997 | Lonberg et al. |
| 5,631,219 A | 5/1997 | Rosenthal et al. |
| 5,633,360 A | 5/1997 | Bischofberger et al. |
| 5,633,425 A | 5/1997 | Lonberg et al. |
| 5,652,355 A | 7/1997 | Metelev et al. |
| 5,652,356 A | 7/1997 | Agrawal |
| 5,654,186 A | 8/1997 | Cerami et al. |
| 5,661,016 A | 8/1997 | Lonberg et al. |
| 5,663,312 A | 9/1997 | Chaturvedula |
| 5,674,750 A | 10/1997 | Kraus et al. |
| 5,677,437 A | 10/1997 | Teng et al. |
| 5,677,439 A | 10/1997 | Weis et al. |
| 5,700,922 A | 12/1997 | Cook |
| 5,712,154 A | 1/1998 | Mullon et al. |
| 5,714,331 A | 2/1998 | Buchardt et al. |
| 5,716,411 A | 2/1998 | Orgill et al. |
| 5,716,616 A | 2/1998 | Prockop et al. |
| 5,719,262 A | 2/1998 | Buchardt et al. |
| 5,733,541 A | 3/1998 | Taichman et al. |
| 5,736,396 A | 4/1998 | Bruder et al. |
| 5,741,899 A | 4/1998 | Capon et al. |
| 5,770,378 A | 6/1998 | Hwang et al. |
| 5,770,580 A | 6/1998 | Ledley et al. |
| 5,776,699 A | 7/1998 | Klein et al. |
| 5,789,245 A | 8/1998 | Dubensky, Jr. et al. |
| 5,789,543 A | 8/1998 | Ingham et al. |
| 5,792,751 A | 8/1998 | Ledley et al. |
| 5,814,482 A | 9/1998 | Dubensky, Jr. et al. |
| 5,830,760 A | 11/1998 | Tsai et al. |
| 5,837,544 A | 11/1998 | Capon et al. |
| 5,843,723 A | 12/1998 | Dubensky, Jr. et al. |
| 5,844,079 A | 12/1998 | Ingham et al. |
| 5,851,832 A | 12/1998 | Weiss et al. |
| 5,851,984 A | 12/1998 | Matthews et al. |
| 5,877,207 A | 3/1999 | Klein et al. |
| 5,945,309 A | 8/1999 | Ni et al. |
| 5,945,337 A | 8/1999 | Brown |
| 5,952,345 A | 9/1999 | Klein et al. |
| 5,958,954 A | 9/1999 | Klein et al. |
| 5,990,329 A | 11/1999 | Klaus et al. |
| 6,008,204 A | 12/1999 | Klein et al. |
| 6,015,686 A | 1/2000 | Dubensky, Jr. et al. |
| 6,015,694 A | 1/2000 | Dubensky, Jr. et al. |
| 6,063,797 A | 5/2000 | Fesus et al. |
| 6,077,947 A | 6/2000 | Capon et al. |
| 6,090,810 A | 7/2000 | Klein et al. |
| 6,130,230 A | 10/2000 | Chambon et al. |
| 6,133,309 A | 10/2000 | Bollag et al. |
| 6,165,747 A | 12/2000 | Ingham et al. |
| 6,177,850 B1 | 1/2001 | Furutani et al. |
| 6,218,128 B1 | 4/2001 | Klein et al. |
| 6,228,848 B1 | 5/2001 | Klein et al. |
| 6,232,291 B1 | 5/2001 | Ni et al. |
| 6,248,587 B1 * | 6/2001 | Rodgers ............... A61K 38/085 435/375 |
| 6,255,112 B1 | 7/2001 | Thiede et al. |
| 6,261,786 B1 | 7/2001 | Marigo et al. |
| 6,270,964 B1 | 8/2001 | Michnick et al. |
| 6,271,363 B1 | 8/2001 | Ingham et al. |
| 6,284,540 B1 | 9/2001 | Milbrandt et al. |
| 6,294,330 B1 | 9/2001 | Michnick et al. |
| 6,303,374 B1 | 10/2001 | Zhang et al. |
| 6,306,575 B1 | 10/2001 | Thomas et al. |
| 6,326,174 B1 | 12/2001 | Joyce et al. |
| 6,326,198 B1 | 12/2001 | Emerson et al. |
| 6,329,169 B1 | 12/2001 | Ni et al. |
| 6,335,195 B1 * | 1/2002 | Rodgers ............... A61K 38/085 435/377 |
| 6,338,942 B2 | 1/2002 | Kraus et al. |
| 6,342,219 B1 | 1/2002 | Thorpe et al. |
| 6,342,221 B1 | 1/2002 | Thorpe et al. |
| 6,342,372 B1 | 1/2002 | Dubensky, Jr. et al. |
| 6,342,581 B1 | 1/2002 | Rosen et al. |
| 6,372,210 B2 | 4/2002 | Brown |
| 6,372,473 B1 | 4/2002 | Moore et al. |
| 6,376,236 B1 | 4/2002 | Dubensky, Jr. et al. |
| 6,384,192 B1 | 5/2002 | Ingham et al. |
| 6,413,772 B1 | 7/2002 | Block |
| 6,413,773 B1 | 7/2002 | Ptasznik et al. |
| 6,642,019 B1 | 11/2003 | Anderson et al. |
| 6,645,489 B2 | 11/2003 | Pykett et al. |
| 6,680,166 B1 | 1/2004 | Mullon et al. |
| 6,887,704 B2 | 5/2005 | Peled et al. |
| 6,962,698 B1 | 11/2005 | Peled et al. |
| 7,169,605 B2 | 1/2007 | Peled et al. |
| 7,247,477 B2 | 7/2007 | Itskovitz-Eldor et al. |
| 7,344,881 B2 | 3/2008 | Peled et al. |
| 7,955,852 B2 | 6/2011 | Peled et al. |
| 8,080,417 B2 | 12/2011 | Peled et al. |
| 8,652,841 B2 * | 2/2014 | Ochiai ............... C12M 21/08 435/325 |
| 2001/0014475 A1 | 8/2001 | Frondoza et al. |
| 2002/0001826 A1 | 1/2002 | Wager et al. |
| 2002/0090603 A1 | 7/2002 | Lipton et al. |
| 2002/0114784 A1 | 8/2002 | Li et al. |
| 2002/0114789 A1 | 8/2002 | Peled et al. |
| 2002/0146678 A1 | 10/2002 | Benvenisty |
| 2002/0146816 A1 | 10/2002 | Vellinger et al. |
| 2002/0159981 A1 | 10/2002 | Peled et al. |
| 2002/0159984 A1 | 10/2002 | Brown |
| 2002/0182728 A1 | 12/2002 | Ramiya et al. |
| 2003/0002363 A1 | 1/2003 | Le et al. |
| 2003/0031665 A1 | 2/2003 | Dang et al. |
| 2003/0113913 A1 | 6/2003 | Purton et al. |
| 2003/0125410 A1 | 7/2003 | Keita et al. |
| 2003/0149074 A1 | 8/2003 | Melese et al. |
| 2003/0215445 A1 | 11/2003 | Serrero |
| 2003/0235563 A1 | 12/2003 | Strom et al. |

(56) References Cited

U.S. PATENT DOCUMENTS

| | | |
|---|---|---|
| 2003/0235909 A1 | 12/2003 | Hariri et al. |
| 2004/0076603 A1 | 4/2004 | Peled et al. |
| 2004/0247574 A1 | 12/2004 | Christopherson et al. |
| 2005/0008624 A1 | 1/2005 | Peled et al. |
| 2005/0031595 A1 | 2/2005 | Peled et al. |
| 2005/0054097 A1 | 3/2005 | Peled et al. |
| 2005/0054103 A1 | 3/2005 | Peled et al. |
| 2005/0069527 A1 | 3/2005 | Laughlin et al. |
| 2005/0084961 A1 | 4/2005 | Hedrick et al. |
| 2005/0095228 A1 | 5/2005 | Fraser et al. |
| 2005/0118150 A1 | 6/2005 | Peled et al. |
| 2005/0214262 A1 | 9/2005 | Peled et al. |
| 2005/0220774 A1 | 10/2005 | Peled et al. |
| 2005/0260748 A1 | 11/2005 | Chang et al. |
| 2006/0093605 A1 | 5/2006 | Campana et al. |
| 2006/0171932 A1 | 8/2006 | Hendricks et al. |
| 2006/0205071 A1 | 9/2006 | Hasson et al. |
| 2007/0077652 A1 | 4/2007 | Peled et al. |
| 2008/0279828 A1 | 11/2008 | Peled et al. |
| 2009/0257987 A1 | 10/2009 | Offen et al. |
| 2010/0015103 A1 | 1/2010 | Liu et al. |
| 2010/0021434 A1 | 1/2010 | Melamed et al. |
| 2010/0061963 A1 | 3/2010 | Peled |
| 2010/0183564 A1* | 7/2010 | Boitano ............... C07D 473/34 424/93.7 |
| 2012/0028354 A1 | 2/2012 | Lee et al. |
| 2014/0023626 A1 | 1/2014 | Peled et al. |
| 2015/0064273 A1 | 3/2015 | Peled et al. |

FOREIGN PATENT DOCUMENTS

| | | |
|---|---|---|
| EP | 0 331 464 A2 | 9/1989 |
| EP | 1 332 673 A1 | 8/2003 |
| EP | 1 332 676 A1 | 8/2003 |
| EP | 1424389 A1 | 6/2004 |
| JP | 2005528088 A | 9/2005 |
| KR | 20090065814 A | 6/2009 |
| WO | WO-8902468 A1 | 3/1989 |
| WO | WO-8905345 A1 | 6/1989 |
| WO | WO-8907136 A2 | 8/1989 |
| WO | WO-9207573 A1 | 5/1992 |
| WO | WO-9211355 A1 | 7/1992 |
| WO | WO-9309220 A1 | 5/1993 |
| WO | WO-9318132 A1 | 9/1993 |
| WO | WO-9418991 A1 | 9/1994 |
| WO | WO-9514078 A1 | 5/1995 |
| WO | WO-9521911 A1 | 8/1995 |
| WO | WO-9524464 A1 | 9/1995 |
| WO | WO-9601108 A1 | 1/1996 |
| WO | WO-9640876 A1 | 12/1996 |
| WO | WO-9704707 A1 | 2/1997 |
| WO | WO-9731647 A1 | 9/1997 |
| WO | WO-9733978 A1 | 9/1997 |
| WO | WO-9741209 A1 | 11/1997 |
| WO | WO-9741224 A1 | 11/1997 |
| WO | WO-9825634 A1 | 6/1998 |
| WO | WO-9907831 A1 | 2/1999 |
| WO | WO-9918885 A1 | 4/1999 |
| WO | WO-9940783 A1 | 8/1999 |
| WO | WO-9964566 A2 | 12/1999 |
| WO | WO-0018885 A1 | 4/2000 |
| WO | WO-0030635 A1 | 6/2000 |
| WO | WO-0046349 A1 | 8/2000 |
| WO | WO-0066712 A2 | 11/2000 |
| WO | WO-0073421 A2 | 12/2000 |
| WO | WO-02064755 A2 | 8/2002 |
| WO | WO-02080995 A1 | 10/2002 |
| WO | WO-02102299 A2 | 12/2002 |
| WO | WO-03004626 A1 | 1/2003 |
| WO | WO-03051419 A1 | 6/2003 |
| WO | WO-03062369 A2 | 7/2003 |
| WO | WO-03062404 A1 | 7/2003 |
| WO | WO-03072557 A1 | 9/2003 |
| WO | WO-03078567 A2 | 9/2003 |
| WO | WO-2004016731 A2 | 2/2004 |
| WO | WO-2004078917 A2 | 9/2004 |
| WO | WO-2005007073 A2 | 1/2005 |
| WO | WO-2005007799 A2 | 1/2005 |
| WO | WO-2005086845 A2 | 9/2005 |
| WO | WO-2006030442 A2 | 3/2006 |
| WO | WO-2006050270 A2 | 5/2006 |
| WO | WO-2007063545 A2 | 6/2007 |
| WO | WO-2008020815 A1 | 2/2008 |
| WO | WO-2008056368 A2 | 5/2008 |
| WO | WO-2011080740 A1 | 7/2011 |
| WO | WO-2011039357 A1 | 11/2011 |
| WO | WO-2013121426 A1 | 8/2013 |
| WO | WO-2013121427 A1 | 8/2013 |

OTHER PUBLICATIONS

Decot et al. "Natural-Killer Cell Amplification for Adoptive Leukemia Relapse Immunotherapy: Comparison of Three Cytokines, IL-2, IL-15, or IL-7 and Impact on NKG2D, KIR2DL1, and KIR2DL2 Expression." *Exp. Hematol.* 38.5(2010):351-362.

Frias et al. "Generation of Functional Natural Killer and Dendritic Cells in a Human Stromal-Based Serum-Free Culture System Designed for Cord Blood Expansion." *Exp. Hematol.* 36(2008):61-68.

Harada et al. "A Wilms Tumor Cell Line, HFWT, Can Greatly Stimulate Proliferation of CD56+ Human Natural Killer Cells and Their Novel Precursors in Blood Mononuclear Cells." *Exp. Hematol.* 32(2004):614-621.

Humeau et al. "Successful Reconstitution of Human Hematopoiesis in the SCID-hu Mouse by Genetically Modified, Highly Enriched Progenitors Isolated from Fetal Liver." *Blood.* 90.9(1997):3496-3506.

Klingemann et al. "Ex vivo Expansion of Natural Killer Cells for Clinical Applications." *Cythotherapy.* 6.1(2004):15-22.

Koehl et al. "Ex vivo Expansion of Highly Purified NK Cells for Immunotherapy After Haploidentical Stem Cell Transplantation in Children." *Klin. Pädiatr.* 217(2005):345-350.

Markel et al. "Natural Killer Lysis Receptor (NKLR)/NKLR-Ligand Matching as a Novel Approach for Enhancing Anti-Tumor Activity of Allogeneic NK Cells." *PLoS ONE.* 4.5(2009):e5597.

Meyer-Monard et al. "Clinical-Grade Purification of Natural Killer Cells in Haploidentical Hematopoietic Stem Cell Transplantation." *Transfusion.* 49(2009):362-371.

Miller et al. "Role of Monocytes in the Expansion of Human Activated Natural Killer Cells." *Blood.* 80.9(1992):2221-2229.

Robertson et al. "Biology and Clinical Relevance of Human Natural Killer Cells." *Blood.* 76.12(1990):2421-2438.

Rosenberg. "Lymphokine-Activated Killer Cells: A New Approach to Immunotherapy of Cancer." *J. Natl. Cancer Inst.* 75.4(1985):595-603.

Schleinitz et al. "Natural Killer Cells in Human Autoimmune Diseases." *Immunology.* 131(2010):451-458.

Von Drygalski et al. "Murine Bone Marrow Cells Cultured Ex Vivo in the Presence of Multiple Cytokine Combinations Lose Radioprotective and Long-Term Engraftment Potential." *Stem Cells Dev.* 13(2004):101-111.

Yu et al. "CD94 Surface Density Identifies a Functional Intermediary Between the CD56bright and CD56dim Human NK-Cell Subsets." *Blood.* 115.2(2010):274-281.

Zucchini et al. "Natural Killer Cells in Immunodefense Against Infective Agents." *Exp. Rev. Anti Infect. Ther.* 6.6(2008):867-885.

"13th Annual Meeting on Surgical Research." *Langenbeck's Archives of Surgery.* 394.5(2009):915-970.

Search Report and Written Opinion Dated Apr. 8, 2015 From the Intellectual Property Office of Singapore Re. Application No. 11201404608W.

Da Silva Meirelles et al. "Mechanisms Involved in the Therapeutic Properties of Mesenchymal Stem Cells", Cytokine & Growth Factor Reviews, 20: 419-427,2009.

Daan Van Poll et al. "Mesenchymal Stem Cell-Derived Molecules Directly Modulate Hepatocellular Death and Regeneration In Vitro and In Vivo", Hepatology, Vo. 47, No. 5, 2008.

(56) References Cited

OTHER PUBLICATIONS

Boland et al. "Wnt 3a Promotes Proliferation and Suppresses Osteogenic Differentiation of Adult Human Mesenchymal Stem Cells", Journal of Cellular Biochemistry, 93: 1210-1230, 2004.
Bonewald et al. "Role of Active and Latent Transforming Growth Factor Beta in Bone Formation", Journal of Cellular Biochemistry, 55: 350-357, 1994.
Cargnoni et al. "Conditioned Medium From Amniotic Mesenchymal Tissue Cells Reduces Progression of Bleomycin-Induced Lung Fibrosis", Cytotherapy, 14: 153-161, 2012.
Colleoni et al. "Isolation, Growth and Differentiation of Equine Mesenchymal Stem Cells: Effect of Donor, Source, Amount of Tissue and Supplementation With Basi Fibroblast Growth Factor", Veterinary Research Communications, 33(8): 811-821, Dec. 2009.
Furge et al. "Met Receptor Tyrosine Kinase: Enhanced Signaling Through Adapter Proteins", Oncogene, 19: 5582-5589, 2000.
Gnecchi et al. "Bone Marrow-Derived Mesenchymal Stem Cells: Isolation, Expansion, Characterization, Viral Transduction, and Production of Conditioned Medium", Stem Cells in Regenerative Medicine: Methods and Protocols, 482(Chap.18): 281-294, 2009.
Kassis et al. "Isolation of Mesenchymal Stem Cells From G-CSF-Mobilized Human Peripheral Blood Using Fibrin Microbeads", Bone Marrow Transplantation, 37(10): 967-976, May 2006.
Krampera et al. "HB-EGF/HER-1 Signaling in Bone Marrow Mesenchymal Stem Cells: Inducing Cell Expansion and Reversibly Preventing Multilineage Differentiation", Blood, 106(1): 59-66, Jul. 1, 2005.
Lin et al. "The Isolation of Novel Mesenchymal Stromal Cell Chemotactic Factors From the Conditioned Medium of Tumor Cells", Experimental Cell Research, 314: 3107-3117, Available Online Aug. 8, 2008.
Longobardi et al. "Effect of IGF-I in the Chondrogenesis of Bone Marrow Mesenchymal Stem Cells in the Presence of Absence of TGF-Beta Signaling", Journal of Bone and Mineral Research, 21(4): 626-636, Published Online Dec. 26, 2005.
Pons et al. "VEGF Improves Survival of Mesenchymal Stem Cells in Infarcted Hearts", Biochemical and Biophysical Research Communications, 376: 419-422, Available Online Sep. 18, 2008.
Stewart et al. "BMP-3 Promotes Mesenchymal Stem Cell Proliferation Through the TGF-Beta/Activin Signaling Pathway", Journal of Cellular Physiology, 223: 658-666, Feb. 8, 2010.
Tamama et al. "Epidermal Growth Factor (EGF) Treatment on Multipotential Stromal Cells (MSCs). Possible Enhancement of Therapeutic Potential of MSC", Journal of Biomedicine and Biotechnology, 2010(795385): 1-10, 2010.
Tamama et al. "Epidermal Growth Factor as a Candidate for Ex Vivo Expansion of Bone Marrow-Derived Mesenchymal Stem Cells", Stem Cells, 24: 686-695, First Published Sep. 8, 2005.
Van Koppen et al. "Human Embryonic Mesenchymal Stem Cell-Derived Conditioned Medium Rescues Kidney Function in Rats With Established Chronic Kidney Disease", PLoS ONE, 7(6): e38746-1-e38746-12, Jun. 19, 2012.
Wagner et al. "Replicative Senescence of Mesenchymal Stem Cells: A Continuous and Organized Process", PLoS ONE, 3(5): e2213-1-e2213-12, May 21, 2008.
Wang et al. "Clinical Applications of Mesenchymal Stem Cells", Journal of Hematology & Oncology, 5(19): 1-9, 2012.
Wang et al. "Mesenchymal Stem Cell-Conditioned Medium Facilitates Angiogenesis and Fracture Healing in Diabetic Rats", Journal of Tissue Engineering and Regenerative Medicine, 6: 559-569, Published Online Sep. 13, 2011.
Yew et al. "Enhancement of Wound Healing by Human Multipotent Stromal Cell Conditioned Medium: The Paracrine Factors and P38 MAPK Activation", Cell Transplantation, 20: 693-706, Published Online Dec. 22, 2010.
Zhang et al. "Comparison of Mesenchymal Stem Cells From Human Placenta and Bone Marrow", Chinese Medical Journal, 117(6): 882-887, 2004.

"Chelation Therapy." American Cancer Society. Jun. 1, 2005. Web. Sep. 26, 2006. www.cancer.org/docroot/ETO/content/ETO_5_3X_Chelation_Therapy.asp?sitearea=ETO.
"Duraguard 100 (Part B-Hardener)." ChemMasters Material Data Sheet. (1999).
American Cyanamid Co Lederle Laboratories DIV. "6505-01-047-3872: Thiotepa Product Indentification Sheet." (1990).
Acsadi et al. "Human Dystrophin Expression in MDX Mouse after Intramuscular Injection of DNA Constructs." Nature. 352. 6338(1991):815-818.
Aiuti et al. "The Chemokine SDF-1 is a Chemoattractant for Human CD34+ Hematopoietic Progenitor Cells and Provides a New Mechanism to Explain the Mobilization of CD34+ Progenitors to Peripheral Blood." J. Exp. Med. 185.1(1997):111-120.
Alici et al. "Autologous Antitumor Activity by NK Cells Expanded from Myeloma Patients Using GMP-Compliant Components." Blood. 111.6(2008):3155-3162.
Alter. "Fetal Erythropoiesis in Stress Hematopoiesis." Exp. Hematol. 7.55(1979):200-209.
Anderlini et al. "The Use of Mobilized Peripheral Blood Stem Cells from Normal Donors for Allografting." Stem Cells. 15(1997):9-17.
Aoki et al. "In Vivo Transfer Effciency of Antisense Oligonucleotides into the Myocardium Using HVJ-Liposome Method." Biochem. Biophys. Res. Commun. 231(1997):540-545.
Armentano et al. "Expression of Human Factor IX in Rabbit Hepatocytes by Retrovirus-Mediated Gene Transfer: Potential for Gene Therapy of Hemophilia B." PNAS. 87(1990):6141-6145.
Arriero et al. "Adult Skeletal Muscle Stem Cells Differentiate into Endothelial Lineage and Ameliorate Renal Dysfunction after Acute Ischemia." Am. J. Physiol. 287(2004):F621-F627.
Asahara et al. "Stem Cell Therapy and Gene Transfer for Regneration." Gene Ther. 7(2000):451-457.
Auger et al. "PDGF-Dependent Tyrosine Phosphorylation Stimulates Production of Novel Polyphosphoinositides in Intact Cells." Cell. 57(1989):167-175.
Avital et al. "Isolation, Characterization, and Transplantation of Bone Marrow-Derived Hepatocyte Stem Cells." Biochem. Biophys. Res. Commun. 288.1(2001):156-164.
Bae et al. "Copper Uptake and Intracellular Distribution During Retinoic Acid-Induced Differentiation of HL-60 Cells." J. Nutr. Biochem. 5(1994):457-461.
Bae et al. "Retinoic Acid-induced HL-60 Cell Differentiation is Augmented by Copper Supplementation." J. Nutr. 123. 6(1993):997-1002.
Baggiolini. "Chemokines and Leukocyte Traffic." Nature. 392(1998):565-568.
Banasik et al. "Specific Inhibitors of Poly(ADP-Ribose) Synthetase and Mono(ADP-Ribosyl)transferase." J. Biol. Chem. 267. 3(1992):1569-1575.
Banno et al. "Anemia and Neutropenia in Elderly Patients Caused by Copper Deficiency for Long-Term Eternal Nutrition." Jap. J. Clin. Hematol. 35(1994):1276-1280. (Japanese Original and English Abstract).
Baum et al. "Isolation of a Candidate Human Hematopoietc Stem-Cell Population." PNAS. 89(1992):2804-2808.
Belovari et al. "Differentiation of Rat Neural Tissue in a Serum-Free Embryo Culture Model Followed by in vivo Transplantation." Croat. Med. J. 42.6(2001):611-617. (English Abstract Only).
Berardi et al. "Individual CD34+CD38lowCD19-CD10—Progenitor Cells from Human Cord Blood Generate B Lymphocytes and Granulocytes." Blood. 89.10(1997):3554-3564.
Berkner. "Development of Adenovirus Vectors for the Expression of Heterologous Genes." BioTech. 6.7(1998):616-629.
Bernhard et al. "Generation of Immunostimulatory Dendritic Cells from Human CD34+ Hematopoietic Progenitor Cells of the Bone Marrow and Peripheral Blood." Cancer Res. 55(1995):1099-1104.
Bertagnolo et al. "Phophoinositide 3-Kinase Activity is Essential for All-Trans-Retinoic Acid-Induced Granulocyte Differentiation of HL-60 Cells." Cancer Res. 59(1999):542-546.
Bhat-Nakshatri et al. "Tumour Necrosis Factor and PI3-Kinase Control Oestrogen Receptor Alpha Protein Level and its Transrepression Function." Brit. J. Cancer. 90(2004):853-859.

(56) References Cited

OTHER PUBLICATIONS

Bhatia et al. "Purification of Primitive Human Hematopoietic Cells Capable of Repopulating Immune-Deficient Mice." *PNAS.* 94(1997):5320-5325.
Bi et al. "Effect of Lactoferrin on Proliferation and Differentiation of the Jurkat Human Lymphoblastic T Cell Line." *Arch. Immunol. Ther. Exp.* 45.4(1997):315-320.
Bieback et al. "Critical Parameters for the Isolation of Mesenchymal Stem Cell from Umbilical Cord Blood." *Stem Cells.* 22(2004):625-634.
Bird et al. "Single-Chain Antigen-Binding Proteins." *Science.* 242(1988):423-426.
Birkenkamp et al. "An Inhibitor of PI3-K Differentially Affects Proliferation and IL-6 Protein Secretion in Normal and Leukemic Myeloid Cells Depending on the Stage of Differentiation." *Exp. Hematol.* 28.11(2000):1239-1249.
Blau et al. "Fetal Hemoglobin in Acute and Chronic Stage of Erythroid Expansion." *Blood.* 8.1(1993):227-233.
Blyszczuk et al. "Embryonic Stem Cells Differentiate into Insulin-Producing Cells without Selection of Nestin-Expressing Cells." *Int. J. Dev. Biol.* 48(2004):1095-1104.
Boerner et al. "Production of Antigen-Specific Human Monoclonal Antibodies from in vitro-Primed Human Splenocytes." *J. Immunol.* 147.1(1991):86-95.
Bohmer et al. "Fetal Cell Isolation from Maternal Blood Cultures by Flow Cytometric Hemoglobin Profiles." *Fetal Diagn. Ther.* 17.2(2002):83-89.
Boitano et al. "Aryl Hydrocarbon Receptor Antagonists Promote the Expansion of Human Hematopoietic Stem Cells." *Science.* 329. 5997(2010):1345-1348.
Bongers et al. "Kinetics of Dipeptyl Peptidase IV Proteolysis of Growth Hormone-Releasing Factor and Analogs." *Biochim. Biophs. Acta.* 1122(1992):147-153.
Bonora-Centelles et al. "Sequential Hepatogenic Transdifferentiation of Adipose Tissue-Derived Stem Cell: Relevance of Different Extracellular Signaling Molecules, Transcription Factors Involved, and Expression of New Key Marker Genes." *Cell Transplant.* 18.12(2009):1319-1340.
Borthwick et al. "A Comparison of Cupruretic Responses to Various Tetramines and D-penicillamine." *J. Lab. Clin. Med.* 95.4(1980):575-580.
Brandt et al. "Ex Vivo Expanstion of Autologous Bone Marrow CD34+ Cells with Porcine Microvascular Endothelial Cells Results in a Graft Capable of Rescuing Lethally Irradiated Baboons." *Blood.* 94.1(1999):106-113.
Brazelton et al. "From Marrow to Brain: Expression of Neuronal Phenotypes in Adult Mice." *Science.* 290.5497(2000):1775-1779.
Breitman et al. "Induction of Differentiation of the Human Promylocytic Leukemia Cell Line (HL-60) by Retinoic Acid." *PNAS.* 77.5(1980):2936-2940.
Briddell et al. "Purification of CD34+ Cells is Essential for Optimal Ex Vivo Expansion of Umbilical Cord Blood Cells." *J. Hematother.* 6(1997):145-150.
Brigham et al. "Rapid Communication: In vivo Transfection of Murine Lungs with a Functioning Prokaryotic Gene Using a Liposome Vehicle." *J. Med. Sci.* 298.4(1989):278-281.
Brott et al. "Flow Cytometric Characterization of Perfused Human Bone Marrow Cultures: Identification of the Major Cell Lineages and Correlation with the CFU-GM Assay." *Cytometry Part A.* 53A(2003):22-27.
Broxmeyer. "Regulation of Hematopoiesis by Chemokine Family Members." *Int. J. Hematol.* 74(2001):9-17.
Brugger et al. "Ex Vivo Expanstion of Enriched Peripheral Blood CD34+ Progenitor Cells by Stem Cell Factor, Interleukin-1β (IL-1β), IL-6, IL-3, Interferon-γ, and Erythropoietin." *Blood.* 81.10(1993):2579-2584.
Brugger et al. "Reconstitution of Hematopoiesis after High-Dose Chemotherapy by Autologous Progenitor Cells Generated Ex Vivo." *N. Eng. J. Med.* 333.5(1995):283-287.
Brugnera et al. "Cloning, Chromosomal Mapping and Characterization of the Human Metal-Regulatory Transcription Factor MTF-1." *Nucleic Acids Res.* 22.15(1994):3167-3173.
Bryder et al. "Hematopoietic Stem Cells: The Paradigmatic Tissue-Specific Stem Cell." *Am. J. Pathol.* 169.2(2006):338-346.
Burgada et al. "Synthesis of New Phosphonated Tripod Ligands as Putative New Therapeutic Agents in the Chelation Treatment of Metal Intoxications." *Eur. J. Chem.* (2001):349-352.
Buskin et al. "Identification of a Myocyte Nuclear Factor that Binds to the Muscle-Specific Enhancer of the Mouse Muscle Creatine Kinase Gene." *Mol. Cell. Biol.* 9.6(1989):2627-2640.
Butt. "Introduction to Chemical Reactor Therapy." *Reaction Kinetics and Reactor Design.* Boca Raton, FL: CRC Press. (1980):184-241.
Cable et al. "Exposure of Primary Rat Hepatocytes in Long-Term DMSO Culture to Selected Transition Metals Induces Hepatocyte Proliferation and Formation of Duct-Like Structure." *Hepatol.* 26.6(1997):1444-1457.
Cakir-Kiefer et al. "Kinetic Competence of the cADP-Ribose-CD38 Complex as an Intermediate in the D38/NAD+ Glycohydrolase-Catalysed Reactions: Implication for CD38 Signalling." *Biochem. J.* 358(2001):399-406.
Caliaro et al. "Response of Four Human Ovarian Carcinoma Cell Lines to All-Trans Retinoic Acid: Relationship with Induction of Differentiation and Retinoic Acid Receptor Expression." *Int. J. Cancer.* 56.5(1994):743-748.
Canaple et al. "Improving Cell Encapsulation Through Size Control." *J. Biomater. Sci. Polym. Ed.* 13.7(2002):783-796.
Casal et al. "In utero Transplantation of Fetal Liver Cells in the Mucopolysaccharidosis Type VII Mouse Results in Low-Level Chimerism, but Overexpression of β-Glucuronidase can Delay Onset of Clinical Signs." *Gene Ther.* 97.6(2001):1625-1634.
Cepko. "Overview of the Retrovirus Transduction System." *Short Protocols in Molecular Biology.* Unit 9/10-9/14. (1984):9-41-9-57.
Chang et al. "Procedures for Microencapsulation of Enzymes, Cells and Genetically Engineered Microorganisms." *Mol. Biotechnol.* 17.3(2001):249-260.
Charrier et al. "Normal Human Bone Marrow CD34+CD133+ Cells Contain Primitive Cells Able to Produce Different Categories of Colony-Forming Unit Megacryocytes in vitro." *Exp. Hematol.* 30(2002):1051-1060.
Chen et al. "Differentiation of Rat Marrow Mesenchymal Stem Cells into Pancreatic Islet Beta-Cells." *World J. Gastroenterol.* 10.20(2004):3016-3020.
Chen et al. "Fibroblast Growth Factor (FGF) Signaling Through PI 3-Kinase and Akt/PKS is Required for Embryoid Body Differentiation." *Oncogene.* 19(2000):3750-3756.
Chen et al. "Therapeutic Benefit of Intravenous Administration of Bone Marrow Stromal Cells after Cerebral Ischemia in Rats." *Stroke.* 32.4(2001):1005-1011.
Chia et al. "Multi-Layered Microcapsules for Cell Encapsulation." *Biomaterials.* 23.2(2002):849-856.
Chisi et al. "Inhibitory Action of the Peptide AcSDKP on the Proliferative State of Hematopoietic Stem Cells in the Presence of Captopril but not Lisinopril." *Stem Cells.* 15.6(1997):455-460.
Chivu et al. "In Vitro Hepatic Differentiation of Human Bone Marrow Mesenchymal Stem Cells under Differential Exposure to Liver-Specific Factors." *Translational Res.* 154.3(2009):122-132.
Chowhudry et al. "Long-Term Improvement of Hypercholesterolemia after ex Vivo Gene Therapy in LDLR-Deficient Rabbits." *Science.* 254(1991):1802-1805.
Christopherson et al. "Cell Surface Peptidase CD26/Dipeptidylpeptidase IV Regulates CXCL12/Stromal Cell-Derived Factor-1?-Mediated Chemotaxis of Human Cord Blood CD34+ Progenitor Cells."*J. Immunol.* 169(2002):7000-7008.
Christopherson et al. "Modulation of Hematopoietic Stem Cell Homing and Engraftment by CD26." *Science.* 305(2004):1000-1003.
Cicuttini et al. "Support of Human Cord Blood Progeniotr Cells on Human Stromal Cell Lines Transformed by SV40 Larger T Antigen Under the Influence of an Inducible (Metallothionein) Promoter." *Blood.* 80.1(1992):102-112.

(56) References Cited

OTHER PUBLICATIONS

Cole et al. "The EBV-Hybridoma Technique and its Application to Human Lung Cancer." *Monoclonal Antibodies Cancer Ther.* (1985):77-96.
Collins et al. "Stirred Culture of Peripheral and Cord Blood Hematopoietic Cells Offers Advantages over Traditional Static Systems for Clinically Relevant Applications." *Biotechnol. Bioeng.* 59.5(1998):534-543.
Colter et al. "CD34+ Progenitor Cell Selection: Clinical Transplantation, Tumor Cell Purging, Gene Therapy, Ex Vivo Expansion, and Cord Blood Processing." *J. Hematol.* 5(1996):179-184.
Corda et al. "Functional Aspects of Protein Mono-ADP-Ribosylation." *EMBO J.* 22.9(2003):1953-1958.
Coutinho et al. "Effects of Recombinant Human Granulocyte Colony-Stimulating Factor (CSF), Human Granulocyte Macrophage-CSF, and Gibbon Interleukin-3 on Hemaotpoiesis in Human Long-Term Bone Marrow Culture." *Blood.* 75.11(1990):2118-2129.
Cowan et al. "Bone Morphogenetic Protein 2 and Retinoic Acid Accelerate in Vivo Bone Formation, Osteoclast Recruitment, and Bone Turnover." *Tissue Eng.* 11.3-4(2005):645-658.
Cristiano et al. "Hepatic Gene Therapy: Adenovirus Enhancement of Receptor-Mediated Gene Delivery and Expression in Primary Hepatocytes." *PNAS.* 90(1993):2122-2126.
Curiel et al. "Adenovirus Enhancement of Transferrin-Polylysine-Medaited Gene Delivery." *PNAS.* 88(1991):8850-8854.
Czauderna et al. "Functional Studies of the PI(3)-Kinase Signalling Pathway Employing Synthetic and Expressed siRNA." *Nucleic Acids Res.* 31.2(2003):670-682.
Czyz et al. "Potential of Embryonic and Adult Stem Cell in vitro." *Biol. Chem.* 384(2003):1391-1409.
Côté al. "Response to Histone Deacetylase Inhibition of Novel PML/RARα Mutants Detected in Retinoic Acid-Resistant APL Cells." *Blood.* 100.7(2002):2586-2596. (Abstract Only).
Dabeva et al. "Transcription Factor and Liver-Specific mRNA Expression in Facultative Epithelial Progenitor Cells of Liver and Pancreas." *Am. J. Pathol.* 147(1995):1633-1648. (Abstract Only).
Dahl et al. "Transformation of Hematopoietic Cells by the Ski Oncoprotein Involves Repression of Retinoic Acid Receptor Signaling." *PNAS.* 95.19(1998):11187-11192.
Dai et al. "Gene Therapy via Primary Myoblasts: Long-Term Expression of Factor IX Protein Following Transplantation in vivo." *PNAS.* 89(1992):10892-10895.
Dalyot et al. "Adult and Neonatal Patterns of Human Globin Gene Expression are Recapitulated in Liquid Cultures." *Exp. Hematol.* 20(1992):1141-1145. (Abstract Only).
Danos et al. "Safe and Efficient Generation of Recombinant Retroviruses with Amphotropic and Ecotropic Host Ranges." *PNAS.* 85(1988):6460-6464.
Datta et al. "Ionizing Radiation Activates Transcription of the EGR1 Gene via Carg Elements." *PNAS.* 89(1992):10149-10153.
De Bruyn et al. "Comparison of the Coexpression of CD33 and HLA-DR Antigens on CD34+ Purified Cells from Human Cord Blood Marrow." *Stem Cells.* 13(1995):281-288.
de la Cruz et al. "Do Protein Motifs Read the Histone Code?" *BioEssays.* 27.2(2005):164-175.
De Luca et al. "Retinoic Acid is a Potent Regulator of Growth Plate Chondrogenesis." *Endocrinol.* 141.1(2000):346-353. (Abstract Only).
De Ridder et al. "Hypoxic Tumor Cell Radiosensitization: Role of the iNOS/NO Pathway." *Bull. Cancer.* 95.3(2008):282-291.
De Wynter et al. "CD34+AC133+ Cells Isolated from Cord Blood are Highly Enriched in Long-Term Culture-Initiating Cells, NOD/SCID-Repopulating Cells and Dendritic Cell Progenitors." *Stem Cells.* 16(1998):387-396.
Defacque et al. "Expression of Retinoid X Receptor Alpha is Increased Upon Moncytic Cell Differentiation." *Biochem. Biophys. Res. Commun.* 220(1996):315-322.
Desai. "Microfabrication Technology for Pancreatic Cell Encapsulation." *Expert Opin. Biol. Ther.* 2.6(2002):633-646.

Dexter et al. "Conditions Controlling the Proliferation of Haemopoietic Stem Cells In Vitro." *J. Cell Physiol.* 91(1976):335-344.
DOD, Tetraethylene Pentamine DOD Hazardous Material Information; 6810-00F01771. (1991).
Donovan et al. "The End of the Beginning for Pluripotent Stem Cells." *Nature.* 414.6859(2001):92-97.
Dosil et al. "Mitogenic Signalling and Substrate Specificity of the Flk2/Flt3 Receptor Tyrosine Kinase in Fibroblasts and Interleuk in 3-Dependent Hematopoietic Cells." *Mol. Biol.* 13.1(1993):6572-6585. (Abstract Only).
Douer et al. "All-Trans-Retinoic Acid Effects the Growth, Differentiation and Apoptosis of Normal Human Myeloid Progenitors Derived from Purified CD34+ Bone Marrow Cells." *Leukemia.* 14.5(2000):874-881.
Drayson et al. "Cell Proliferation and CD11b Expression are Controlled Independently During HL60 Cell Differentiation Initiated by 1,25α-Dihydroxyvitamin D3 or All-trans-Retinoic Acid." *Exp. Cell Res.* 266.1(2001):126-134. (Abstract Only).
Dubois et al. "Treatment of Wilson's Disease with Triethylene Tetramine Hydrochloride (Trientine)." *J. Ped. Gastroenterol. Nutr.* 10.1(1990):77-81. (Abstract Only).
Duncan et al. "Repair of Mylein Disease: Strategies and Progress in Animal Models." *Mol. Med. Today.* 3.12(1997):554-561. (Abstract Only).
Ebner et al. "Distinct Roles for PI3K in Proliferation and Survival of Oligodendrocyte Progenitor Cells." *J. Neurosci. Res.* 62(2000):336-345.
Eglitis. "Gene Expression in Mice after High Efficiency Retroviral-Mediated Gene Transfer." *Science.* 230(1985):1395-1398.
Ehring et al. "Expansion of HPCs from Cord Blood in a Novel 3D Matrix." *Cytotherapy.* 5.6(2003):490-499.
Eipers et al. "Retroviral-Mediated Gene Transfer in Human Bone Marrow Cells Grown in Continuous Perfusion Culture Vessels." *Blood.* 86.10(1995):3754-3762.
Emerson et al. "Ex Vivo Expansion of Hematopoietic Precursors, Progenitors, and Stem Cells: The Next Generation of Cellular Therapeutics." *Blood.* 87.8(1996):3082-3088.
Englisch et al. "Chemically Modified Oligonucleotides as Probes and Inhibitors." *Angew. Chem.* 30.6(1991):613-629.
Farre et al. "FDF-4 Increases in vitro Expansion Rate of Human Adult Bone Marrow-Derived Mesenchymal Stem Cells." *Growth Factors.* 25.2(2007):71-76.
Fasouliotis et al. "Human Umbilical Cord Blood Banking and Transplantation: A Atet of the Art." *Eur. J. Obstet. Gynecol. Reprod. Biol.* 90.1(2000):13-25.
Feldman. "Israeli Start-Up Gamida-Cell to Receive Prize." *Globes Online.* Web. (2004).
Ferbeyre. "PML A Target of Translocations in APL is a Regulator of Cellular Senescence." *Leukemia.* 16(2002):1918-1926. (Abstract Only).
Ferrari et al. "Muscle Regeneration by Bone Marrow-Derived Myogenic Progenitors." *Science.* 279.5356(1998): 1528-1530.
Ferrari et al. "Erratum: Muscle Regeneration by Bone Marrow-Derived Myogenic Progenitors." *Science.* 281.5379(1998):923.
Ferrero et al. "The Metamorphosis of a Molecule: From Soluble Enzyme to the Leukocyte Receptor CD38." *J. Leukocyte Biol.* 65.2(1999):151-161.
Ferry et al. "Retroviral-Mediated Gene Transfer into Hepatocytes in vivo." *PNAS.* 88(1991):8377-8381.
Fibach et al. "Growth of Human Normal Erythroid Progenitors in Liquid Culture: A Comparison with Colony Growth in Semisolid Culture." *Int. J. Cell Cloing.* 9(1991):57-64. (Abstract Only).
Fibach et al. "Normal Differentiation of Myeloid Leukemic Cells Induced by a Protein Differentiation-Inducing Protein." *Nat. New Biol.* 237.78(1972):276-278.
Fibach et al. "Proliferation and Maturation of Human Erythroid Progenitors in Liquid Culture." *Blood.* 73.1(1989):100-103. (Abstract Only).
Fibach et al. "Retinoic Acid Antagonist Inhibits CD38 Antigen Expression on Human Hematopoietic Cells." *Blood.* 100. 11(2002):172A. (Abstract #644).

(56) References Cited

OTHER PUBLICATIONS

Fibach et al. "The Two-Step Liquid Culture: A Novel Procedure for Studying Maturation of Human Normal and Pathological Erythroid Precursors." *Stem Cells.* 11.S1(1993):36-41. (Abstract Only).
Fietz et al. "Culturing Human Umbilical Cord Blood: A Compariso of Mononuclear Vs CD34+ Selected Cells." *Bone Marrow Transplant.* 23(1999):1109-1115.
Filvaroff et al. "Functional Evidence for an Extracellular Calcium Receptor Mechanism Triggering Tyrosine Kinase Activation Associated with Mouse Keratinocyte Differentiation." *J. Biol. Chem.* 369.34(1994):21735-21740.
Fingl et al. "General Principles." *Basis of THerapeutics.* New York: Macmillan Publishing Co., Inc. 5th ed. (1975):1-46.
Fisch et al. "Generation of Antigen-Presenting Cells for Soluble Protein Antigens ex vivo from Peripheral Blood CD34+ Hematopoietic Progenitor Cells in Cancer Patients." *Eur. J. Immunol.* 26(1996):595-600.
Fishwild et al. "High-Avidity Human IgGκ Monoclonal Antibodies from a Novel Strain of Minilocus Transgenic Mice." *Nat. Biotechnol.* 14(1996):845-851.
Flores et al. "Akt-Mediated Survival of Oligodendrocytes Induced by Neuregulins." *J. Neurosci.* 20.20(2000):7622-7630.
Flotte et al. "Expression of the Cystic Fibrosis Transmembrane Conductance Regulators from a Novel Adeno-Associated Virus Promoter." *J. Biol. Chem.* 268.5(1993):3781-3790.
Flotte et al. "Gene Expression from Adeno-Associated Virus Vectors in Airways Epithelial Cells." *Am. J. Resp. Cell Mol. Biol.* 7(1992):349-356.
Forraz et al. "AC133+ Umbilical Cord Blood Progenitors Demonstrate Rapid Self-Renewal and Low Apoptosis." *Br. J. Haematol.* 119.2(2002):516-524.
Fosmire. "Zinc Toxicity." *Am. J. Clin. Nutr.* 51.2(1990):225-227. (Abstract Only).
Freedman et al. "Generation of Human T Lymphocytes from Bone Marrow CD34+ Cells in vitro." *Nat. Med.* 2.1(1995):46-51.
Freshney, ed. "Culture of Specific Cell Types." *Culture of Animal Cells.* New York: John Wiley and Sons. Third Ed. (1994):309-311, 327-328.
Fry. "Phosphoinositide 3-Kinase Signalling in Breast Cancer: How Big a Role Might it Play?" *Breast Cancer Res.* 3.5(2001):304-312.
Fukuda. "Development of Regenerative Cardiomyoctes from Mesenchymal Stem Cells for Cardiovascular Tissue Engineering." *Artif. Organs.* 25.3(2001):187-193.
Gagnon et al. "Activation of Protein Kinase B and Induction of Adipogenesis by Insulin in 3T3-L1 Preadipocytes." *Diabetes.* 48(1999):691-698.
Gallacher et al. "Isolation and Characterization of Human CD34-Lin- and CD34+Lin-Hematopoietic Stem Cells Using Cell Surface Markers AC133 and CD7." *Blood.* 95.9(2000):2813-2820.
Gang et al. "Skeletal Myogenic Differentiation of Mesenchymal Stem Cells Isolated from Human Umbilical Cord Blood." *Stem Cells.* 22.4(2004):617-624.
Garmy-Susini et al. "Integrin α4β1-VCAM-1-Mediated Adhesion Between Endothelial and Mural Cells is Required for Blood Vessel Maturation." *J. Clin. Invest.* 115.6(2005):1542-1551.
Gloeckner et al. "New Miniaturization Hollow-Fiber Bioreactor for in Vivo Like Cell Culture, Cell Expansion, and Production of Cell-Derived Products." *Biotechnol. Prog.* 17(2001):828-831.
Gluckman et al. "Hematopoietic Reconstitution in a Patient with Fanconi's Anemia by Means of Umbilical-Cord Blood from an HLA-Identical Sibling." *New Eng. J. Med.* 321.17(1989):1174-1178.
Gossler et al. "Transgenesis by Means of Blasocyst-Derived Embryonic Stem Cell Lines." *PNAS.* 83(1986):9065-9069.
Gould-Fogerite et al. "Chimerasome-Mediated Transfer in vitro and in vivo." *Gene.* 84.2(1989):429-438. (Abstract Only).
Grande et al. "Physiological Levels of 1α, 25 Dihydroxyvitamin D3 Induce the Monocytic Commitment of CD34+ Hematopoietic Progenitors." *J. Leukoc. Biol.* 71.4(2002):641-651.

Grenda et al. "Mice Expressing a Neutrophil Elastase Mutation Derived from Patients with Severe Congenital Neutrophenia have Normal Granulopoiesis." *Blood.* 100.9(2002):3221-3228.
Gur et al. "Tolerance Induction by Megadose Hematopoietic Progenitor Cells: Expansion of Veto Cells by Short-Term Culture of Purified Human CD34+ Cells." *Blood.* 99.11(2002):4174-4181.
Haj-Ahmad et al. "Development of a Helper-Independent Human Adenovirus Vector and its Use in the Transfer of the Herpes Simplex Virus Thymidine Kinase Gene." *J. Virol.* 57.1(1986):267-274.
Hamilton. "Stem Cell Technology to Treat Leukemia Patients Show Promise." *Wall Street Journal Online.* (2003).
Hammond et al. "Suppression of in vitro Granulocytopoiesis by Captopril and Penicillamine." *Exp. Hematol.* 16(1988):674-680.
Handgretinger et al. "Biology and Plasticity of CD133+ Hematopoietic Stem Cells." *Ann. NY Acad. Sci.* 996(2003):141-151.
Hatayama et al. "Regulation of HSP70 Synthesis by Cupric Sulfate and Zinc Sulfate in Thermotolerant HeLa Cells." *J. Biochem.* 114.4(1993):592-597. (Abstract Only).
Haviernik et al. "Tissue Inhibitor of Matrix Metallaproteinase-1 Overexpression in M1 Myeloblasts Impairs IL-6-Induced Differentiation." *Oncogene.* 23.57(2204):9212-9219. (Abstract Only).
Hayashi et al. "Changes in the Balance of Phosphoinositide 3-Kinase/Protein Kianse B (Akt) and the Mitogen-Activated Protein Kinases (ERK/p38MAPK) Determine a Phenotype of Visceral and Vascular Smooth Muscle Cells." *J. Cell Biol.* 145.4(1999):727-740.
Haylock et al. "Ex Vivo Expansion and Maturation of Peripheral Blood CD34+ Cells Into the Myeloid Lineage." *Blood.* 80.5(1992):1405-1412.
Hermonat et al. "Use of Adeno-Associated Virus as a Mammalian DNA Cloning Vector: Transduction of Neomycin Resistance into Mammalian Tissue Culture Cells." *PNAS.* 81(1984):6466-6470.
Herz et al. "Adenovirus-Mediated Transfer of Low Density Lipoprotein Receptor Gene Acutely Accelerates Cholesterol Clearance in Normal Mice." *PNAS.* 90(1993):2812-2816.
Heslop et al. "Long-Term Restoration of Immunity Against Epstein-Barr Virus Infection by Adoptive Transfer of Gene-Modified Virus-Specific T Lymphocytes." *Nat. Med.* 2.5(1996):551-555.
Heuchel et al. "The Transcription Factor MTF-1 is Essential for Basal and Heavy Metal-Induced Metallotionein Gene Expression." *EMBO J.* 13.12(1994):2870-2875.
Hida et al. "Existence of Retinoic Acid-Receptor-Independent Retinoid X-Receptor-Dependent Pathway in Myeloid Cell Function." *Japan. J. Pharmacol.* 85.1(2001):60-69.
Higashi et al. "Autologous Bone-Marrow Mononuclear Cell Implantation Improves Endothelium-Dependent Vasodilation in Patients with Limb Ischemia." *Circulation.* 109(2004):1215-1218.
Hino et al. "A Long-Term Culture of Human Hepatocytes which Show a High Growth Potential and Express their Differential Phenotypes." *Biochem. Biophys. Res. Commun.* 256.1(1999):184-191. (Abstract Only).
Hirase et al. "Anemia and Neutropenia in a Case of Copper Deficiency: Role of Copper in Normal in Hematopoiesis." *Acta Haematol.* 87.4(1992):195-197.
Hirose et al. "Identification of a Transposon-Related RNA Down-Regulated by Retinoic Acid in Embryonic Carcinoma and Embryonic Stem Cells." *Exp. Cell Res.* 221.2(1995):294-300. (Abstract Only).
Hmama et al. "1α, 25-Dihydroxyvitamin D3-Induced Myeloid Cell Differentiation is Regulated by a Vitamin D Receptor-Phosphatidylinositol 3-Kinase Signaling Complex." *J. Exp. Med.* 190.11(1999):1583-1594.
Hoffman et al. "Zinc-Induced Copper Deficiency." *Gastroenterol.* 94.2(1988):508-512. (Abstract Only).
Hofmeister et al. "Ex vivo Expansion of Umbilical Cord Blood Stem Cells for Transplantation: Growing Knowledge from the Hematopoietic Niche." *Bone Marrow Transplant.* 39(2007):11-23.
Holleman. "Triethylene Tetramine." *Chemical Hazard Iformation Profile Draft Report.* (1990).
Hoogenboom et al. "By-Passing Immunisation: Human Antibodies from Synthetic Repertoires of Germline VH Gene Segments Rearranged in Vitro." *J. Mol. Biol.* 227(1992):381-388.

(56) References Cited

OTHER PUBLICATIONS

Hori et al. "Growth Inhibitors Promote Differentiation of Insulin-Producing Tissue from Embryonic Stem Cells." *PNAS*. 99.25(2002):16105-16110.
Hottinger et al. "The Copper Chelator D-Penicillamine Delays Onset of Disease A Extends Survival in a Transgenic Mouse Model of Familial Amyotrophic Lateral Sclerosis." *Eur. J. Neurosci*. 9.7(1997):1548-1551. (Abstract Only).
Howard et al. "Formation and Hydrolysis of Cyclic Acid ADP-Ribose Catalyzed by Lymphocyte Antigen CD38." *Science*. 262. 5136(1993):1056-1059.
Huang et al. "Differentiation of Human U937 Promonocytic Cells is Impaired by Moderate Copper-Deficiency." *Exp. Biol. Med*. 226.3(2001):222-228.
Huber et al. "Retroviral-Mediated Gene Therapy for the Treatment of Hepatocellular Carcinoma: An Innovative Approach for Cancer Therapy." *PNAS*. 88(1991):8039-8043.
Hutvánger et al. "RNAi: Nature Abhors a Double-Strand." *Curr. Opin. Genet. Dev*. 12(2002):225-232.
Hwu et al. "Functional and Molecular Characterization fo Tumor-Infiltrating Lymphocytes Transduced with Tumor Necrosis Factor-α cDNA for the Gene Therapy of Cancer in Humans." *J. Immunol*. 150.9(1993):4104-4115.
Hühn et al. "Molecular Analysis of CD26-Mediated Signal Transduction in T Cells." *Immunol. Lett*. 72(2000):127-132.
Imai et al. "Selective Secretion of Chemoattractants for Haemapoietic Progenitor Cells by Bone Marrow Endothelial Cells: A Possible Role in Homing of Haemopoietic Progenitor Cells to Bone Marrow." *Brit. J. Haematol*. 106(1999):905-911.
Imitola et al. "Directed Migration of Neural Stem Cells to Sites of CNS Injury by the Stroman Cell-Derived Factor 1α/CXC Chemokine Receptor 4 Pathway." *PNAS*. 101.52(2004):18117-18122.
Inbar et al. "Localization of Antibody-Combining Sites Within the Variable Portions of Heavy and Light Chains." *PNAS*. 69.9(1972):2659-2662.
Itoh et al. "Inhibition of Urokinase Receptor (uPAR) Expression by RNA-Cleaving Catalytic DNA (DNAzyme) Containing Antisense uPAR." *Mol. Ther*. 5.5(2002):S134. (Abstract #409).
Jackson et al. "Regeneration of Ischemic Cardiac Muscle and Vascular Endothelium by Adult Stem Cells." *J. Clin. Invest*. 107. 11(2001):1395-1402.
Jelinek et al. "Novel Bioreactors for the ex vivo Cultivation of Hematopoietic Cells." *Eng. Life Sci*. 2.1(2002):15-18.
Jiang et al. "Phosphatidylinositol 3-Kinase Signaling Mediates Angiogenesis and Expression of Vascular Endothelial Growth Factor in Endothelial Cells." *PNAS*. 97.4(2000):1749-1753.
Johnson et al. "Synthesis and Biological Activity of High-Affinity Retinoic Acid Receptor Antagonists." *Bioorg. Med. Chem*. 7.7(1999):1321-1338.
Johnson et al. "The Cytokines IL-3 and GM-CSF Regulate the Transcriptional Activity of Retinoic Acid Receptors in Different in vitro Models of Myeloid Differentiation." *Blood*. 99.3(2002):746-753.
Jones et al. "Replacing the Complementarity-Determining Regions on a Human Antibody with Those from a Mouse." *Nature*. 321(1986):522-525.
Kahn et al. "Overexpression of CXCR4 on Human CD34+ Progenitors Increases their Proliferation, Migration, and NOD/SCID Repopulation." *Blood*. 103.8(2004):2942-2949.
Kang et al. "Retinoic Acid and its Receptors Repress the Expression and Transactivation Functions of Nur77: A Possible Mechanism for the Inhibition of Apoptosis by Retinoic Acid." *Exp. Cell Res*. 256(2000):545-554.
Kassis et al. "Isolation of Mesenchymal Stem Cells from G-CSF-Mobilized Human Peripheral Blood Using Fibrin Microbeads." *Bone Marrow Transplant*. 37.10(2006):967-976.
Kastner et al. "Positive and Negative Regulation of Granulopoiesis by Endogenous RARalpha."*Blood*. 97.5(2001):1314-1320. (Abstract Only).

Kaufman et al. "Translational Efficiency of Polycistronic mRNAs and Their Utilization to Express Heterologous Genes in Mammalian Cells." *EMBO J*. 6.1(1987):187-193.
Kawa et al. "Stem Cell Factor and/or Endothelin-3 Dependent Immortal Melanoblast and Melanocyte Populations Derived from Mouse Neural Crest Cells." *Pigment Cell Res*. 13.58(2000):73-80.
Kay et al. "Hepatic Gene Therapy: Persistent Expression of Human α1-Antitrypsin in Mice after Direct Gene Delivery In Vivo." *Hum. Gene Ther*. 3(1992):641-647.
Keith et al. "Multicomponent Therapeutics for Networked Systems." *Nat. Rev. Drug Disc*. 4(2005):1-8.
Kern et al. "Comparative Analysis of Mesenchymal Stem Cells from Bone Marrow, Umbilical Cord Blood, or Adipose Tissue." *Stem Cells*. 24(2006):1294-1301.
Khachigian. "DNAzymes: Cutting a Path to a New Class of Therapeutics." *Curr. Opin. Mot Ther*. 4.2(2002):119-121.
Kim. "Differentiation and Identification of the Two Catalytic Metal Binding Sites in Bovine Lens Leucine Aminopeptidase by X-Ray Crystallography." *PNAS*. 90.11(1993):5006-5010.
Kishimoto et al. "Molecular Mechanism of Human CD38 Gene Expression by Retinoic Acid." *J. Biol. Chem*. 273.25(1998):15429-15434.
Kitanaka et al. "CD38 Ligation in Human B Cell Progenitors Triggers Tyrosine Phophorylation of CD19 and Association of CD19 with Lyn and Phosphatidylinositol 3-Kinase." *J. Immunol*. 159.1(1997):184-192. (Abstract Only).
Kizaki et al. "Regulation of Manganese Superoxide Dismutase and Other Antioxidant Genes in Normal and Leukemic Hematopoietic Cells and Their Relationship to Cytotoxicity by Tumor Necrosis Factor." *Blood*. 82.4(1993):1142-1150.
Kobari et al. "CD133+ Cell Selection is an Alternative to CD34+ Cell Selection for Ex Vivo Expansion of Hematopoietic Stem Cells." *J. Hematother. Stem Cell Res*. 10.2(2001):273-281.
Kocher et al. "Neovascularization of Ischemic Myocardium by Human Bone-Marrow-Derived Angioblasts Prevents Cardiomyocyte Apoptosis, Reduces Remodeling and Improves Cardiac Function." *Nat. Med*. 7.4(2001):430-436.
Kohroki et al. "Induction of Differentiation and Apoptosis by Dithizone in Human Myeloid Leukemia Cell Lines." *Leuk. Res*. 22.5(1998):405-412.
Koizumi et al. "Large Scale Purification of Human Blood CD34+ Cells from Cryopreserved Peripheral Blood Stem Cells, Using a Nylon-Fiber Syringe System and Immunomagnetic Microspheres." *Bone Marrow Transplant*. 26(2000):787-793.
Koller et al. "Large-Scale Expansion of Human Stem and Progenitor Cells from Bone Marrow Mononuclear Cells in Continuous Perfusion Cultures." *Blood*. 82.2(1993):378-384.
Krause et al. "Multi-Organ, Multi-Lineage Engraftment by a Single Bone Marrow-Derived Stem Cell." *Cell*. 105.3(2001):369-377. (Abstract Only).
Kronenwett et al. "Oligodeoxyribonucleotide Uptake in Primary Human Hematopoietic Cells is Enhanced by Cationic Lipids and Depends on the Hematopoietic Cell Subset." *Blood*. 91.3(1998):852-862.
Ku et al. "Committing Embryonic Stem Cells to Early Endocrine Pancreas In Vitro." *Stem Cells*. 22(2004):1205-1217.
Kumagai et al. "Ligation of CD38 Suppresses Human B Lymphopoiesis." *J. Exp. Med*. 181.3(1995):1101-1110.
Kähne et al. "Dipeptidyl Peptidase IV: A Cell Surface Peptidase Involved in Regulating T Cell Growth (Review)." *Int. J. Mol. Med*. 4(1999):3-15.
Köhler et al. "Defining Optimum Conditions for the Ex Vivo Expansion of Human Umbilical Cord Blood Cells Influences of Progenitor Enrichment, Interference with Feeder Layers, Early-Acting Cytokines and Agitation of Culture Vessels." *Stem Cells*. 17.1(1999):19-24.
Labrecque et al. "Impaired Granulocytic Differentiation In Vitro in Hematopoietic Cells Lacking Retinoic Acid Receptors α1 and y." *Blood*. 92.2(1998):607-615.
Lagasse et al. "Purified Hematopoietic Stem Cells can Differentiate into Hepatocytes in vivo." *Nat. Med*. 6.11(2000):1229-1234.

(56) References Cited

OTHER PUBLICATIONS

Lam et al. "Preclinical ex vivo Expansion of Cord Blood Hematopoietic Stem and Progenitor Cells: Duration of Culture; the Media, Serum Supplements, and Growth Factors Used; and Engraftment in NOD/SCID Mice." *Transfusion.* 41.12(2001):1567-1576.
Lambeir et al. "Kinetic Investigation of Chemokine Truncation by CD26/DipeptidylPeptidase IV Reveals a Striking Selectivity within the Chemokine Family." *J. Biol. Chem.* 276.32(2001):29839-29845.
Lange et al. "Biological and Clinical Advances in Stem Cell Expansion." *Leukemia.* 10(1996):943-945.
Lapidot et al. "Cytokine Stimulation of Multilineage Hematopoiesis from Immature Human Cells Engrafte in SCID Mice." *Science.* 255(1992):1137-1141. (Abstract Only).
Larrick et al. "PCR Amplification of Antibody Genes." *Methods: A Companion to Methods in Enzymology.* 2.2(1991):106-110.
Lassila et al. "Role for Lys-His-Gly-NH2 in Avian and Murine B Cell Development." *Cell. Immunol.* 122.2(1989):319-328.
Lau et al. "A Peptide Molecule Mimicking the Copper (II) Transport Site of Human Serum Albumin." *J. Biol. Chem.* 249.18(1974):5878-5884.
Lavigne et al. "Enhanced Antisense Inhibition of Human Immunodeficiency Virus Type 1 in Cell Cultures by DLS Delivery System." *Biochem. Biophys. Res. Commun.* 237(1997):566-571.
Lawlor et al. "Coordinate Control of Muscle Cell Survival by Distinct Insulin-Like Growth Factor Activated Signaling Pathways." *J. Cell Biol.* 151.6(2000):1131-1140.
Lebkowski et al. "Rapid Isolation and Serum-Free Expansion of Human CD34+ Cells." *Blood Cells.* 20(1994):404-410.
Lee et al. "Clonal Expansion of Adult Rat Hepatic Stem Cell Line by Suppression of Asymmetric Cell Kinetics (SACK)." *Biotechnol. Bioeng.* 83.7(2003):760-771.
Lee et al. "Effect of Vitamin D Analog, EB1089, on Hematopoietic Stem Cells from Normal and Myeloid Leukemic Blasts." *Leukemia.* 10(1996):1751-1757.
Lee et al. "Repair of Ischemic Heart Disease with Novel Bone Marrow-Derived Multipotent Stem Cells." *Cell Cycle.* 4.7(2005):861-864.
Lemarchand et al. "Adenovirus-Mediated Transfr of a Recombinant Human α1-Antitrypsin cDNA to Human Endothelial Cells." *PNAS.* 89(1992):6482-6486.
Leslie et al. "An Activating Mutation in the Kit Receptor Abolishes the Stroma Requirement for Growth of ELM Erythropoietin." *Blood.* 92.12(1998):4798-4807.
Lewandowski et al. "Phosphatidylinositol 3-Kinases are Involved in the All-Trans Retinoic Acid-Induced Upregulation of CD38 Antigen on Human Haematopoietic Cells." *Brit. J. Hematol.* 118.2(2002):535-544.
Li et al. "Activation of Phosphatidylinostiol-3 Kinase (PI-3K) and Extracellular Regulated Kinases (Erk½) is Involved in Muscarinic Receptor-Mediated DNA Synthesis in Neural Progenitor Cells." *J. Neurosci.* 21.5(2001):1569-1579.
Li et al. "Cell Life Verus Cell Longevity: The Mysteries Surrounding the NAD+ Precursor Nicotinamide." *Curr. Med. Chem.* 13.8(2206):883-895.
Lianguzova et al. "PI3-Kinase Inhibitors LY294002 and Wortmannin have Different Effects on Proliferation of Murine Embryonic Stem Cells." *Tsitologiia.* 48.7(2006):560-568. (Abstact Only).
Lonberg et al. "Antigen-Specific Human Antibodies from Mice Comprising Four Distinct Genetic Modifications." *Nature.* 368(1994):856-859.
Lonberg et al. "Human Antibodies from Transgenic Mice." *Int. Rev. Immunol.* 13.1(1995):65-93.
Lovejoy et al. "Novel "Hybrid" Iron Chelators Derived from Aroylhydrazones and Thiosemicarbazones Demonstrate Selective Antiproliferative Activity Against Tumor Cells." *Blood.* 100.2(2002):666-676.
Lu et al. "A Novel Cell Encapsulation Method Using Photosensitive Poly(allylamine α-Cyanocinnamylideneacetate)." *J. Microencapsul.* 17.2(2000):245-251.
Lu et al. "Cell Encapsulation with Alginate and α-Phenoxycinnamylidene-Acetylated Poly(Allylamine)." *Biotechnol. Bioeng.* 70.5(2000):479-483.
Lu et al. "Intravenous Administration of Human Umbilical Cord Blood Reduces Neurological Deficit in the Rat after Traumatic Brain Injury." *Cell Transplant.* 11.3(2002):275-281. (Abstract Only).
Luft. "Making Sense Out of Antisense Oligodeoxynucleotide Delivery: Getting There is Half the Fun." *J. Mol. Med.* 76(1998):75-76.
Lupi et al. "Endogenous ADP-Ribosylation of the G Protein β Subunit Prevents the Inhibition of Type 1 Adenylyl Cyclase." *J. Biol. Chem.* 275.13(2000):9418-9424.
Lutton et al. "Zinc Porphyrins: Potent Inhibitors of Hematopoiesis in Animal and Human Bone Marrow." *PNAS.* 94(1997):1432-1436.
Ma et al. "Inhibition of Phosphatidylinositol 3-Kinase Causes Apoptosis in Retinoic Acid Differentiated HL-60 Leukemia Cells." *Cell Cycle.* 3.1(2004):67-70.
Mader et al. "A Steroid-Inducible Promoter for the Controlled Overexpression of Cloned Genes in Eukaryotic Cells." *PNAS.* 90(1993):5603-5607.
Madlambayana et al. "Controlling Culture Dynamics for the Expansion of Hematopoietic Stem Cells." *J. Hematother. Stem Cell Res.* 10.4(2001):481-492. (Abstract Only).
Maitra et al. "Human Mesenchymal Stem Cells Support Unrelated Donor Hematopoietic Stem Cells and Suppress T-cell Activation." *Bone Marrow Transplant.* 33.6(2004):597-604.
Manome et al. "Coinduction of C-Jun Gene Expression and Internucleosomal DNA Fragmentation by Ionizing Radiation." *Biochem.* 32(1993):10607-10613.
Mar et al. "A Conserved CATTCCT Motif is Required for Skeletal Muscle-Specific Activity of the Cardiac Troponin T Gene Promoter." *PNAS.* 85(1988):6404-6408.
Marcinkowska. "Does the Universal 'Signal Transduction Pathway of Differentiation' Exist? Comparison of Different Cell Differentiation Experimental Models with Differentiation of HL-60 Cells in Response to 1,25-dihydroxyvitamin D3." *Postepy Hig Med Dosw.* 53.2(1999):305-313. (Abstract Only).
Marks et al. "By-Passing Immunization: Building High Affinity Human Antibodies by Chain Shuffling." *Biotechnol.* 10(1992):779-783.
Marks et al. "By-Passing Immunization: Human Antibodies from V-Gene Libraries Displayed on Phage." *J. Mol. Biol.* 222(1991):581-597.
Martelli et al. "Transplants Across Human Leukocyte Antigen Barriers." *Sem. Hematol.* 39.1(2002):48-56.
Matuoka et al. "A Positive Role of Phosphatidylinositol 3-Kinase in Aging Phenotype Expression in Cultured Human Diploid Fibroblasts." *Arch. Gerontol. Geriatr.* 36(2003):203-219.
Matzner et al. "Bone Marrow Stem Cell Gene Therapy of Arylsulfatase A-Deficient Mice, Using an Arylsulfatase A Mutant that is Hypersecreted from Retrovirally Transduced Donor-Type Cells." *Hum. Gene Ther.* 12(2001):1021-1033.
McGrath et al. "Embryonic Expression and Function of the Chemokine SDF-1 and its Receptor, CSCR4." *Dev. Biol.* 213(1999):442-456.
McLaughlin et al. "Adeno-Associated Virus General Transduction Vectors: Analysis of Proviral Structures." *J. Virol.* 62.6(1988):1963-1973.
McNiece et al. "Action of Interleukin-3, G-CSF on Highly Enriched Human Hematopoetic Progenitor Cells: Synergistic Interaction of GM-CSF Plus G-CSF." *Blood.* 74(1989):110-114.
McNiece et al. "CD34+ Cell Selection from Frozen Cord Blood Products Using the Isolex 300i and CliniMACS CD34 Selection Devices." *J. Hematother.* 7(1998):457-461.
McNiece et al. "Ex vivo Expansion of Cord Blood Mononuclear Cells on Mesenchymal Stem Cells." *Cytotherapy.* 6.4(2004):311-317.
Mehta et al. "Human CD38, a Cell-Surface Protein with Multiple Functions." *FASEB J.* 10.12(1996):1408-1417.
Mehta et al. "Involvement of Retinioic Acid Receptor-Alpha-Mediated Signaling Pathway in Induction of CD38 Cell-Surface Antigen." *Blood.* 89.10(1997):3607-3614. (Abstract Only).

(56) References Cited

OTHER PUBLICATIONS

Mehta et al. "Retinoid-Mediated Signaling Pathways in CD38 Antigen Expression in Myeloid Leukemia Cells." *Leukemia and Lymphoma.* 32.5-6(1999):441-449.
Meissner et al. "Development of a Fixed Bed Bioreactor for the Expansion of Human Hematopoietic Progenitor Cells." *Cytotechnol.* 30(1999):227-234.
Mezey et al. "Turning Blood into Brain: Cells Beating Neuronal Antigens Generated in Vivo from Bone Marrow." *Science.* 290. 5497(2000):1779-1782.
Migliaccio et al. "Long-Term Generation of Colony-Forming Cells in Liquid Culture of CD34+ Cord Blood Cells in the Presence of Recombinant Human Stem Cell Factor." *Blood.* 79(1992):2620-2627.
Miller et al. "Expansion in vitro of Adult Murine Hemapoietic Stem Cells with Transplantable Lympho-Myeloid Reconstituting Ability." *PNAS.* 94(1997):13648-13653.
Miller. "Progress Toward Human Gene Therapy." *Blood.* 76.2(1990):271-278.
Mills et al. "Regulation of Retinoid-Induced Differentiation in Embryonal Carcinoma PCC4 Aza 1 R Cells: Effects of Retinoid-Receptor Selective Ligands." *Cell Growth Differ.* 7.3(1996):327-337. (Abstract Only).
Miraglia et al. "A Novel Five-Transmembrane Hematopoietic Stem Cell Antigen: Isolation, Characterization,a and Molecular Cloning." *Blood.* 90.12(1997):5013-5021.
Mood et al. "Contribution of JNK, Mek, Mos and PI-3K Signaling to GVBD in Xenopus Oocytes." *Cell Signal.* 16.5(2004):631-642. (Abstract Only).
Moore et al. "Ex Vivo Expansion of Cord Blood-Derived Stem Cells and Progenitors." *Blood Cells.* 20(1994):468-481.
Morier-Teissier et al. "Synthesis and Anti-Tumor Properties of an Anthraquinone Bisubstituted by the Copper Chelating Peptide Gly-Gly-L-His." *J. Med. Chem.* 36(1993):2084-2090. (Abstract Only).
Morimoto et al. "EDTA Induces Differentiation and Suppresses Proliferation of Promyelotic Leukemia Cell Line HL-60: Possible Participation of Zinc." *Biochem. Int.* 28.2(1992):313-321.
Morita et al. "Heterogeneity and Hierarchy within Most Primitive Hematopoietic Stem Cell Compartment." *J. Exp. Med.* 207. 6(2010):1173-1182.
Morosetti et al. "Infrequent Alterations of the RARα Gene in Acute Myelogenous Leukemias, Retinoic Acid-Resistant Acute Promyelocytic Leukemias, Myelodysplastic Syndromes, and Cell Lines." *Blood.* 87.10(1996):4399-4403.
Morrison et al. "Identification of a Lineage of Multipotent Hemaotpoietic Progenitors." *Development.* 124(1997):1929-1939.
Morrison et al. "The Long-Term Repopulating Subset of Hematopoietic Stem Cell is Deterministic and Isolatable by Phenotype." *Immunity.* 1(1994):661-673. (Abstract Only).
Morrison. "Success in Specification." *Nature.* 368.6474(1994):812-813.
Mueller et al. "Heterozygous PU.1 Mutations are Associated with Acute Myeloid Leukemia." *Blood.* 100.3(2002):998-1007.
Muench et al. "Interactions Among Colony-Stimulating Factors, IL-1β, IL-6, and Kit-Ligand in the Regulation of Primitive Murine Hematopoietic Cells." *Exp. Hematol.* 20(1992):339-349.
Mulloy et al. "Maintaining the Self-Renewal and Differentiation Potential of Human CD34+ Hematopoietic Cells Using a Single Genetic Element." *Blood.*102.13(2003):4369-4376.
Munshi et al. "Evidence for a Casual Role of CD38 Expression in Granulocytic Differentiation of Human HL-60 Cells." *J. Biol. Chem.* 277.51(2002):49453-49458.
Muramatsu et al. "Reversible Integration of the Dominant Negative Retinoid Receptor Gene for ex vivo Expansion of Hematopoietic Stem/Progenitor Cells." *Biochem. Biophys. Res. Commun.* 285. 4(2001):891-896. (Abstract Only).
Murray et al. "Modulation of Murine Lymphocyte and Macrophage Proliferation by Parental Zinc." *Clin. Exp. Immunol.* 53.3(1983):744-749.

Murray et al. "Thrombopoietin, Flt3, and Kit Ligands Together Suppress Apoptosis of Human Mobilized CD34+ Cells and Recruit Primitive CD34+Thy-1+ Cells into Rapid Division." *Exp. Hematol.* 27(1999):1019-1028.
Murry et al. "Haematopoeitic Stem Cells do not Transdifferentiate into Cardiac Myocytes in Myocardial Infarcts." *Nature.* 428(2004):664-668.
Muzyczka. "Use of Adeno-Associated Virus as a General Transduction Vector for Mammalian Cells." *Curr. Topics Microbiol. Immunol.* 158(1992):97-129.
Nagaya et al. "Intravenous Administration of Mesenchymal Stem Cells Improves Cardiac Functions in Rats with Acute Myocardial Infarction through Angiogenesis and Myogenesis." *Am. J. Physiol.* 287(2004):H2670-H2676.
Narita et al. "Cardiomyocyte Differentiation by GATA-4-Deficient Embryonic Stem Cells." *Development.* 122.19(1996):3755-3764.
Neuberger. "Generating High-Avidity Human Mabs in Mice." *Nat. Biotechnol.* 14(1996):826.
Nguyen et al. "The Search for Endogenous Activators of the Aryl Hydrocarbon Receptor." *Chem. Res. Toxicol.* 21.1(2008):102-116.
Nicolau et al. "Liposomes as Carriers for in Vivo Gene Transfer and Expression." *Meth. Enzymol.* 149(1987):157-176.
Ohishi et al. "Delta-1 Enchances Marrow and Thymus Repopulating Ability of Human CD34+CD38- Cord Blood Cells." *J. Clin. Invest.* 110.8(2002):1165-1174.
Okazaki et al. "Characteristics and Partial Purification of a Novel Cytosolic, Magnesium-Independent, Neutral Sphingomyelinase Activated in the Early Signal Transduction of 1α,25-Dihydroxyvitamin D3-Induced HL-60 Cell Differentiation." *J. Biol. Chem.* 269(1994):4070-4077.
Okuno et al. "Differential Regulation of the Human and Murine CD34 Genes in Hematopoietic Stem Cells." *PNAS.* 99.9(2002):6246-6251.
Olivares et al. "Copper as an Essential Nutrient." *Am. J. Clin. Nutr.* 63(1996):791S-796S. (Abstract Only).
Olson et al. "Tissue-Specific Homing and Expansion of Donor NK Cells in Allogeneic Bone Marrow Transplantation." *J. Immunol.* 183.5(2009):3219-3228.
Orlic et al. "Bone Marrow Cells Regenerate Infarcted Myocardium." *Nature.* 410(2001):701-705.
Orlic et al. "Exogenous Hematopoietic Stem Cells can Regenerate Infarcted Myocardium." *Circulation.* 102(2000):2672.
Orlic et al. "Mobilized Bone Marrow Cells Repair the Infarcted Heart, Improving Function and Survival." *PNAS.* 98.18(2001):10344-10349.
Orlic et al. "Transplanted Adult Bone Marrow Cells Repair Myocardial Infarcts in Mice." *Ann. N.Y. Acad. Sci.* 938(2001):221-230. (Abstract Only).
Osawa et al. "Long-Term Lymphohematopoietic Reconstitution by a Single CD34+-Low Hematopoietic Stem Cell." *Science.* 273. 5272(1996):242-245.
Ostrakhovitch et al. "Copper Ions Strongly Activate the Phosphinositide-3-Kinase/Akt Pathway Independent of the Generation of Reactive Oxygen Species." *Arch. Biochem. Biophys.* 397. 2(2002):232-239.
Pack et al. "Improved Bivalent Miniantibodies with Identical Avidity as Whole Antibodies, Produced by High Cell Density Fermentation of Escherichia coli." *Biotechnol.* 11(1993);1271-1277.
Paling et al. "Regulation of Embryonic Stem Cell Self-Renewal by Phosphoinositide 3-Kinase-Dependent Signaling." *J. Biol. Chem.* 279.46(2004):48063-48070.
Palmiter. "Regulation of Metallothionein Genes by Heavy Metals Appears to be Mediated by a Zinc-Sensitive Inhibitor that Interacts with a Constitutively Active Transcription Factor, MTF-1." *PNAS.* 91.4(1994):1219-1223.
Park et al. "Phosphastidylinositol 3-Kinase Regulates PMA-Induced Differentiation and Superoxide Production in HL-60 Cells." *Immunopharmacol. Immunotoxicol.* 2402(2002):211-226. (Abstract Only).
Pearce et al. "Interaction of the Aryl Hydrocarbon Receptor Ligand 6-Methyl-1,3,8-Trichlorodibenzofuran with Estrogen Receptor α." *Cancer Res.* 64.8(2004):2889-2897.

(56) References Cited

OTHER PUBLICATIONS

Pei et al. "Bioreactors Mediate the Effectiveness of Tissue Engineering Scaffolds." *FASB J.* 16(2002):1691-1694.
Peled et al. "Cellular Copper Content Modulates Differentiation and Self-Renewal in Cultures of Cord Blood-Derived D34+ Cells." *Brit. J. Haematol.* 116.3(2002):655-661.
Peled et al. "Chelatable Cellular Copper Modulates Differentiation and Self-Renewal of Cord Blood-Derived Hematopoietic Progenitor Cells." *Exp. Hematol.* 33(2005):1092-1100.
Peled et al. "Copper Chelators Enable Long Term CFU and CD34' Cells Expansion in Cultures Initiated with the Entire Mononuclear Cell (MNC) Fraction." *Blood.* 100.11(2002):148b. (Abstract #4076).
Peled et al. "Copper Chelators Sustain Long Term Expansion of Cord-Blood CD34+ Cultures Initiated with IL-3 and G-CSF: Late Acting, Differentiation-Inducing Cytokines." *Blood.* 96.1(2000):773a. (Abstract #3343).
Peled et al. "Dependence of Human Stem Cell Engraftment and Repopulation of NOD/SCID Mice on CXCR4." *Science.* 283(1999):845-848.
Peled et al. "Identification of a Serum-Derived Differentiation-Inducing Activity as the Copper-Binding Protein Ceruloplasmin." *Blood.* 10.A1(1998):618A-619A. (Abstract #2551).
Peled et al. "Linear Polyamine Copper Chelator Tetraethylenepentamine Augments Long-Term ex vivo Expansion of Cord Blood-Derived CD34+ Cells and Increases their Engraftment Potential in NOD/SCID Mice." *Exp. Hematol.* 32(2004):547-555.
Peled et al. "Nicotinamide Modulates Ex-Vivo Expansion of Cord Blood Derived CD34+ Cells Cultures with Cytokines and Promotes their Homing and Engraftment in SCID Mice." *Blood.* 108.11(2006):218A. (Abstract #725).
Peled et al. "Regulation of Long-Term Expansion of Hemopoietic Stem/Progenitor Cells (HPC) by Intracellular Copper Content." *Blood.* 96.11(2000):776a-777a. (Abstract #3359).
Pera. "Human Pluripotent Stem Cells: A Progress Report." *Curr. Opin. Genet. Dev.* 11(2001):595-599.
Percival et al. "Copper is Required to Maintaine Cu/Zn-Superoxide Dismutase Activity During HL-60 Cell Differentiation." *Proc. Soc. Exp. Biol. Med.* 203(1993):78-83.
Percival et al. "HL-60 Cells can be Made Copper Deficient by Incubating with Tetraethylenepentamine 1,2,3." *J. Nutr.* 122.12(1992):2424-2429.
Percival. "Copper and Immunity." *Am. J. Clin. Nutr.* 67.S5(1998):1064S-1068S.
Percival. "Neutropenia Caused by Copper Deficiency: Possible Mechanism of Action." *Nutr. Rev.* 53.3(1995):59-66.
Perrotti et al. "Overexpression of the Zinc Finger Protein MZF1 Inhibits Hematopoietic Development from Embryonic Stem Cells: Correlation with Negative Regulation of CD34 and C-MYB Promoter Activity." *Mol. Cell. Biol.* 15.11(1995):6075-6087.
Peters et al. "Long Term ex vivo Expansion of Human Fetal Liver Primitive Haematopoietic Progenitor Cells in Stroma-Free Cultures." *Brit. J. Haematol.*119(2002):792-802.
Petersen et al. "Bone Marrow as a Potential Source of Hepatic Oval Cells." *Science.* 284.5417(1999):1168-1170.
Petersen et al. "Hepatic Oval Cells Express the Hematopoietic Stem Cell Marker Thy-1 in the Rat." *Heptaol.* 27.2(1998):433-445.
Petti et al. "Complete Remission Through Blast Cell Differentiation in PLZF/RARα-Positive Acute Promyelocytic Leukemia: in vitro and in vivo Studies." *Blood.* 100.3(2002):1065-1067.
Petzer et al. "Differential Cytokine Effects on Primitive (CD34+CDe38-) Human Hematopoietic Cells: Novel Responses to Flt3-Ligand and Thrombopoietin." *J. Exp. Med.* 183(1996):2551-2558.
Petzer et al. "Self-Renewal of Primitive Human Hematopoietic Cells (Long-Term-Culture-Initiating Cells) in vitro and Their Expansion in Defined Medium." *PNAS.* 93(1996):1470-1474.

Piacibello et al. "Extensive Amplification and Self-Renewal of Human Primitive Hematopoetic Stem Cells from Cord Blood." *Blood.* 89.8(1997):2644-2653.
Pickart et al. "Growth Modulating Plasma Tripeptide may Function by Facilitating Copper Uptake into Cells." *Nature.* 288.18(1980):715-717. (Abstract Only).
Pittenger et al. "Mesenchymal Stem Cells and Their Potential as Cardiac Therapeutics." *Circ. Res.* 95.1(2004):9-20.
Podesta et al. "Cyclic ADP-Ribose Generation by CD38 Improves Human Hematopoietic Stem Cell Engraftment into NOS/SCID Mice." *FASEB J.* 17(2003):310-312.
Podesta et al. "Extracellular Cyclic ADP-Ribose Increases Intracellular Free Calcium Concentration and Stimulates Proliferation of Human Hematopoietic Progenitors." *FASEB J.* 14.5(2000):680-690.
Porter et al. "Graft-Versus-Leukemia Effect of Allogeneic Bone Marrow Transplantation and Donor Mononuclear Cell Infusions." *Cancer Treat. Res.* 77(1997):57-85. (Abstract Only).
Porter. "The Hydrolysis of Rabbit y-Globulin and Antibodies with Crystalline Papain." *Biochem. J.* 73(1959):119-126.
Presta. "Antibody Engineering." *Curr. Opin. Struct. Biol.* 2(1992):593-596.
Prockop et al. "Isolation and Characterization of Rapidly Self-Renewing Stem Cells from Cultures of Human Marrow Stromal Cells." *Cytother.* 3.5(2001):393-396.
Protti et al. "Particulate Naturally Processed Peptides Prime a Cytyotoxic Response Against Human Melanoma in Vitro." *Cancer Res.* 56(1996):1210-1213.
Psaltis et al. "Enrichment for STRO-1 Expression Enhances the Cardiovascular Paracrine Activity of Human Bone Marrow-Derived Mesenchymal Cell Populations." *J. Cell. Physiol.* 223(2010):530-540.
Puccetti et al. "AML-Associated Translocation Products Block Vitamin D3-Induced Differentiation by Sequestering the Vitamin D3 Receptor." *Cancer Res.* 62(2002):7050-7058.
Punzel et al. "The Type of Stromal Feeder Used in Limiting Dilution Assays Influences Frequency and Maintainence Assessment of Human Long-Term Culture Initiating Cells." *Leukemia.* 13(1999):92-97.
Purdy et al. "Large Volume Ex Vivo Expansion of CD34-Positive Hematopoietic Progenitor Cells for Transplantation." *J. Hematother.* 4(1995):515-525.
Purton et al. "All-Trans Retinoic Acid Delays the Differentiation of Primitive Hematopoietic Precursors (lin-c-kit+Sca-1+) While Enhancing the Terminal Maturation of Committed Granulocyte/Monocyte Progenitors." *Blood.* 94.2(1999):483-495.
Purton et al. "All-Trans Retinoic Acid Enhances the Long-Term Repopulating Activity of Cultured Hematopoietic Stem Cells." *Blood.* 95.2(2000):470-477. (Abstract Only).
Purton et al. "All-Trans Retinoic Acid Facilitates Oncoretrovirus-Mediated Transduction of Hematopoietic Repopulating Stem Cells." *J. Hamatother. Stem Cell Res.* 10.8(2001):815-825. (Abstract Only).
Quantin et al. "Adenovirus as an Expression Vector in Muscle Cells in vivo." *PNAS.* 89(1992):2581-2584.
Rajur et al. "Covalent Protein-Oligonucleotide Conjugates for Efficient Delivery of Antisense Molecules." *Bioconj. Chem.* 8.6(1997):935-940.
Ramsfjell et al. "Distinct Requirements for Optimal Growth and in vitro Expansion of Human CD34+CD38- Bone Marrow Long-Term Culture-Initiating Cells (LTC-IC), Extended LTC-IC, and Murine in vivo Long-Term Reconstituting Stem Cells." *Blood.* 94.12(1999):4093-4102.
Rankin et al. "Quantitative Studies of Inhibitors of ADP-Ribosylation In Vitro and In Vivo." *J. Biol. Chem.* 264.8(1989):4312-4317.
Ratajczak et al. "Effect of Basic (FGF-2) and Acidic (FGF-1) Fibroblast Growth Factors on Early Haemopoietic Cell Development." *Brit. J. Hematol.* 93(1996):772-782.
Ratajczak et al. "Hunt for Pluripotent Stem Cell—Regenerate Medicine Search for Almighty Cell." *J. Autoimmun.* 30(2008):151-162.

(56) References Cited

OTHER PUBLICATIONS

Reeves et al. "High Zinc Concentrations in Culture Media Affect Copper Uptake and Transport in Differentiated Human Colon Adenocarcinoma Cells." *J. Nutr.* 126.6(1996):1701-1712. (Abstract Only).
Reid et al. "Interations of Tumor Necrosis Factor with Granulocyte-Macrophade Colony-Stimulating Factor and Other Cytokines in the Regulation of Dendritic Cell Growth in vitro from Early Bipotent CD34+ Progenitors in Human Bone Marrow." *J. Immunol.* 149.8(1992):2681-2688. (Abstract Only).
Ren et al. "Inflammatory Cytokine-Induced Intercellular Adhesion Molecule-1 and Vascular Cell Adhesion Molecule-1 in Mesenchymal Stem Cells are Critical for Immunosuppression." *J. Immunol.* 184.5(2010):2321-2328.
Reya. "Regulation of Hematopoietic Stem Cell Self-Renewal." *Rec. Prog. Hormone Res.* 58(2003):283-295.
Reyes et al. "Origin of Endothelial Progenitors in Human Postnatal Bone Marrow." *J. Clin. Invest.* 109(2002):337-346.
Riechmann et al. "Reshaping Human Antibodies for Therapy." *Nature.* 332(1988):323-327.
Roach et al. "Methods for the Isolation and Maintenance of Murine Embryonic Stem Cells." *Meth. Mol. Biol.* 185(2002):1-16.
Roberts. "Mesenchymal Stem Cells." *Vox Sanguinis.* 87.S2(2004):S38-541.
Robinson et al. "Ex vivo Expansion of Umbilical Cord Blood." *Cytotherapy.* 7.3(2005):243-250.
Robinson et al. "Superior ex vivo Cord Blood Expansion Following Co-Culture with Bone Marrow-Derived Mesenchymal Stem Cells." *Bone Marrow Transplant.* 37(2006):359-366.
Rosenberg et al. "Prospective Randomized Trial of High-Dose Interleukin-2 Alone or in Conjunction with Lymphokine-Activated Killer Cells for the Treatment of Patients with Advanced Cancer." *J. Nat. Cancer Instit.* 85.8(1993):622-632.
Rosenfeld et al. "Adenovirus-Mediated Transfer of a Recombinant α1-Antitrypsin Gene to the Lung Epithelium in Vivo." *Science.* 252(1991):431-434.
Rosenfeld et al. "In Vivo Transfer of the Human Cystic Fibrosis Transmembrane Conductance Regulator Gene to the Airway Epithelium." *Cell.* 68(1992):143-155.
Ross et al. "Chelometric Indicator Titrations with the Solid-State Cupric Ion-Selective Electrode." *Anal. Chem.* 41.13(1969):1900-1902.
Rowley et al. "Isolation of CD34+ Cells from Blood Stem Cell Components Using the Baxter Isolex System." *Bone Marrow Transplant.* 21(1998):1253-1262.
Rubinstein et al. "Processing and Cryopreservation of Placental/Umbilical Cord Blood for Unrelated Bone Marrow Reconstitution." *PNAS.* 92(1995):10119-10122.
Rusten et al. "The RAR-RXR as Well as the RXR-RXR Pathway is Involved Signaling Growth Inhibition of Human CD34+ Erythroid Progenitor Cells." *Blood.* 87.5(1996):1728-1736. (Abstract Only).
Ryu et al. "Adenosine Triphosphate Induces Proliferation of Human Neural Stem Cells: Role of Calcium and p70 Ribosomal Protein S6 Kinase." *J. Neurosci. Res.* 72(2003):352-362.
Sambanis. "Encapsulated Islets in Diabetes Treatment." *Diabetes Technol. Ther.* 5.4(2003):665-668.
Sammons et al. "Mechanisms Mediating the Inhibitory Effect of All-Trans Retinoic Acid on Primitive Hematopoietic Stem Cells in Human Long-Term Bone Marrow Culture." *Stem Cells.* 18.3(2000):214-219.
Samulski et al. "Helper-Free Stocks of Recombinant Adeno-Associated Viruses: Normal Integration does not Require Viral Gene Expression." *J. Virol.* 63.9(1989):3822-3828.
Sandstrom et al. "Effects of CD34+ Cell Selection and Perfusion on Ex Vivo Expansion of Peripheral Blood Mononuclear Cells." *Blood.* 86.3(1995):958-970.
Santoro et al. "A General Purpose RNA-Cleaving DNA Enzyme." *PNAS.* 9(1997):4262-4266.
Sato et al. "In Vitro Expansion of Human Peripheral Blood CD34+ Cells." *Blood.* 82.12(1993):3600-3609.

Saulnier et al. "An Efficient Method for the Synthesis of Guanidino Prodrugs." *Bioorg. Med. Chem. Lett.* 4.16(1994):1985-1990.
Sauve et al. "Mechanism-Based Inhibitors of CD38: A Mammalian Cyclic ADP-Ribose Synthetase." *Biochem.* 41.26(2002):8455-8463.
Savouret et al. "The Aryl Hydrocarbon Receptor and its Xenobiotic Ligands: A Fundamental Trigger for Cardiovascular Diseases." *Nutr. Metab. Cardiovasc. Dis.* 13.2(2003):104-113.
Schaeffer et al. "Enzyme Inhibitors. 25." *J. Med. Chem.* 15.5(1972):456-458.
Schechter et al. "Sickle Cell Disease." *The Molecular Basis of Blood Diseases.* Stamatoyannopoulos et al., eds. Philadelphia: W.B. Saunders. (1987):179-218.
Schmetzer et al. "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro." *Hematol.* 2(1997):11-19.
Schwartz et al. "In Vitro Myelopoiesis Stimulated by Rapid Medium Exchange and Supplementation with Hematopoietic Growth Factors." *Blood.* 78.12(1991):3155-3161.
Seed. "An LFA-3 cDNA Encodes a Phospholipid-Linked Membrane Protein Homologous to its Receptor CD2." *Nature.* 329(1987):840-842.
Seeliger et al. "Human Fat-Derived Stem Cells: From Mesoderm to Hepatocyte-Like Differentiation." *Langenbecks Arch. Surg.* 394(2009):958-959. (Abstract #132).
Segev et al. "Differentiation of Human Embryonic Stem Cells into Insulin-Producing Clusters." *Stem Cells.* 22.3(2004):265-274.
Sekhar et al. "Retroviral Transduction of CD34-Enriched Hematopoietic Progenitor Cells under Serum-Free Conditions." *Hum. Gene Ther.* 7(1996):33-38.
Selden. "Optimization of Transfection." *Short Prot. Mol. Biol.* (1984):262-263.
Selden. "Transfection Using DEAE-Dextran." *Short Prot. Mol. Biol.* (1984):9.9-9.11.
Sergeant et al. "Iron and Copper Requirements for Proliferation and Differentiation of a Human Promyelocytic Leukemia Cell Line (HL-60)." *J. Cell. Physiol.* 163.3(1995):477-485.
Shimakura et al. "Murine Stromal Cell Line HESS-5 Maintains Reconstituting Ability of Ex Vivo-Generated Hematopoietic Stem Cells from Human Bone Marrow and Cytokine-Mobilized Peripheral Blood." *Stem Cells.* 18(2000):183-189.
Shimizu et al. "Treatment and Management of Wilson's Disease." *Ped. Int.* 41.4(1999):419-422. (Abstract Only).
Shioda et al. "Anti-HIV-1 and Chemotactic Activities of Human Stromal Cell-Derived Factor 1α (SDF-1α) and SDF-1β are Abolished by CD26/dipeptidyl Peptidase IV_Mediated Cleavage." *PNAS.* 95(1998):6331-6336.
Sieff et al. "Changes in Cell Surface Antigen Expression During Hemopoietic Differentiation." *Blood.* 60.3(1982):703-713.
Siena et al. "Massive ex vivo Generation of Functional Dendritic Cells from Mobilized CD34+ Blood Progenitors for Anticancer Therapy." *Exp. Hematol.* 23(1995):1463-1471.
Sigurdsson et al. "Copper Chelation Delays the Onset of Prion Disease." *J. Biol. Chem.* 278.47(2003):46199-46202.
Silvenoinen et al. "CD38 Signal Transduction in Human B Cell Precursors Rapid Induction of Tyrosine Phosphorylation, Activation of Syk Tyrosine Kinase and Phosphorylation of Phospholipase C-gamma and Phosphatidylinositol 3-Kinase." *J. Immunol.* 156.1(1996):100-107. (Abstract Only).
Simmons et al. "Identification of Stromal Cell Precursors in Human Bone Marrow by a Novel Monoclonal Antibody, STRO-1." *Blood.* 78.1(1991):55-62.
Simon et al. "Copper Deficiency and Sideroblastic Anemia Associated with Zinc Ingestion." *Am. J. Hematol.* 28(1988):181-183.
Slavin et al. "Donor Lymphocyte Infusion: The Use of Alloreactive and Tumor-Reactive Lymphocytes for Immunotherapy of Malignant and Nonmalignant Diseases in Conjunction with Allogeneic Stem Cell Transplantation." *J. Hematother. Stem Cell Res.* 11(2002):265-276.
Slavin et al. "Treatment of Leukemia by Alloreactive Lymphocytes and Nonmyeloablative Stem Cell Transplantation." *J. Clin. Immunol.* 22.2(2002):64-69.

(56) References Cited

OTHER PUBLICATIONS

Smith. "Embryo-Derived Stem Cells: Of Mice and Men." *Ann. Rev. Cell Dev. Biol.* 17(2001):435-462.
Smith. "The World According to PARP." *Trends Biochem. Sci.* 26.3(2001):174-179.
Spencer et al. "Controlling Signal Transduction with Synthetic Ligands." *Science.* 262(1993):1019-1024.
Sprangrude et al. "Purification and Characterization of Mouse Hematopoietic Stem Cells." *Science.* 241.4861(1988):58-62.
Struyf et al. "Natural Truncation of RANTES Abolishes Signaling Through the CC Chemokine Receptor CCR1 and CCR3, Impairs its Chemotactic Potency and Generates a CC Chemokine Inhibitor." *Eur. J. Immunol.* 28(1998):1262-1271.
Suda et al. "A Study of Trientine Therapy in Wilson's Disease with Neurology Symptoms." *No To Hattatsu.* 25.5(1993):429-434. (English Abstract Only).
Sylvester et al. "Stem Cells: Review and Update." *Arch. Surg.* 139(2004):93-99.
Szilvassy et al. "Differential Homing and Engraftment Properties of Hematopoietic Progenitor Cells from Murine Bone Marrow Mobilized Peripheral Blood Cells and Fetal Liver." *Blood.* 98.7(2001):2108-2115.
Takeshita et al. "Selective Stimulation by Ceramide of the Expression of the α Isoform of Retinoic Acid and Retinoid X Receptors in Osteoblastic Cells." *J. Biol. Chem.* 275.41(2000):32220-32226.
Tashiro-Itoh et al. "Metallothionein Expression and Concentrations of Copper and Zinc are Associated with Tumor Differentiation in Hepatocellular Carcinoma." *Liver.* 17(1997):300-306.
Tateishi-Yuyama et al. "Therapeutic Angiogenesis for Patients with Limb Ischemia by Autologous Transplantation of Bone-Marrow Cells: A Pilot Study and a Randomised Controlled Trial." *Lancet.* 360(2002):427-435.
Tateno et al. "Long-Term Cultivation of Adult Rat Hepatocytes that Undergo Multiple Cell Divisions and Express Normal Parenchymal Phenotypes." *Am. J. Pathol.* 148.2(1996):383-392. (Abstract Only).
*The Merck Index: An Encyclopedia of Chemicals, Drugs, and Biologicals*. Windholz et al., eds. Rahway, NJ: Merck & Co., Inc. (1983):549.
Tilesi et al. "Design and Validation of siRNAs and shRNAs." *Curr. Opin. Mol. Ther.* 11.2(2009):156-164.
Todisco et al. "CD38 Ligation Inhibits Normal and Leukemic Myelopoiesis." *Blood.* 95.2(2000):535-542. (Absract Only).
Tratschin et al. "A Human Parvovirus, Adeno-Associated Virus, as an Eucaryotic Vector: Transient Expression and Encapsidation of the Procaryotic Gene for Chloramphenicol Acetyltransferase." *Mol. Cell Biol.* 4.10(1984):2072-2081.
Tratschin et al. "Adeno-Associated Virus Vector for High-Frequency Integration, Expression, and Rescue of Genes in Mammalian Cells." *Mol. Cell. Biol.* 5.11(1985):3251-3260.
Tratschin et al. "Genetic Analysis of Adeno-Associated Virus: Properties of Deletion Mutants Constructed In Vitro and Evidence for an Adeno-Associated Virus Replication Function." *J. Virol.* 51.3(1984):611-619.
Trounson. "The Derivation and Potential Use of Human Embryonic Stem Cells." *Reprod. Fertil. Dev.* 13(2001):523-532.
Tse et al. "Angiogenesis in Ischaemic Myocardium by Intramyocardial Autologous Bone Marrow Mononuclear Cell Implantation." *Lancet.* 361(2003):47-49.
Tuba et al. "Synthesis and Structure—Activity Relationship of Neuromuscular Blocking Agents." *Curr. Med. Chem.* 9.16(2002):1507-1536.
Turnpenny et al. "Evaluating Human Embryonic Germ Cells: Concord and Conflict as Pluripotent Stem Cells." *Stem Cells.* 24(2006):212-220.
Tögel et al. "Administered Mesenchymal Stem Cells Protect Against Ischemic Acute Renal Failure Through Differentiation-Independent Mechanisms." *Am. J. Physiol. Renal Physiol.* 289(2005):F31-F42.
Uchida et al. "Direct Isolation of Human Central Nervous System Stem Cells." *PNAS.* 97.26(2000):14720-14725.
Ueda et al. "ADP-Ribosylation." *Ann. Rev. Biochem.* 54(1985):73-100.
Ueno et al. "A Novel Retinoic Acid Receptor (RAR)-Selective Antagonist Inhibits Differentiation and Apoptosis of HL-60 Cells: Implications of RARα-Mediated Signals in Myeloid Leukemic Cells." *Leuk. Res.* 22.6(1998):517-525.
Uludag et al. "Technology of Mammalian Cell Encapsulation." *Adv. Drug Deliv. Rev.* 42.1-2(2000):29-64.
Vaca et al. "Nicotinamide Induces Both Proliferation and Differentiation of Embryonic Stem Cells into Insulin-Producing Cells." *Transplant. Proc.* 35.5(2003):2021-2023.
Van Beusechem et al. "Long-Term Expression of Human Adenosine Deaminase in Rhesus Monkeys Transplanted with Retrovirus-Infected Bone-Marrow Cells." *PNAS.* 89(1992):7640-7644.
Van Epps et al. "Harvesting, Characterization, and Culture of CD34+ Cells from Human Bone Marrow, Peripheral Blood, and Cord Blood." *Blood Cells.* 20.2-3(1994):411-423.
van Poll et al. "Mesenchymal Stem Cell-Derived Molecules Directly Modulate Hepatocellular Death and Regeneration In Vitro and In Vivo." *Hepatol.* 47.5(2008):1634-1643.
Vanham et al. "Decreased Expression of the Memory Maker CD26 on Both CD4+ and CD8+ T Lymphocytes fo HIV-Infected Subjects." *J. Acq. Immune Def. Synd.* 6(1993):749-757.
Verfaillie. "Can Human Hematopoietic Stem Cells be Cultured Ex Vivo?" *Stem Cells.* 12.5(1994):466-476. (Abstract Only).
Verfaillie. "Direct Contact Between Human Primitive Hematopoietic Progenitors and Bone Marrow Stroma is not Required for Long-Term In Vitro Hematopoiesis." *Blood.* 79.11(1992):2821-2826.
Verhoeyen et al. "Reshaping Human Antibodies: Grafting an Antilysozyme Activity." *Science.* 239(1988):1534-1536.
Verlinden et al. "Interaction of Two Novel 12-Epivitamin D3 Analogs with Vitamin D3 Receptor-Retinoid X Receptor Heterodimers on Vitamin D3 Response Elements." *J. Bone Min. Res.* 16.4(2001):625-638.
Verneris et al. "The Phenotypic and Functional Characteristics of Umbilical Cord Blood and Peripheral Blood Natural Killer Cells." *Brit. J. Haematol.* 147.2(2009):185-191.
Vilensky et al. "British Anti-Lewisite (Dimercaprol): An Amazing History." *Ann. Emerg. Med.* 41.3(2003):378-383. (Abstract Only).
Virág et al. "The Therapeutic Potential of Poly(ADP-Ribose) Polymerase Inhibitors." *Pharmacol. Rev.* 54.3(2002):375-429.
Vlahos et al. "A Specific Inhibitor of Phosphatidylinostiol 3-Kinase 2-(4-Morpholinyl)-8 Phernyl-4H-1-Benzopyran-4-Oone (LY294002)." *J. Biol. Chem.* 269.7(1994):5241-5248. (Abstract Only).
Wagers et al. "Little Evidence for Developmental Plasticity of Adult Hematopoietic Stem Cells." *Science.* 297.5590(2002):2256-2259. (Abstract Only).
Wagner et al. "Replicative Sensescence of Mesenchymal Stem Cells: A Continuous and Organized Process." *PLoS One.* 3.5(2008):e2213.
Wall et al. "Inhibition of the Intrinsic NAD+ Glycohydrolase Activity of CD38 by Carbocyclic NAD Analogues." *Biochem. J.* 335.3(1998):631-636.
Walton et al. "Prediction of Antisense Oligonucleotide Binding Affinity to a Structured RNA Target." *Biotechnol. Bioeng.* 65.1(1999):1-9.
Wang et al. "In vitro Culture of Umbilical Cord Blood MNC and CD34+ Selected Cells." *Sheng Wu Gong Cheng Xue Bao.* 18.3(2002):343-347. (English Abstract Only).
Wang et al. "pH-Sensitive Immunoliposome Mediate Target-Cell-Specific Delivery and Controlled Expression of a Foreign Gene in Mouse." *PNAS.* 84(1987):7851-7855.
Wasa et al. "Copper Deficiency with Pancytopenia During Total Parental Nutrition." *JPEN.* 18.2(1994):190-192.
Weissmann. "Translating Stem and Progenitor Cell Biology to the Clinic: Barriers and Opportunities." *Science.* 287.5457(2000):1442-1446. (Abstract Only).
Wendling et al. "Retinoid X Receptor are Essential for Early Mouse Development and Placentogenesis." *PNAS.* 96.2(1999):547-551. (Abstract Only).

(56) References Cited

OTHER PUBLICATIONS

Whitlow et al. "Single-Chain Fv Proteins and Their Fusion Proteins." *Methods*. 2.2(1991):97-105.
Wick et al. "New Ways in Hepatocyte Cultures: Cell Immobilisation Technique." *ALTEX*. 14.2(1997):51-56. (Abstract Only).
Williams et al. "In Vitro Chondrogenesis of Bone Marrow-Derived Mesenchymal Stem Cells in a Photopolymerizing Hydrogel." *Tissue Eng*. 9.4(2003):679-688.
Williams et al. "Selection and Expansion of Peripheral Blood CD34+ Cells in Autologous Stem Cell Transplantation for Breast Cancer." *Blood*. 87.5(1996):1687-1691.
Williams. "Small is Beautiful: Microparticle and Nanoparticle Technology in Medical Devices." *Med. Device Technol*. 10.3(1999):6-9.
Wilson et al. "Hepatocyte-Directed Gene Transfer In Vivo Leads to Transient Improvement fo Hypercholesterolemia in Low Density Lipoprotein Receptor-Deficient Rabbits." *J. Biol. Chem*. 267. 2(1992):963-967.
Wilson et al. "Retrovirus-Mediated Transduction of Adult Hepatocytes." *PNAS*. 85(1988):3014-3018.
Wolff et al. "Direct Gene Transfer into Mouse Muscles In Vivo." *Science*. 247(1990):1465-1468.
Wondisford et al. "Cloning of the Human Thyrotropin β-Subunit Gene and Transient Expression of Biologically Active Human Thyrotropin after Gene Transfection." *Mol. Endocrinol*. 2(1988):32-39.
Wu et al. "Receptor-Mediated Gene Delivery and Expression in Vivo." *J. Biol. Chem*. 263.29(1988):14621-14624.
Wulf et al. "Somatic Stem Cell Plasticity: Current Evidence and Emerging Concepts." *Exp. Hematol*. 29(2001):1361-1370.
Xia et al. "Surface Fucosylation of Human Cord Blood Cells Augments Binding to P-Selectin and E-Selectin and Enhances Engraftment in Bone Marrow." *Blood*. 104.10(2004):3091-3096.
Yang et al. "In vitro Trans-Differentiation of Adult Hepatic Stem Cells Into Pancreatic Endocrine Hormone-Producing Cells." *PNAS*. 99.12(2002):8078-8083.
Yang et al. "Mesenchymal Stem/Progenitor Cells Developed in Cultures from UC Blood."*Cytotherapy*. 6.5(2004):476-486.
Yau et al. "Endogenous Mono-ADP-Ribosylation Mediates Smooth Muscle Cell Proliferation and Migration via Protein-Kinase Induction of C-*fos* Expression." Eur. J. Biochem. 270(2003):101-110.
Yin et al. "AC133, A Novel Marker for Human Hematopoietic Stem and Progenitor Cells." *Blood*. 90.12(1997):5002-5012.
Yla-Herttuala et al. "Gene Transfer as a Tool to Induce Therapeutic Vascular Growth." *Nat. Med*. 9.6(2003):694-701.
Yoon et al. "Clonally Expanded Novel Multipotent Stem Cells from Human Bone Marrow Regenerate Myocardium after Myocardial Infarction." *J. Clin. Invest*. 115.2(2005):326-338.
Zatloukalováet al. "β-Naphthoflavone and 3'-methoxy-4'-nitroflavone Exert Ambiguous Effect on Ah Receptor-Dependent Cell Proliferation and Gene Expression in Rat Liver 'Stem-Like' Cells." *Biochem. Pharmacol*. 73.10(2007):1622-1634.
Zhang et al. "Comparison of Mesenchymal Stem Cells from Human Placenta and Bone Marrow." *Chin. Med. J*. 117.6(2004):882-887.
Zhang et al. "Flavonoids as Aryl Hydrocarbon Receptor Agonists/Antagonists: Effect of Structure and Cell Context." *Environ. Health Persp*. 111.16(2003):1877-1882.
Zhang et al. "Human Placenta-Derived Mesenchymal Progenitor Cells Support Culture Expansion of Long-Term Culture-Initiating Cells from Cord Blood CD34+ Cells." *Exp. Hematol*. 32(2004):657-664.
Zidar et al. "Observations on the Anemia and Neutropenia of Human Copper Deficiency." *Am. J. Hematol*. 3(1977):177-185.
Zimmerman et al. "Large-Scale Selection of CD34+ Peripheral Blood Progenitors and Expansion of Neutrophil Precursors for Clinical Applications." *J. Hematother*. 5(1996):247-253.
Zocchi et al. "Ligand-Induced Internalization of CD38 Results in Intracellular Ca2+ Mobilization: Role of NAD+ Transport Across Cell Membranes." *FASEB J*. 13.2(1999):273-283. (Abstract Only).
Zon et al. "Developmental Biology of Hematopoiesis." *Blood*. 86.8(1995):2876-2891.
Zulewski et al. "Multipotent Nestin-Positive Stem Cells Isolated from Adult Pancreatic Islets Differentiate Ex Vivo into Pancreatic Endocrine, Exocrine, and Hepatic Phenotypes." *Diabetes*. 50(2001):521-533.
Diani-Moore et al. "Identification of the Aryl Hydrocarbon Receptor Target Gene TiPARP as a Mediator of Suppression of Hepatic Gluconeogenesis by 2,3,7,8-Tetrachlorodibenzo-P-Dioxin and of Nicotinamide as a Corrective Agent for This Effect", The Journal of Biological Chemistry, 285(50): 38801-38810, Published Online, (Sep. 28, 2010).
Samsonraj, Rebekah M., et al., Establishing Criteria for Human Mesenchymal Stem Cell Potency, Stem Cells 2015, 33:1878-1891.

\* cited by examiner

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 1
gcggcataga gaccgactta atttcaagag aattaagtcg gtctctatgc cgcttttttg      60
g                                                                     61

<210> SEQ ID NO 2
<211> LENGTH: 65
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 2
cgcgccaaaa aagcggcata gagaccgact taattctctt gaaattaagt cggtctctat      60
gccgc                                                                 65

<210> SEQ ID NO 3
<211> LENGTH: 61
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 3
ggcttctttg atgttgcatt aattcaagag attaatgcaa catcaaagaa gccttttttg      60
g                                                                     61

<210> SEQ ID NO 4
<211> LENGTH: 65
<212> TYPE: DNA
<213> ORGANISM: Artificial sequence
<220> FEATURE:
<223> OTHER INFORMATION: Example of an shRNA molecule which is capable
      of down-regulating the expression of AHR

<400> SEQUENCE: 4
cgcgccaaaa aaggcttctt tgatgttgca ttaatctctt gaattaatgc aacatcaaag      60
aagcc                                                                 65
```

METHODS OF CULTURING AND EXPANDING MESENCHYMAL STEM CELLS

RELATED APPLICATION

This application claims the benefit of priority under 35 USC 119(e) of U.S. Provisional Patent Application No. 61/674,428 filed Jul. 23, 2012, the contents of which are incorporated herein by reference in their entirety.

SEQUENCE LISTING STATEMENT

The contents of the text file, entitled "55110Sequence-Listing.txt", created on Jul. 18, 2013, comprising 1,683 bytes, and submitted concurrently with the filing of this application are incorporated herein by reference in their entirety.

FIELD AND BACKGROUND OF THE INVENTION

The present invention, in some embodiments thereof, relates to methods of culturing and expanding mesenchymal stem cells and isolated cell populations generated thereby.

Mesenchymal stem cells (MSCs) are non-hematopoietic cells that are capable of differentiating into specific types of mesenchymal or connective tissues including adipose, osseous, cartilaginous, elastic, neuronal, hepatic, pancreatic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues.

MSCs reside in a diverse host of tissues throughout the adult organism and possess the ability to 'regenerate' cell types specific for these tissues. Examples of these tissues include adipose tissue, umbilical cord blood, periosteum, synovial membrane, muscle, dermis, pericytes, blood, bone marrow and trabecular bone.

The multipotent character of mesenchymal stem cells make these cells an attractive therapeutic tool and candidate for transplantation, capable of playing a role in a wide range of clinical applications in the context of both cell and gene therapy strategies. Mesenchymal cells may be used to enhance hematopoietic engraftment post-transplantation, to correct inherited and acquired disorders of bone and cartilage, for implantation of prosthetic devices in connective and skeletal tissue, and as vehicles for gene therapy.

Even though MSCs multiply relatively easily in vitro, their proliferative potential and their stem cell characteristics are continuously decreased during prolonged culture. For example, it has been shown that expansion in culture leads to premature senescence (the process of aging characterized by continuous morphological and functional changes). Cells became much larger with irregular and flat shape and the cytoplasm became more granular. These senescence-associated effects are continuously acquired from the onset of in vitro culture (PLoS ONE, May 2008|Volume 3|Issue 5|e2213). As a result, the successful manufacturing for commercialization of large batches from one donor of homogenous MSCs that preserve their characteristics following expansion in culture remains a challenge.

Due to the low or absent expression of MHC molecules, especially class II on mesenchymal stem cells, these cells may be considered immune privileged, thus paving the way for allogeneic transplantation of such cells for the treatment of a wide range of disorders. Accordingly, improved methods of expanding banks of mesenchymal stem cells have become an important factor for commercializing their use.

StemRegenin 1 (SR1), a purine derivative, has been identified in an unbiased screen to promote the ex vivo expansion of CD34+ cells. Mechanistic studies show that SR1 acts by antagonizing the aryl hydrocarbon receptor (AhR) expansion [Boitano et al. 2010 Science 329(5997): 1345-1348].

U.S. Patent Application No. 20100183564 discloses the use of aryl hydrocarbon receptor antagonists for hematopoietic stem cell expansion. U.S. Patent Application No. 20100183564 does not suggest or mention the use of aryl hydrocarbon receptor antagonists for non-hemaptopoietic stem cell expansion.

Additional background art includes WO 03/062369, U.S. Patent Application No. 20050260748 and Farre et al., Growth Factors, 2007 April; 25(2):71-6.

SUMMARY OF THE INVENTION

According to an aspect of some embodiments of the present invention a method of culturing mesenchymal stem cells (MSCs) comprising culturing a population of the MSCs in a medium comprising an aryl hydrocarbon receptor antagonist, thereby culturing MSCs.

According to an aspect of some embodiments of the present invention a method of expanding a population of mesenchymal stem cells, the method comprising culturing a seeded population of mesenchymal stem cells for a period of time sufficient for cell expansion, wherein the culturing is in a medium comprising an aryl hydrocarbon receptor antagonist, thereby generating an expanded population of mesenchymal stem cells.

According to an aspect of some embodiments of the present invention a method of generating cells useful for transplantation into a subject, the method comprising:

(a) culturing mesenchymal stem cells according to the method above-described to generate a population of cultured mesenchymal stem cells; and (b) contacting the population of cultured mesenchymal stem cells with a differentiating agent, thereby generating cells useful for transplantation into a subject.

According to an aspect of some embodiments of the present invention a method of generating cells useful for transplantation, the method comprising:

(a) expanding mesenchymal stem cells according to the method above-described; and (b) contacting the mesenchymal stem cells with a differentiating agent, thereby generating cells useful for transplantation.

According to an aspect of some embodiments of the present invention a cell culture, comprising mesenchymal stem cells and a medium which comprises an aryl hydrocarbon receptor antagonist.

According to some embodiments of the invention, the medium further comprises at least one of nicotinamide and a growth factor.

According to some embodiments of the invention, the mesenchymal stem cells are derived from a tissue selected from the group consisting of bone marrow, adipose tissue, placenta and umbilical cord blood.

According to some embodiments of the invention, the aryl hydrocarbon receptor antagonist comprises wherein the AHR antagonist is 4-(2-(2-(benzo[b]thiophen-3-yl)-9-isopropyl-9H-purin-6-ylamino)ethyl)phenol (StemRegenin 1, SR1).

According to some embodiments of the invention, a concentration of the SR1 in the medium is at a range of 100-1000 nM.

According to some embodiments of the invention, a concentration of the SR1 in the medium is at a range of 100-500 nM.

According to some embodiments of the invention, the medium further comprises nicotinamide.

According to some embodiments of the invention, a concentration of the nicotinamide in the medium is at a range of 1-20 mM.

According to some embodiments of the invention, the medium further comprises a growth factor.

According to some embodiments of the invention, the growth factor comprises FGF-4.

According to some embodiments of the invention, a calcium concentration of the medium is greater than 1.8 mM.

According to some embodiments of the invention, the nicotinamide is selected from the group consisting of nicotinamide, a nicotinamide analog, a nicotinamide metabolite, a nicotinamide analog metabolite and derivatives thereof.

According to some embodiments of the invention, the culturing is effected on a plastic surface.

According to some embodiments of the invention, the population of MSCs is comprised in a heterogeneous population of cells.

According to some embodiments of the invention, at least 70% of the heterogeneous population of cells are MSCs.

According to some embodiments of the invention, the culturing is effected for at least 1 week.

According to some embodiments of the invention, the culturing is effected for at least 3 passages.

According to some embodiments of the invention, the medium is devoid of platelet derived growth factor (PDGF).

According to some embodiments of the invention, the expanding is effected under conditions that do not induce differentiation of the mesenchymal stem cells.

According to some embodiments of the invention, the seeded population of mesenchymal stem cells was seeded in an absence of nicotinamide.

According to some embodiments of the invention, the seeded population of mesenchymal stem cells was seeded in a presence of nicotinamide.

According to some embodiments of the invention, the differentiation agent comprises a growth factor.

According to some embodiments of the invention, the differentiation agent comprises a polynucleotide which encodes the differentiation agent.

According to some embodiments of the invention, the polynucleotide encodes bone morphogenic protein 2 (BMP2).

According to some embodiments of the invention, the AHR antagonist is represented by Formula I:

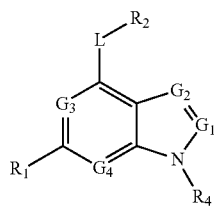

Formula I wherein:
$G_1$ is selected from N and $CR_3$;
$R_3$ is selected from hydrogen, $C_{1-4}$alkyl and biphenyl;
$G_2$, $G_3$ and $G_4$ are each independently selected from —CH— and N; with the proviso that at least one of $G_3$ and $G_4$ is N; and with the proviso that $G_1$ and $G_2$ are not both N;

L is selected from a substituted or unsubstituted alkylamino, a substituted or unsubstituted amino or a substituted or unsubstituted alkyl;

$R_1$ is selected from hydrogen, a substituted or unsubstituted aryl and a substituted or unsubstituted heteroaryl; with the proviso that $R_1$ and $R_3$ are not both hydrogen;

$R_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, a substituted or unsubstituted aryl and a substituted or unsubstituted heteroaryl; and $R_4$ is selected from a substituted or unsubstituted $C_{1-10}$alkyl, a substituted or unsubstituted $C_{1-10}$alkenyl, a substituted or unsubstituted cycloalkyl, a substituted or unsubstituted aryl, a substituted or unsubstituted alkaryl, a substituted or unsubstituted heteroalicyclic and a substituted or unsubstituted heteroaryl.

According to some embodiments of the invention, L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—, wherein $R_{5a}$ and $R_{5b}$ are independently selected from hydrogen and $C_{1-4}$alkyl;

According to some embodiments of the invention, $R_1$ is selected from phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl), each being optionally substituted by 1 to 3 substituents selected from cyano, hydroxy, $C_{1-4}$alkyl, $C_{1-4}$alkoxy, halo, halo-substituted-$C_{1-4}$alkyl, halo-substituted-$C_{1-4}$alkoxy, amino, —C(O)R$_{8a}$, —S(O)$_{0-2}$R$_{8a}$, —C(O)OR$_{8a}$ and —C(O)NR$_{8a}$R$_{8b}$, wherein each of $R_{8a}$ and $R_{8b}$ can independently be hydrogen or $C_{1-4}$alkyl.

According to some embodiments of the invention, $R_4$ is selected from $C_{1-10}$alkyl, prop-1-en-2-yl, cyclohexyl, cyclopropyl, phenyl, benzyl, benzhydryl, 2-(2-oxopyrrolidin-1-yl)ethyl, oxetan-3-yl, tetrahydro-2H-pyran-3-yl, tetrahydro-2H-pyran-4-yl, tetrahydrofuran-3-yl, (4-pentylphenyl)(phenyl)methyl and 1-(1-(2-oxo-6,9,12-trioxa-3-azatetradecan-14-yl)-1H-1,2,3-triazol-4-yl)ethyl, each being optionally substituted with 1 to 3 substituents independently selected from hydroxy, $C_{1-4}$alkyl and halo-substituted-$C_{1-4}$alkyl.

According to some embodiments of the invention, $R_2$ is selected from phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl, each being optionally substituted with 1 to 3 substituents selected from hydroxy, halo, methyl, methoxy, amino, —O(CH$_2$)$_n$NR$_{7a}$R$_{7b}$, —S(O)$_2$NR$_{7a}$R$_{7b}$, —OS(O)$_2$NR$_{7a}$R$_{7b}$ and —NR$_{7a}$S(O)$_2$R$_{7b}$, wherein each of $R_{1a}$ and $R_{1b}$ is independently hydrogen or $C_{1-4}$alkyl.

According to some embodiments of the invention, $G_1$ is $CR_3$, and $G_2$, $G_3$ and $G_4$ are each N, the antagonist of the AHR being represented by Formula Ia:

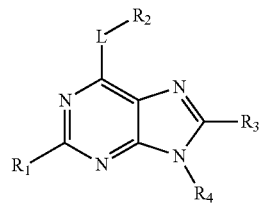

Formula Ia wherein $R_1$-$R_4$ and L are as defined.

According to some embodiments of the invention, $G_2$ is CH, and $G_1$, $G_3$ and $G_4$ are each N, the antagonist of AHR is represented by Formula Ib:

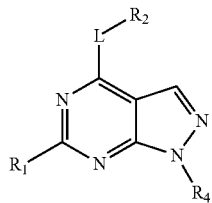

Formula Ib wherein $R_1$, $R_2$, $R_4$ and L are as defined above.

According to some embodiments of the invention, $G_1$ is $CR_3$, $G_2$ and $G_4$ are each N, and $G_3$ is CH, the AHR antagonist being represented by Formula Ic:

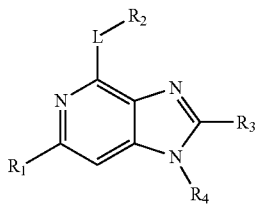

Formula Ic wherein $R_1$-$R_4$ and L are as defined.

According to some embodiments of the invention, $G_1$ is $CR_3$, $G_2$ and $G_3$ are each N, and $G_4$ is CH, the AHR antagonist being represented by Formula Id:

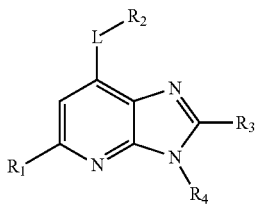

Formula Id wherein $R_1$-$R_4$ and L are as defined above.

According to some embodiments of the invention, $G_1$ is $CR_3$, $G_3$ and $G_4$ are each N, and $G_2$ is CH, the AHR antagonist being represented by Formula Ie:

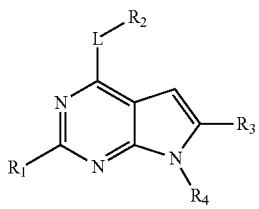

Formula Ie wherein $R_1$-$R_4$ and L are as defined above.

According to some embodiments of the invention, L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—, wherein $R_{5a}$ and $R_{5b}$ are each independently selected from hydrogen and $C_{1-4}$alkyl.

According to some embodiments of the invention, $R_1$ is selected from hydrogen and an aryl or heteroaryl selected from phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl), wherein the aryl or heteroaryl of $R_1$ is optionally substituted by 1 to 3 substituents independently selected from cyano, hydroxy, $C_{1-4}$alkyl, $C_{1-4}$alkoxy, halo, halo-substituted-$C_{1-4}$alkyl, —$S(O)_{0-2}R_{8a}$ and —$C(O)OR_{8a}$, wherein $R_{8a}$ and $R_{8b}$ are independently selected from hydrogen and $C_{1-4}$alkyl; with the proviso that $R_1$ and $R_3$, if both present, are not both hydrogen.

According to some embodiments of the invention, $R_2$ is selected from —$NR_{6a}C(O)NR_{6b}R_{6c}$, and an aryl, heteroaryl or heteroalicyclic selected from 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl, wherein $R_{6a}$, $R_{6b}$ and $R_{6c}$ are independently selected from hydrogen and $C_{1-4}$alkyl, and wherein each of the aryl, heteroaryl and heteroalicyclic of $R_2$ is independently optionally substituted with 1 to 3 substituents independently selected from hydroxy, halo, methoxy, amino, —$OS(O)_2NR_{7a}R_{7b}$ and —$NR_{7a}S(O)_2R_{7b}$, wherein $R_{7a}$ and $R_{7b}$ are independently selected from hydrogen and $C_{1-4}$alkyl.

According to some embodiments of the invention,
$R_3$, when present, is selected from hydrogen, $C_{1-4}$alkyl and biphenyl; and $R_4$ is selected from a substituted or unsubstituted alkyl or alkenyl.

According to some embodiments of the invention, the alkyl or alkenyl is selected from isopropyl, methyl, ethyl, prop-1-en-2-yl, isobutyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl), cycloalkyl (e.g., cyclohexyl), aryl (e.g., phenyl), alkaryl (e.g., benzyl and benhydryl), and a heteroalicyclic or heteroaryl (e.g., 2-(2-oxopyrrolidin-1-yl)ethyl, oxetan-3-yl, oxetan-2-yl, tetrahydro-2H-pyran-2-yl, tetrahydrofuran-3-yl); each of the alkyl or alkenyl being optionally substituted with 1 to 3 substituents independently selected from $C_{1-4}$alkyl and halo-substituted-$C_{1-4}$alkyl.

According to some embodiments of the invention, L is —$NR_{5a}(CH_2)_{1-3}$.

According to some embodiments of the invention, the AHR antagonist is represented by the Formula Ia.

According to some embodiments of the invention, L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH(CH_3)CH_2$—, —$(CH_2)_3$—, —$CH_2OCH_2$—, —$CH_2NR_{5a}CH_2$—, —$NR_{5a}C(O)CH_2$— and —$NR_{5a}Y$—, wherein $R_{5a}$ and $R_{5b}$ are independently selected from hydrogen and methyl; and Y is selected from isoxazole and 1,3,4-oxadiazole.

According to some embodiments of the invention, R₃ is hydrogen, R₁ is benzothipohene, and L is ethylamino, such that the AHR antagonist is represented by Formula If:

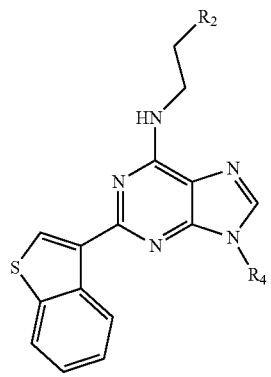

Formula If wherein:
R₂ is selected from a substituted or unsubstituted heteroaryl and a substituted or unsubstituted aryl; and
R₄ is selected from branched alkyl, alkaryl, a heteroalicyclic.

According to some embodiments of the invention, R₂ is selected from 1H-indol-3-yl and phenyl, each being optionally substituted by hydroxyl.

According to some embodiments of the invention, R₄ is selected from isopropyl, sec-butyl, benzhydryl, and nonan-2-yl, oxetan-3-yl and tetrahydrofuran-3-yl.

According to some embodiments of the invention, R₃ is hydrogen, R₁ is a substituted or unsubstituted pyridine-3-yl, and L is ethylamino, such that the AHR antagonist is represented by Formula Ig:

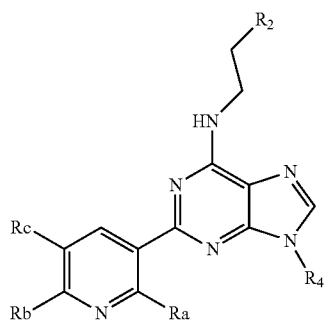

Formula Ig wherein:
R₂ is selected from a substituted or unsubstituted aryl and a substituted or unsubstituted heteroaryl;
R₄ is selected from branched alkyl, alkaryl, a heteroalicyclic; and
Ra, Rb and Rc are independently selected from hydrogen, cyano, methyl, halo, —SO₂CH₃ and trifluoromethyl.

According to some embodiments of the invention, R₂ is selected from 1H-pyrrolo[2,3-b]pyridin-3-yl, 1H-indol-3-yl and phenyl, each being optionally substituted with 1 to 2 subsituents independently selected from halo, methyl, hydroxy and methoxy.

According to some embodiments of the invention, R₄ is selected from isopropyl, sec-butyl, benzhydryl, and nonan-2-yl, oxetan-3-yl and tetrahydrofuran-3-yl.

According to some embodiments of the invention, the AHR antagonist is selected from:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-yl amino)ethyl)phenol;
4-(2-(9-isopropyl-2-(thiophen-2-yl)-9H-purin-6-ylamino)ethyl)phenol;
4-(2-(2-(benzo[b]thiophen-3-yl)-9-(4-(trifluoromethyl)benzyl)-9H-purin-6-yl amino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino) ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[b]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino)ethyl)phenol;
4-(2-(9-isopropyl-2-(pyridin-3-yl)-9H-purin-6-ylamino)ethyl)phenol;
4-(2-(9-isopropyl-2-phenyl-9H-purin-6-ylamino)ethyl)phenol;
4-(2-(9-isopropyl-2-(thiophen-3-yl)-9H-purin-6-ylamino)ethyl)phenol;
4-(2-(2-(furan-3-yl)-9-isopropyl-9H-purin-6-ylamino)ethyl)phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;
4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate;
N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino) ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino) ethyl)phenol;

4-(2-(2-(1H-imidazol-1-yl)-9-isopropyl-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methyl sulfonyl)pyridin-3-yl)-9H-purin-6-ylamino) ethyl)phenol;
4-(2-(9-isopropyl-2-(5-methylpyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(1-methyl-1H-pyrazol-4-yl)-9H-purin-6-ylamino)ethyl)phenol;
4-(2-(9-isopropyl-2-(pyridin-3-yl)-9H-purin-6-ylamino)ethyl)-2-methoxy phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-{2-[(3-methyl-1H-1,2,4-triazol-5-yl)sulfanyl]ethyl}-9-(propan-2-yl)-2-(pyridin-3-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl) urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methanesulfonamide;
4-(2-(2-(pyridin-3-yl)-9-(tetrahydrofuran-3-yl)-9H-purin-6-ylamino)ethyl)-phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
5-(6-(4-hydroxyphenethylamino)-9-isopropyl-9H-purin-2-yl)-N-methylnicotin-amide;
4-(2-(9-(1-hydroxypropan-2-yl)-2-(pyridin-3-yl)-9H-purin-6-ylamino)-ethyl)phenol;
4-(2-(9-isopropyl-2-(pyridin-3-yl)-9H-purin-6-ylamino)ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol;
4-(2-(9-isopropyl-2-(thiazol-5-yl)-9H-purin-6-ylamino)ethyl)phenol;
4-(2-(2-(1H-benzo[d]imidazol-1-yl)-9-isopropyl-9H-purin-6-ylamino)ethyl)-phenol;
4-(2-(2-(2,4-dimethyl-1H-imidazol-1-yl)-9-isopropyl-9H-purin-6-ylamino) ethyl)phenol;
4-(2-(9-isopropyl-2-(2-methyl-1H-imidazol-1-yl)-9H-purin-6-ylamino)ethyl)-phenol;
5-(9-sec-butyl-6-(4-hydroxy-3-methylphenethylamino)-9H-purin-2-yl)-nicotinitrile;
N-(2-(1H-pyrrolo[2,3-b]pyridin-5-yl)ethyl)-9-isopropyl-2-(pyridin-3-yl)-9-H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino) ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl) ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
4-(2-(6-(benzo[b]thiophen-3-yl)-1-isopropyl-1H-pyrazolo[3,4-d]pyrimidin-4-yl amino)ethyl)phenol;
(R)-4-(2-(2-(5-fluoropyridin-3-yl)-9-(tetrahydrofuran-3-yl)-9H-purin-6-yl-amino)ethyl)phenol);
4-(2-(9-isopropyl-2-(pyridin-3-yl)-9H-purin-6-ylamino)ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
4-(2-(2-(5-fluoropyridin-3-yl)-7-isopropyl-7H-pyrrolo[2,3-d]pyrimidin-4-yl amino)ethyl)phenol;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino)ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;

4-(2-(9-isopropyl-2-(pyridin-3-yl)-9H-purin-6-ylamino) ethyl)-2-methylphenol;

4-(2-(2-(benzo[b]thiophen-3-yl)-9-(oxetan-3-yl)-9H-purin-6-ylamino)ethyl)-phenol;

(S)-4-(2-(2-(benzo[b]thiophen-3-yl)-9-(tetrahydrofuran-3-yl)-9H-purin-6-yl amino)ethyl)phenol;

(R)-4-(2-(2-(benzo[b]thiophen-3-yl)-9-(tetrahydrofuran-3-yl)-9H-purin-6-yl amino)ethyl)phenol;

2-(6-(2-(1H-indol-3-yl)ethylamino)-2-(5-fluoropyridin-3-yl)-9H-purin-9-yl)propan-1-ol;

(R)-2-(6-(2-(1H-indol-3-yl)ethylamino)-2-(5-fluoropyridin-3-yl)-9H-purin-9-yl)propan-1-ol;

(S)-2-(6-(2-(1H-indol-3-yl)ethylamino)-2-(5-fluoropyridin-3-yl)-9H-purin-9-yl)propan-1-ol;

(R)—N-(2-(1H-indol-3-yl)ethyl)-2-(5-fluoropyridin-3-yl)-9-(tetrahydrofuran-3-yl)-9H-purin-6-amine;

4-(2-(2-(3H-imidazo[4,5-b]pyridin-3-yl)-9-isopropyl-9H-purin-6-ylamino) ethyl)phenol;

4-(2-(2-(1H-imidazo[4,5-b]pyridin-1-yl)-9-isopropyl-9H-purin-6-ylamino) ethyl)phenol;

4-(2-(6-(5-fluoropyridin-3-yl)-1-isopropyl-1H-imidazo[4,5-c]pyridin-4-yl amino)ethyl)phenol;

4-(2-(2-(4,5-dimethyl-1H-imidazol-1-yl)-9-isopropyl-9H-purin-6-ylamino) ethyl)phenol;

2-(5-fluoropyridin-3-yl)-9-isopropyl-N-(2-(pyridin-3-yl) ethyl)-9H-purin-6-amine;

4-(2-(2-(5-fluoropyridin-3-yl)-9-isopropyl-9H-purin-6-ylamino)-1-hydroxy ethyl)phenol;

2-(5-fluoropyridin-3-yl)-9-isopropyl-N-(2-(6-methoxy-1H-indol-3-yl) ethyl)-9H-purin-6-amine;

N-(2-(1H-indol-3-yl)ethyl)-2-(5-fluoropyridin-3-yl)-9-isopropyl-9H-purin-6-amine;

2-(5-fluoropyridin-3-yl)-9-isopropyl-N-(2-(5-methoxy-1H-indol-3-yl)ethyl)-9H-purin-6-amine;

N-(2-(1H-indol-3-yl)ethyl)-2-(5-fluoropyridin-3-yl)-9-(prop-1-en-2-yl)-9H-purin-6-amine;

5-(2-(2-(5-fluoropyridin-3-yl)-9-isopropyl-9H-purin-6-ylamino)ethyl)pyridin-2-ol;

N-(2-(1H-pyrrolo[2,3-b]pyridin-3-yl)ethyl)-2-(5-fluoropyridin-3-yl)-9-isopropyl-9H-purin-6-amine;

N-(2-(6-(2-(diethylamino)ethoxy)-1H-indol-3-yl)ethyl)-2-(5-fluoropyridin-3-yl)-9-isopropyl-9H-purin-6-amine;

4-(2-(5-(5-fluoropyridin-3-yl)-3-isopropyl-3H-imidazo[4,5-b]pyridin-7-yl amino)ethyl)phenol;

N-(2-(1H-indol-3-yl)ethyl)-9-sec-butyl-2-(2-methyl-1H-imidazol-1-yl)-9H-purin-6-amine;

4-(2-(2-(2-ethyl-1H-imidazol-1-yl)-9-isopropyl-9H-purin-6-ylamino)ethyl)phenol;

4-(2-(9-isopropyl-2-(2-propyl-1H-imidazol-1-yl)-9H-purin-6-ylamino)-ethyl)phenol;

3-(2-(2-(5-fluoropyridin-3-yl)-9-isopropyl-9H-purin-6-ylamino)ethyl)-1H-indol-6-ol;

N-(2-(1H-indol-3-yl)ethyl)-9-isopropyl-2-(5-methylpyridin-3-yl)-9H-purin-6-amine;

N-(2-(1H-indol-3-yl)ethyl)-9-isopropyl-2-(2-methyl-1H-imidazol-1-yl)-9H-purin-6-amine;

2-(5-fluoropyridin-3-yl)-9-isopropyl-N-(2-(7-methyl-1H-indol-3-yl)ethyl)-9H-purin-6-amine;

N-(2-(1H-indol-3-yl)ethyl)-2-(5-fluoropyridin-3-yl)-9-(oxetan-3-yl)-9H-purin-6-amine;

N-(2-(1H-indol-3-yl)ethyl)-2-(5-methylpyridin-3-yl)-9-(oxetan-3-yl)-9H-purin-6-amine;

N-(2-(6-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(6-methyl-1H-indol-3-yl)ethyl)-9H-purin-6-amine;

2-(5-fluoropyridin-3-yl)-9-isopropyl-N-(2-(2-methyl-1H-indol-3-yl)ethyl)-9H-purin-6-amine;

N-(2-(4-fluoro-1H-indol-3-yl)ethyl)-2-(5-fluoropyridin-3-yl)-9-isopropyl-9H-purin-6-amine;

N-(2-(7-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(4-methyl-1H-indol-3-yl)ethyl)-9H-purin-6-amine;

4-(2-(2-(benzo[b]thiophen-3-yl)-7-isopropyl-7H-pyrrolo[2,3-d]pyrimidin-4-yl amino)ethyl)phenol;

9-isopropyl-2-(pyridin-3-yl)-N-(2-(pyridin-4-yl)ethyl)-9H-purin-6-amine;

N-(2-(1H-pyrrolo[2,3-b]pyridin-5-yl)ethyl)-9-isopropyl-2-(pyridin-3-yl)-9H-purin-6-amine;

4-(2-(2-(5-fluoropyridin-3-yl)-9-(1-hydroxypropan-2-yl)-9H-purin-6-ylamino)ethyl)-2-methylphenol;

4-(2-(2-(benzo[b]thiophen-3-yl)-9-cyclohexyl-9H-purin-6-ylamino)ethyl)phenol;

4-(2-(9-isopropyl-2-(thiophen-3-yl)-9H-purin-6-ylamino) ethyl)phenol; and 1-(2-(2-(benzo[b]thiophen-3-yl)-6-(4-hydroxyphenethyl-amino)-9H-purin-9-yl) ethyl)pyrrolidin-2-one.

According to an aspect of some embodiments of the present invention an isolated population of mesenchymal stem cells generated according to the method described above.

According to an aspect of some embodiments of the present invention an isolated population of mesenchymal stem cells generated according to the method described above.

According to some embodiments of the invention, the isolated population of mesenchymal stem cells is substantially homogeneous.

According to some embodiments of the invention, the isolated population of mesenchymal stem cells has a doubling time which is shorter than in the absence of the aryl hydrocarbon receptor antagonist.

According to some embodiments of the invention, in the isolated population of mesenchymal stem cells more than 40% of the cells express CD106 following at least two passages in culture.

According to an aspect of some embodiments of the present invention a method of treating a disease or disorder, the method comprising transplanting to a subject in need thereof a therapeutically effective amount of the isolated population of cells, thereby treating the disease or disorder.

According to some embodiments of the invention, the disease or disorder is selected from the group consisting of a bone or cartilage disease, a neurodegenerative disease, a cardiac disease, a hepatic disease, cancer, nerve damage, autoimmune disease, GvHD, wound healing and tissue regeneration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying In the drawings.

DESCRIPTION OF SPECIFIC EMBODIMENTS OF THE INVENTION

Figure 1:
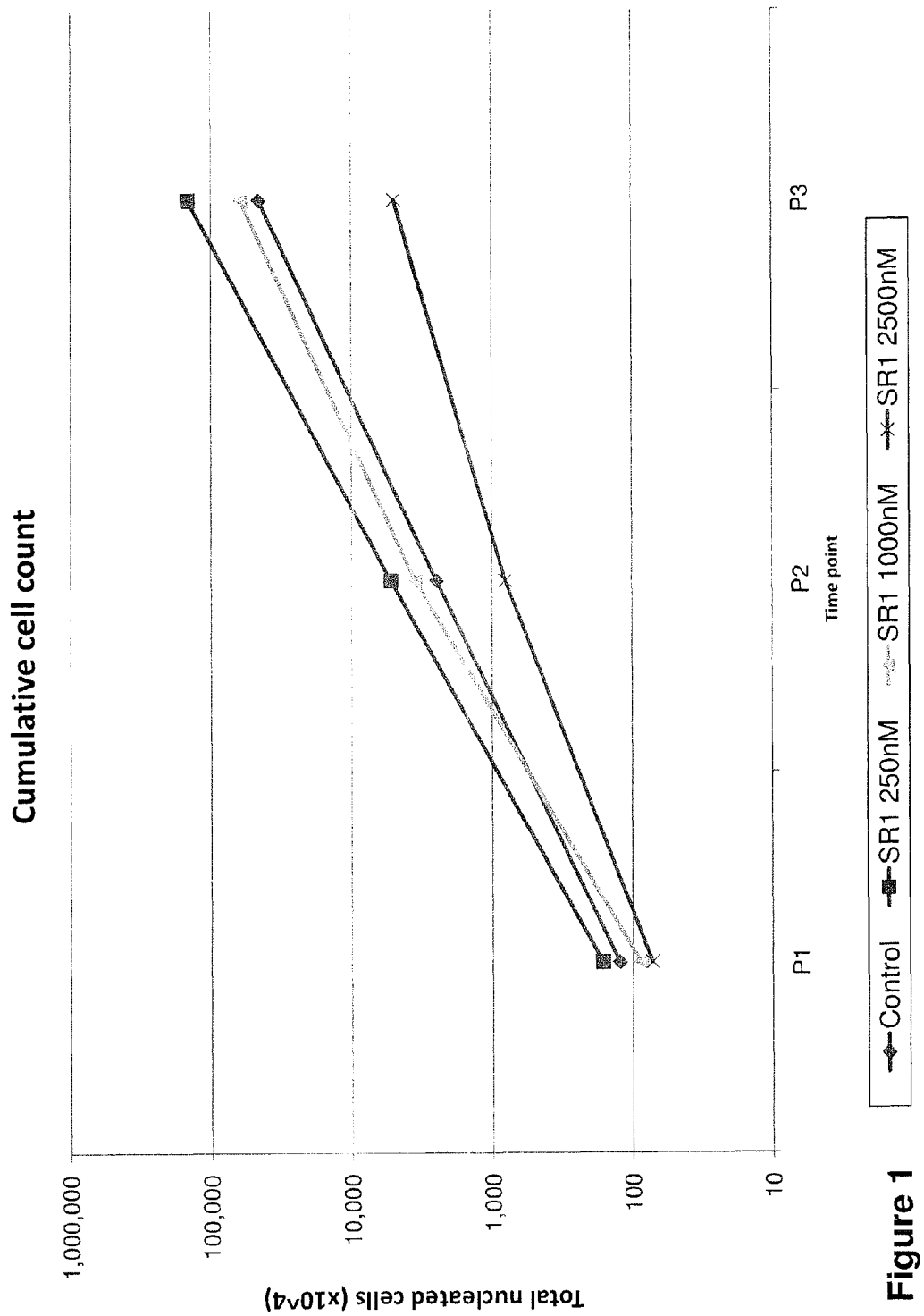
FIG. 1 is a graph showing cumulative count of mesenchymal stem cells in the absence or presence of SR1 at the indicated concentrations.

The present invention, in some embodiments thereof, relates to methods of culturing and expanding mesenchymal stem cells and isolated cell populations generated thereby.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The multipotent character of mesenchymal stem cells (MSCs) make these cells an attractive therapeutic tool and candidate for transplantation, capable of playing a role in a wide range of clinical applications in the context of both cell and gene therapy strategies. For example, mesenchymal stem cells may be used to enhance hematopoietic engraftment post-transplantation, to aid in tissue re-generation, to promote wound healing and to correct for a myriad of other inherited and acquired disorders. Efficient mesenchymal stem cell expansion protocols that do not have deleterious effects on the differentiation potential and target tissue engraftment potential of the cells are crucial to the success of any of these strategies.

In addition, MSCs are attractive for clinical therapy in regenerative medicine and inflammatory conditions due to their ability to differentiate, provide trophic support, and modulate the innate immune response. The therapeutic potential of MSC is being tested in multiple clinical trials for indications such as bone and cartilage repair, cardiac regeneration, critical limb ischemia, acute ischemic conditions, diabetes, Crohn's disease and graft vs host disease.

MSCs are immune-privileged and can be transplanted without the need for HLA matching between the donor and the recipient and therefore can be manufactured at large scale and marketed as an off-the-shelf cell product. The success of large scale batch production from one donor is highly dependent on donor and serum selection, the potential of seeded cells for prolonged expansion in culture and the duration of the manufacturing. Even though MSC multiply relatively easily in vitro, their proliferative potential is continuously decreased and their doubling time increases during culture. As a result, the successful manufacturing for commercialization of large batches of homogenous MSCs from one donor remains a challenge.

Whilst studying the effect of the aryl hydrocarbon receptor antagonist, SR1, on mesenchymal stem cell expansion, the present inventors have surprisingly uncovered that MSCs cultured with SR1 proliferate more rapidly (FIGS. 1 and 2) than in the absence of SR1. Furthermore, the doubling time (see FIG. 3) of the cells is decreased and the cultures reach confluence in a substantially shorter period of time. Further, the culture quality is maintained in the presence of SR1, namely, the cultures comprise high levels of true mesenchymal stem cells as evidenced by surface marker expression (CD105$^+$/CD45$^-$ and CD106$^+$, see FIGS. 4 and 5). In addition, SR1 increase the fraction of CD106+ cells within the expanded cell population. CD106/Vascular cell adhesion molecule-1 (VCAM1) is critical for MSC-mediated Immunosuppression and neovascularization ((J Clin Invest. 2005; 115(6):1542), The Journal of Immunology, 2010, 184: 2321).

These findings suggest that SR1 and other aryl hydrocarbon receptor antagonists can be used in the differentiation-less expansion and culturing of mesenchymal stem cells.

Thus, according to one aspect of the present invention there is provided a method of culturing mesenchymal stem cells (MSCs) comprising culturing a population of the MSCs in a medium comprising an aryl hydrocarbon receptor antagonist, thereby culturing MSCs.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage, (e.g., adipose, osseous, cartilaginous, elastic and fibrous connective tissues, myoblasts, neural cells) as well as to tissues other than those originating in the embryonic mesoderm depending upon various influences from bioactive factors such as cytokines.

MSC cultures utilized by some embodiments of the invention preferably include three groups of cells which are defined by their morphological features: small and agranular cells (RS-1), small and granular cells (RS-2) and large and moderately granular cells (adult MSCs). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) may be dimly positive for CD31 and/or CD38 markers. In addition, mature MSCs may be dimly positive for the hematopoietic stem cell marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

According to a preferred embodiment of this aspect of the present invention, the mesenchymal stem cells are human.

According to another embodiment of this aspect of the present invention, the mesenchymal stem cells are isolated from newborn humans.

Mesenchymal stem cells may be isolated from various tissues including but not limited to bone marrow, peripheral blood, blood, placenta (e.g. fetal side of the placenta or the maternal side of the placenta or combination of both), cord blood, umbilical cord, amniotic fluid, placenta and from adipose tissue.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887] and U.S. Patent Application 2003/0235563. Methods of isolating and culturing adipose tissue, placental and cord blood mesenchymal stem cells are described by Kern et al [Stem Cells, 2006; 24:1294-1301].

Bone marrow can be isolated from the iliac crest of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, α medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO).

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

As mentioned, the method is effected by culturing (i.e. ex vivo or in vitro) the mesenchymal stem cells in a medium comprising an aryl hydrocarbon receptor antagonist.

According to this aspect of the present invention, the cells are cultured under conditions that do not induce differentiation (e.g. in the absence of differentiation factors or in the presence of a non-differentiating amount of differentiating factors).

The present invention contemplates directly culturing mesenchymal stem cells following isolation from their source or culturing populations of cells that have been pre-selected for mesenchymal stem cells. Thus, the present invention contemplates culturing both heterogeneous populations of cells which comprise the MSCs and more homogeneous populations of cells, which have been enriched for MSCs, wherein more than 70%, more than 80%, more than 90% or more than 95%, more than 98% thereof are MSCs. Also, contemplated is the enriching for MSCs concomitant with the culturing as further described herein below.

It will be appreciated that the composition of the heterogeneous population of cells will be dependent on the source of the cells. Thus, for example, if the placenta is selected as the cell source, the heterogeneous population of cells will comprise placental cells as well as mesenchymal stem cells. If the bone marrow is selected as the cell source, the heterogeneous population of cells will comprise blood cells.

According to one method, the population of cells are cultured (in vitro or ex vivo) on polystyrene plastic surfaces (e.g. in a flask) so as to enrich for mesenchymal stem cells by removing non-adherent cells (i.e. non-mesenchymal stem cells). This method of enriching for MSCs may be effected prior to the culturing in the medium which comprises the aryl hydrocarbon receptor antagonist, concomitant with the culturing in the medium which comprises the aryl hydrocarbon receptor antagonist and/or following the culturing in the medium which comprises the aryl hydrocarbon receptor antagonist.

Other methods of selecting for MSCs are known in the art including for example positive selection against mesenchymal stem cell markers and/or negative selection against hematopoietic stem and progenitor markers such as CD34, CD133, CD8, etc. Some surface marker expression typical of msenchyma stem cell populations is described hereinabove. Generally, however, mesenchymal stem cells are positive for CD105, CD90, CD44, CD73, CD29, CD13, CD34, CD146, CD106, CD54 and CD166. According to a specific embodiment, the MSCs are moderately positive for CD106 e.g., over 30%, over 40%, over 50%, over 60%, over 70%, over 80%, over 90% of the population express CD106.

According to another embodiment over 90% of the population are $CD105^+CD45^-$.

Methods of determining protein cell-surface expression are well known in the art. Examples include immunological methods, such as, FACS analysis as well as biochemical methods (cell-surface labeling, e.g., radioactive, fluorescence, avidin-biotin).

Exemplary antibodies that may be used to verify the presence of mesenchymal stem cells include CD73 PE conjugated (BD Pharmingen), CD90 PE-Cy5 conjugated (eBioscience) CD105 PE conjugated (Beckman Coulter) CD14 FITC conjugated (eBioscience) CD19 PE-Cy5 conjugated (eBioscience) CD34 FITC conjugated (Beckman Coulter), CD45 PE conjugated (eBioscience) and HLA-DR PE-Cy5 conjugated (BD Pharmingen).

It will be appreciated that a selecting stage may also be performed following the culturing with the aryl hydrocarbon receptor antagonist.

Thus, the method is effected by culturing the cells in a medium which comprises an aryl hydrocarbon receptor antagonist.

As used herein the term "medium" refers to a culture medium comprising nutritive substances.

According to a specific embodiment, the medium is devoid of animal contaminants (xeno-free).

According to one embodiment, the culture medium is devoid of serum (i.e. serum free medium) and comprises serum replacements including, but not limited to platelet lysate (during seeding and/or expansion).

According to a specific embodiment, the medium is a defined medium.

According to still another embodiment the medium comprises about 10% fetal bovine serum. Human serum is also contemplated.

A typical cell medium to which the aryl hydrocarbon receptor antagonist and optionally other factors (e.g., nicotinamide and FGF4, as further described hereinbelow) may be added is Dulbecco's modified MEM (DMEM). Alternatively, the cell medium may be Ham's F12. Other contemplated media include HEM RPMI, F-12, and the like.

The AHR antagonist:

Aryl hydrocarbon receptor (AHR) is a transcriptional factor regulating the transcription of various genes in human.

Herein, an AHR antagonist encompasses any agent which down-regulates (or inhibits) the activity and/or expression of AHR or which is capable of down-regulating (or inhibiting) the activity and/or expression of aryl hydrocarbon receptor and/or any agent which is a down-stream effector of aryl hydrocarbon receptor pathway.

Herein, the expressions "an AHR antagonist", "an AHR inhibitor", "an agent/compound that inhibits AHR activity", "an agent/compound that down-regulates an activity and/or expression of AHR", "an agent/compound that is a down-stream effecter of AHR pathway", and "a down-stream effecter of AHR pathway", are used interchangeably.

Herein an agent that inhibits AHR activity describes a compound which decreases AHR activity to at least 10%, 20%, 30%, 50%, 60%, 70%, 80% or at least 90% the transcriptional activity of AHR as observed under activated conditions. An assay to measure AHR inhibitory activity is, for example, the dioxin-induced AHR dependent luciferase reporter gene assay. In some embodiments, an inhibitor of AHR activity is a compound that has an $EC_{50}$ of less than 10 µM, preferably less than 5 µM as measured in the dioxin-induced AHR dependent luciferase reporter gene assay.

Exemplary organic compounds which have been described in the art as inhibiting an AHR activity and are therefore suitable for use in embodiments of the present invention include, but are not limited to, 2-methyl-2H-pyrazole-3-carboxylic acid (2-methyl-4-o-tolylazophenyl) amide (CH223191), alpha napthoflavone, resveratrol (Nutr. Metab. Cardiovasc. Dis., 2003 April; 13(2):104-13), 3'-methoxy-4'-nitroflavone (Biochem. Pharmacol., 2007 May 15; 73(10):1622-34, Epub 2007 Jan. 30), and 6-methyl-1,3,8-trichlorodibenzofuran (Cancer Res., 2004, Apr. 15; 64(8):2889-97).

Herein, a down-stream effector of AHR pathway is a gene which is directly regulated at the transcriptional level by AHR. Examples of such genes include, but are not limited to, Cyp1B1, Cyp1A1, and AHRR. AHR also functions in pathways outside of its well-characterized role in xenobiotic enzyme induction. Xenobiotic ligands of AHR have been shown to regulate beta-catenin, STATS, STAT1, HES-1, c-Myc, C/EBP, PU.1, p21, P27, pRb, deoxynucleotidyl transferase, CXCR4, and its chemokine ligand CXCL12 (SDF-1).

In some embodiments, an agent capable of down-regulating the activity and/or expression of aryl hydrocarbon receptor is a compound of Formula I:

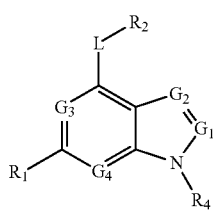

Formula I wherein:
$G_1$ is selected from N and $CR_3$;
$R_3$ is selected from hydrogen, $C_{1-4}$alkyl and biphenyl;
$G_2$, $G_3$ and $G_4$ are each independently selected from —CH— and N; with the proviso that at least one of $G_3$ and $G_4$ is N; and with the proviso that $G_1$ and $G_2$ are not both N;
L is a substituted or unsubstituted amino or alkylamino such as, for example, —$NR_{5a}(CH_2)_{0-3}$— (0-3 herein means 0, 1, 2 or 3), —$NR_{5a}CH(C(O)OCH_3)CH_2$—, —$NR_{5a}(CH_2)_2NR_{5b}$—, —$NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from the group consisting of hydrogen and $C_{1-4}$alkyl;

$R_1$ is selected from hydrogen, aryl (e.g., phenyl) and heteroaryl (e.g., thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl), wherein the aryl or heteroaryl can be optionally substituted by 1 to 3 substituents such as, but not limited to, cyano, hydroxy, $C_{1-4}$alkyl, $C_{1-4}$alkoxy, halo, halo-substituted-$C_{1-4}$alkyl, halo-substituted-$C_{1-4}$alkoxy, amino, —$C(O)R_{8a}$, —$S(O)_{0-2}R_{8a}$, —$C(O)OR_{8a}$ and —$C(O)NR_{8a}R_{8b}$; wherein each of $R_{8a}$ and $R_{8b}$ can independently be hydrogen or $C_{1-4}$alkyl (or optionally cycloalkyl and aryl); with the proviso that $R_1$ and $R_3$ are not both hydrogen;

$R_2$ is selected from —$S(O)_2NR_{6a}R_{6b}$, —$NR_{9a}C(O)R_{9b}$, —$NR_{6a}C(O)NR_{6b}R_{6c}$, aryl (e.g., phenyl), and heteroaryl (e.g., 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl); wherein $R_{6a}$, $R_{6b}$ and $R_{6c}$ are independently selected from hydrogen and $C_{1-4}$alkyl; wherein said aryl and heteroaryl is optionally substituted with 1 to 3 substituents such as, but not limited to, hydroxy, halo, methyl, methoxy, amino, —$O(CH_2)nNR_{7a}R_{7b}$, —$S(O)_2NR_{7a}R_{7b}$, —$OS(O)_2NR_{7a}R_{7b}$ and —$NR_{7a}S(O)_2R_{7b}$; wherein each of $R_{7a}$ and $R_{7b}$ can independently be hydrogen or $C_{1-4}$alkyl (or optionally cycloalkyl and aryl); and $R_4$ is selected from $C_{1-10}$alkyl, $C_{1-10}$alkenyl (e.g., prop-1-en-2-yl), cycloalkyl (e.g., cyclohexyl, cyclopropyl), aryl (e.g., phenyl), alkaryl (e.g., benzyl, benzhydryl), heteroalicyclic and heteroaryl (e.g., 2-(2-oxopyrrolidin-1-yl)ethyl, oxetan-3-yl, tetrahydro-2H-pyran-3-yl, tetrahydro-2H-pyran-4-yl, tetrahydrofuran-3-yl, (4-pentylphenyl)(phenyl)methyl and 1-(1-(2-oxo-6,9,12-trioxa-3-azatetradecan-14-yl)-1H-1,2,3-triazol-4-yl)ethyl; wherein each of said alkyl, alkenyl, cycloalkyl, aryl, heteroaryl and heteroalicyclic can be optionally substituted with 1 to 3 substituents independently selected from hydroxy, $C_{1-4}$alkyl and halo-substituted-$C_{1-4}$alkyl; or the N-oxide derivatives, prodrug derivatives, protected derivatives, individual isomers and mixture of isomers thereof; or the salts (preferably the pharmaceutically acceptable salts) and solvates (e.g. hydrates) of such compounds.

In some embodiments, the AHR antagonist has Formula I as described herein, wherein $G_1$ is $CR_3$, as defined herein, and $G_2$, $G_3$ and $G_4$ are each N. Compounds encompassed by these embodiments can be collectively represented by Formula Ia as follows:

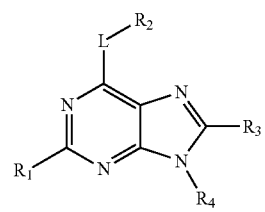

Formula Ia wherein $R_1$-$R_4$ and L are as defined herein for Formula I.

In some embodiments, the AHR antagonist has Formula I as described herein, wherein $G_2$ is CH, and $G_1$, $G_3$ and $G_4$ are each N. Compounds encompassed by these embodiments can be collectively represented by Formula Ib as follows:

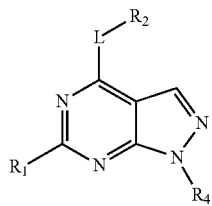

Formula Ib wherein $R_1$, $R_2$, $R_4$ and L are as defined herein for Formula I.

In some embodiments, the AHR antagonist has Formula I as described herein, wherein $G_1$ is $CR_3$, as defined herein, $G_2$ and $G_4$ are each N, and $G_3$ is CH. Compounds encompassed by these embodiments can be collectively represented by Formula Ic as follows:

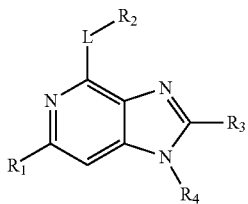

Formula Ic wherein $R_1$-$R_4$ and L are as defined herein for Formula I.

In some embodiments, the AHR antagonist has Formula I as described herein, wherein $G_1$ is $CR_3$, as defined herein, $G_2$ and $G_3$ are each N, and $G_4$ is CH. Compounds encompassed by these embodiments can be collectively represented by Formula Id as follows:

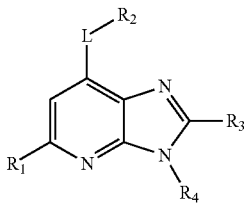

Formula Id wherein $R_1$-$R_4$ and L are as defined herein for Formula I.

In some embodiments, the AHR antagonist has Formula I as described herein, wherein $G_1$ is $CR_3$, as defined herein, $G_3$ and $G_4$ are each N, and $G_2$ is CH. Compounds encompassed by these embodiments can be collectively represented by Formula Ie as follows:

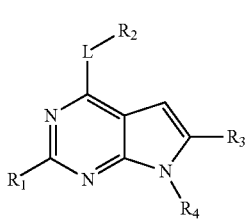

Formula Ie wherein $R_1$-$R_4$ and L are as defined herein for Formula I.

In some embodiments, for any of Formulae Ia-Ie, L is selected from $-NR_{5a}(CH_2)_{0-3}-$, $-NR_{5a}CH(C(O)OCH_3)CH_2-$, $-NR_{5a}(CH_2)_2NR_{5b}-$, $-NR_{5a}(CH_2)_2S-$, $-NR_{5a}CH_2CH(CH_3)CH_2-$, $-NR_{5a}CH_2CH(OH)-$ and $-NR_{5a}CH(CH_3)CH_2-$; wherein $R_{ya}$ and $R_{sb}$ are each independently selected from hydrogen and $C_{1-4}$alkyl; wherein the right side of the L moiety as shown is attached to $R_2$, for example: $-NR_{5a}(CH_2)_{0-3}-R_2$, $-NR_{5a}CH(C(O)OCH_3)CH_2-R_2$, $-NR_{5a}(CH_2)_2NR_{5b}-R_2$, $-NR_{5a}(CH_2)_2S-R_2$, $-NR_{5a}CH_2CH(CH_3)CH_2-R_2$, $-NR_{5a}CH_2CH(OH)-R_2$ and $-NR_{5a}CH(CH_3)CH_2-R_2$.

In some embodiments, L is an amine or an aminoalkyl and $R_2$ is attached to the carbon atom at the distal end of the alkyl substituting the amino, if present, or to a substituent of this carbon atom, if present.

$R_1$ is selected from hydrogen, aryl (e.g., phenyl), and heteroaryl (e.g., thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl); wherein said aryl or heteroaryl of $R_1$ can be optionally substituted by 1 to 3 substituents independently selected from cyano, hydroxy, $C_{1-4}$alkyl, $C_{1-4}$alkoxy, halo, halo-substituted-$C_{1-4}$alkyl, $-S(O)_{0-2}R_{8a}$ and $-C(O)OR_{8a}$; wherein $R_{8a}$ and $R_{8b}$ are independently selected from hydrogen and $C_{1-4}$alkyl; with the proviso that $R_1$ and $R_3$, if both present, are not both hydrogen;

$R_2$ is selected from $-NR_{6a}C(O)NR_{6b}R_{6c}$ (a urea or urea derivative radical), aryl (e.g., phenyl), and heteroaryl or heteroalicyclic such as, but not limited to, 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl; wherein $R_{6a}$, $R_{6b}$ and $R_{6c}$ are independently selected from hydrogen and $C_{1-4}$alkyl; wherein said aryl, heteroaryl and heteroalicyclic of $R_2$ is each independently optionally substituted with 1 to 3 substituents independently selected from hydroxy, halo, methoxy, amino, $-OS(O)_2NR_{7a}R_{7b}$ and $-NR_{7a}S(O)_2R_{7b}$; wherein $R_{7a}$ and $R_{7b}$ are independently selected from hydrogen and $C_{1-4}$alkyl;

$R_3$, when present, is hydrogen, $C_{1-4}$alkyl and biphenyl; and $R_4$ is selected from substituted or unsubstituted alkyl or alkenyl (e.g., isopropyl, methyl, ethyl, prop-1-en-2-yl, isobutyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl), cycloalkyl (e.g., cyclohexyl), aryl (e.g., phenyl), alkaryl (e.g., benzyl and benhydryl), and a heteroalicyclic or heteroaryl (e.g., 2-(2-oxopyrrolidin-1-yl)ethyl, oxetan-3-yl, oxetan-2-yl, tetrahydro-2H-pyran-2-yl, tetrahydrofuran-3-yl); wherein said cycloalkyl, heteroalicyclic, aryl, alkaryl and heteroaryl can each be optionally substituted with 1 to 3 substituents independently selected from $C_{1-4}$alkyl and halo-substituted-$C_{1-4}$alkyl.

In some embodiments, for each of Formulae I and Ia-Ie, L is selected from $-NR_{5a}(CH_2)_{0-3}-$, $-NR_{5a}CH(C(O)OCH_3)CH_2-$, $-NR_{5a}(CH_2)_2NR_{5b}-$, $-NR_{5a}(CH_2)_2S-$, $-NR_{5a}CH_2CH(CH_3)CH_2-$, $-NR_{5a}CH(CH_3)CH_2-$ and $-NR_{5a}CH_2CH(OH)-$; wherein $R_{5a}$ and $R_{5b}$ are independently selected from hydrogen and methyl; and $R_1$ is selected from hydrogen, phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl; wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl or thiazol-5-yl of $R_1$ can be optionally substituted by 1 to 3 substituents independently selected from cyano, hydroxy, $C_{1-4}$alkyl, $C_{1-4}$alkoxy, halo, halo-substituted-$C_{1-4}$alkyl, —S(O)$_{0-2}$R$_{8a}$ and —C(O)OR$_{8a}$; wherein $R_{8a}$ and $R_{8b}$ are independently selected from hydrogen and $C_{1-4}$alkyl; with the proviso that $R_1$ and $R_3$, if both present, are not both hydrogen.

In some embodiment, when L is —NR$_{5a}$(CH$_2$)$_{0-3}$, it is preferably —NR$_{5a}$(CH$_2$)$_{1-3}$ (where 1-3 herein is 1, 2 or 3).

In any of the above-described embodiments, $R_2$, $R_3$ and $R_4$ are as defined herein.

In any of the above-described embodiments, $R_2$ is selected from urea (or a derivative thereof, as described hereinabove), phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl, 1H-benzo[d]imidazol-5-yl and 1H-imidazol-4-yl; wherein said phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-benzo[d]imidazol-5-yl of $R_2$ is optionally substituted with one or more of hydroxy, methoxy, methyl, halo, amino and amino-sulfonyl.

In any of the above-described embodiments, $R_3$, if present, is selected from hydrogen, methyl and biphenyl; and $R_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl) ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tetrahydro-2H-pyran-4-yl, phenyl, tetrahydrofuran-3-yl or benzyl can be optionally substituted with 1 to 3 substituents independently selected from methyl and trifluoromethyl.

Exemplary compounds which are suitable for use as AHR antagonists according to some embodiments of the present invention include, but are not limited to:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-yl amino)ethyl)phenol;
4-(2-(9-isopropyl-2-(thiophen-2-yl)-9H-purin-6-ylamino) ethyl)phenol;
4-(2-(2-(benzo[b]thiophen-3-yl)-9-(4-(trifluoromethyl)benzyl)-9H-purin-6-yl amino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino) ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[b]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino) ethyl)phenol;
4-(2-(9-isopropyl-2-(pyridin-3-yl)-9H-purin-6-ylamino) ethyl)phenol;
4-(2-(9-isopropyl-2-phenyl-9H-purin-6-ylamino)ethyl)phenol;
4-(2-(9-isopropyl-2-(thiophen-3-yl)-9H-purin-6-ylamino) ethyl)phenol;
4-(2-(2-(furan-3-yl)-9-isopropyl-9H-purin-6-ylamino)ethyl) phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;
4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-seq-butyl-9H-purin-6-amine;
3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate;
N-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino) ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino) ethyl)phenol;
4-(2-(2-(1H-imidazol-1-yl)-9-isopropyl-9H-purin-6-ylamino)ethyl)phenol;
4-(2-(9-isopropyl-2-(pyridazin-4-yl)-9H-purin-6-ylamino) ethyl)phenol;
4-(2-(9-isopropyl-2-(pyrazin-2-yl)-9H-purin-6-ylamino) ethyl)phenol;
4-(2-(9-isopropyl-2-(pyridin-2-yl)-9H-purin-6-ylamino) ethyl)phenol;
4-(2-(9-isopropyl-2-(5-(methylsulfonyl)pyridin-3-yl)-9H-purin-6-ylamino) ethyl)phenol;
4-(2-(9-isopropyl-2-(5-methylpyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(1-methyl-1H-pyrazol-4-yl)-9H-purin-6-ylamino)ethyl)phenol;

4-(2-(9-isopropyl-2-(pyridin-3-yl)-9H-purin-6-ylamino) ethyl)-2-methoxy phenol;
4-(2-(9-isopropyl-2-(pyridin-3-yl)-9H-purin-6-ylamino) ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-{2-[(3-methyl-1H-1,2,4-triazol-5-yl)sulfanyl]ethyl}-9-(propan-2-yl)-2-(pyridin-3-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl) urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino) ethyl)phenyl)methanesulfonamide;
4-(2-(2-(pyridin-3-yl)-9-(tetrahydrofuran-3-yl)-9H-purin-6-ylamino)ethyl)-phenol;
4-(2-(9-isopropyl-2-(pyridin-3-yl)-9H-purin-6-ylamino) propyl)phenol;
4-(2-(9-(oxetan-3-yl)-2-(pyridin-3-yl)-9H-purin-6-ylamino) ethyl)phenol;
5-(6-(4-hydroxyphenethylamino)-9-isopropyl-9H-purin-2-yl)-N-methylnicotin-amide;
4-(2-(9-(1-hydroxypropan-2-yl)-2-(pyridin-3-yl)-9H-purin-6-ylamino)-ethyl)phenol;
4-(2-(9-isopropyl-2-(pyridin-3-yl)-9H-purin-6-ylamino) ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol;
4-(2-(9-isopropyl-2-(thiazol-5-yl)-9H-purin-6-ylamino) ethyl)phenol;
4-(2-(2-(1H-benzo[d]imidazol-1-yl)-9-isopropyl-9H-purin-6-ylamino)ethyl)-phenol;
4-(2-(2-(2,4-dimethyl-1H-imidazol-1-yl)-9-isopropyl-9H-purin-6-ylamino) ethyl)phenol;
4-(2-(9-isopropyl-2-(2-methyl-1H-imidazol-1-yl)-9H-purin-6-ylamino)ethyl)-phenol;
5-(9-sec-butyl-6-(4-hydroxy-3-methylphenethylamino)-9H-purin-2-yl)-nicotinonitrile;
N-(2-(1H-pyrrolo[2,3-b]pyridin-5-yl)ethyl)-9-isopropyl-2-(pyridin-3-yl)-9-H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino) ethyl)phenol;
5-(6-(2-(1H-indol-3-yl) ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl)ethyl)-9-sec-butyl-2-(5-methylpyridin-3-yl)-9H-purin-6-amine;
(S)—N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
4-(2-(6-(benzo[b]thiophen-3-yl)-1-isopropyl-1H-pyrazolo [3,4-d]pyrimidin-4-yl amino)ethyl)phenol;
(R)-4-(2-(2-(5-fluoropyridin-3-yl)-9-(tetrahydrofuran-3-yl)-9H-purin-6-yl-amino)ethyl)phenol;
4-(2-(9-isopropyl-2-(pyridin-3-yl)-9H-purin-6-ylamino) ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
4-(2-(2-(5-fluoropyridin-3-yl)-7-isopropyl-7H-pyrrolo[2,3-d]pyrimidin-4-yl amino)ethyl)phenol;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino) ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino) ethyl)-2-methylphenol;
4-(2-(2-(benzo[b]thiophen-3-yl)-9-(oxetan-3-yl)-9H-purin-6-ylamino)ethyl)-phenol;
(S)-4-(2-(2-(benzo[b]thiophen-3-yl)-9-(tetrahydrofuran-3-yl)-9H-purin-6-yl amino)ethyl)phenol;
(R)-4-(2-(2-(benzo[b]thiophen-3-yl)-9-(tetrahydrofuran-3-yl)-9H-purin-6-yl amino)ethyl)phenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)—N-(2-(1H-indol-3-yl)ethyl)-2-(5-fluoropyridin-3-yl)-9-(tetrahydrofuran-3-yl)-9H-purin-6-amine;
4-(2-(2-(3H-imidazo[4,5-b]pyridin-3-yl)-9-isopropyl-9H-purin-6-ylamino) ethyl)phenol;

4-(2-(2-(1H-imidazo[4,5-b]pyridin-1-yl)-9-isopropyl-9H-purin-6-ylamino) ethyl)phenol;

4-(2-(6-(5-fluoropyridin-3-yl)-1-isopropyl-1H-imidazo[4,5-c]pyridin-4-yl amino)ethyl)phenol;

4-(2-(2-(4,5-dimethyl-1H-imidazol-1-yl)-9-isopropyl-9H-purin-6-ylamino) ethyl)phenol;

2-(5-fluoropyridin-3-yl)-9-isopropyl-N-(2-(pyridin-3-yl) ethyl)-9H-purin-6-amine;

4-(2-(2-(5-fluoropyridin-3-yl)-9-isopropyl-9H-purin-6-ylamino)-1-hydroxy ethyl)phenol;

2-(5-fluoropyridin-3-yl)-9-isopropyl-N-(2-(6-methoxy-1H-indol-3-yl)ethyl)-9H-purin-6-amine;

N-(2-(1H-indol-3-yl)ethyl)-2-(5-fluoropyridin-3-yl)-9-isopropyl-9H-purin-6-amine;

2-(5-fluoropyridin-3-yl)-9-isopropyl-N-(2-(5-methoxy-1H-indol-3-yl)ethyl)-9H-purin-6-amine;

N-(2-(1H-indol-3-yl)ethyl)-2-(5-fluoropyridin-3-yl)-9-(prop-1-en-2-yl)-9H-purin-6-amine;

5-(2-(2-(5-fluoropyridin-3-yl)-9-isopropyl-9H-purin-6-ylamino)ethyl)pyridin-2-ol;

N-(2-(1H-pyrrolo[2,3-b]pyridin-3-yl)ethyl)-2-(5-fluoropyridin-3-yl)-9-isopropyl-9H-purin-6-amine;

N-(2-(6-(2-(diethylamino)ethoxy)-1H-indol-3-yl)ethyl)-2-(5-fluoropyridin-3-yl)-9-isopropyl-9H-purin-6-amine;

4-(2-(5-(5-fluoropyridin-3-yl)-3-isopropyl-3H-imidazo[4,5-b]pyridin-7-yl amino)ethyl)phenol;

N-(2-(1H-indol-3-yl)ethyl)-9-sec-butyl-2-(2-methyl-1H-imidazol-1-yl)-9H-purin-6-amine;

4-(2-(2-(2-ethyl-1H-imidazol-1-yl)-9-isopropyl-9H-purin-6-ylamino)ethyl)phenol;

4-(2-(9-isopropyl-2-(2-propyl-1H-imidazol-1-yl)-9H-purin-6-ylamino)-ethyl)phenol;

3-(2-(2-(5-fluoropyridin-3-yl)-9-isopropyl-9H-purin-6-ylamino)ethyl)-1H-indol-6-ol;

N-(2-(1H-indol-3-yl)ethyl)-9-isopropyl-2-(5-methylpyridin-3-yl)-9H-purin-6-amine;

N-(2-(1H-indol-3-yl)ethyl)-9-isopropyl-2-(2-methyl-1H-imidazol-1-yl)-9H-purin-6-amine;

2-(5-fluoropyridin-3-yl)-9-isopropyl-N-(2-(7-methyl-1H-indol-3-yl)ethyl)-9H-purin-6-amine;

N-(2-(1H-indol-3-yl)ethyl)-2-(5-fluoropyridin-3-yl)-9-(oxetan-3-yl)-9H-purin-6-amine;

N-(2-(1H-indol-3-yl)ethyl)-2-(5-methylpyridin-3-yl)-9-(oxetan-3-yl)-9H-purin-6-amine;

N-(2-(6-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(6-methyl-1H-indol-3-yl)ethyl)-9H-purin-6-amine;

2-(5-fluoropyridin-3-yl)-9-isopropyl-N-(2-(2-methyl-1H-indol-3-yl) ethyl)-9H-purin-6-amine;

N-(2-(4-fluoro-1H-indol-3-yl)ethyl)-2-(5-fluoropyridin-3-yl)-9-isopropyl-9H-purin-6-amine;

N-(2-(7-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(4-methyl-1H-indol-3-yl)ethyl)-9H-purin-6-amine;

4-(2-(2-(benzo[b]thiophen-3-yl)-7-isopropyl-7H-pyrrolo[2,3-d]pyrimidin-4-yl amino)ethyl)phenol;

9-isopropyl-2-(pyridin-3-yl)-N-(2-(pyridin-4-yl)ethyl)-9H-purin-6-amine;

N-(2-(1H-pyrrolo[2,3-b]pyridin-5-yl)ethyl)-9-isopropyl-2-(pyridin-3-yl)-9H-purin-6-amine;

4-(2-(2-(5-fluoropyridin-3-yl)-9-(1-hydroxypropan-2-yl)-9H-purin-6-ylamino)ethyl)-2-methylphenol;

4-(2-(2-(benzo[b]thiophen-3-yl)-9-cyclohexyl-9H-purin-6-ylamino)ethyl)phenol;

4-(2-(9-isopropyl-2-(thiophen-3-yl)-9H-purin-6-ylamino) ethyl)phenol; and 1-(2-(2-(benzo[b]thiophen-3-yl)-6-(4-hydroxyphenethylamino)-9H-purin-9-yl) ethyl)pyrrolidin-2-one.

In some embodiments, the AHR antagonist is a compound of Formula Ia, as depicted herein, wherein:

L is selected from an alkylamino (wherein the alkyl can be substituted or unsubstituted, linear or branched), alkyl (optionally substituted, for example, by alkoxy or by an aminoalkyl), N-amide, and an amine substituted by a heteroaryl or a heteroalicyclic.

In some embodiments, L is selected from —NR$_{5a}$(CH$_2$)$_{0-3}$— (as an exemplary amino or alkylamino), —NR$_{5a}$CH(C(O)OCH$_3$)CH$_2$— (as an exemplary carboxy-substituted alkylamino), —NR$_{5a}$(CH$_2$)$_2$NR$_{5b}$— (as an exemplary aminoalkyl in which the distal carbon atom is substituted by an amine, as defined herein), —NR$_{5a}$(CH$_2$)$_2$S— (as an exemplary aminoalkyl, in which the distal carbon atom is substituted by thio, as defined herein), —NR$_{5a}$CH$_2$CH(CH$_3$)CH$_2$— and —NR$_{5a}$CH(CH$_3$)CH$_2$— (as exemplary amino alkyls wherein the alkyl is a branched alkyl), —(CH$_2$)$_3$— (as an exemplary alkyl), —CH$_2$OCH$_2$— as an exemplary alkyl substituted by alkoxy, or as an exemplary ether), —CH$_2$NR$_{5a}$CH$_2$— (an exemplary alkyl substituted by an amino, as defined herein), —NR$_{5a}$C(O)CH$_2$— (as an exemplary N-amide) and —NR$_{5a}$Y— (as an exemplary amine substituted by a heterocyclic moiety); wherein R$_{5a}$ and R$_{5b}$ are independently selected from hydrogen and C$_{1-4}$alkyl; and Y is a 5-membered heteroaryl ring containing up to 3 heteroatoms selected from O, N and S;

In some embodiments, for any of the above-described embodiments for Formula Ia, R$_1$ is selected from hydrogen, and substituted or unsubstituted aryl, heteroaryl and heteroalicyclic.

In some of these embodiments, R$_1$ is selected from phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, 1H-indol-3-yl, 1H-pyrrol-2-yl and thiazol-5-yl. When said phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, 1H-indol-3-yl, 1H-pyrrol-2-yl or thiazol-5-yl, or any other aryl, heteroaryl or heteroalicyclic of R$_1$, is substituted, it may comprise one or more, e.g., 1 to 3, substituents, such as, but not limited to, cyano, hydroxy, C$_{1-4}$alkyl, C$_{1-4}$alkoxy, halo, halo-substituted-C$_{1-4}$alkyl, halo-substituted-C$_{1-4}$alkoxy, hydroxy, amino, —C(O)R$_{8a}$, —S(O)$_{0-2}$R$_{8a}$, —C(O)OR$_{8a}$ and —C(O)NR$_{8a}$R$_{8b}$; wherein R$_{8a}$ and R$_{8b}$ are independently selected from hydrogen and C1$_{-4}$alkyl.

In some embodiments, R$_1$ and R$_3$ are not both hydrogen.

In some embodiments, for any of the above-described embodiments for Formula Ia, R$_2$ is selected from S-sulfonamide, N-amide, urea or a derivative thereof, and substituted or unsubstituted aryl, heteroaryl and heteroalicyclic.

In some of these embodiments, R$_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein $R_{6a}$, $R_{6b}$ and $R_{6c}$ are independently selected from hydrogen and $C_{1-4}$alkyl.

Whenever any of the aryl, heteroaryl or heteroalicyclic of $R_2$ is substituted, it comprises one or more (e.g., 1 to 3) substituents such as, but not limited to, hydroxy, halo, alkyl (e.g., methyl), alkoxy (e.g., methoxy), amino, $—S(O)_2NR_{7a}R_{7b}$, $—OS(O)_2NR_{7a}R_{7b}$ and $—NR_{7a}S(O)_2NR_{7b}$; wherein $R_{7a}$ and $R_{7b}$ are each independently selected from hydrogen and $C_{1-4}$alkyl, or, alternatively, it comprises a single substituent selected from 5-((3aS,4S,6aR)-2-oxohexahydro-1H-thieno[3,4-d]imidazol-4-yl)pentanoyloxy-, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In some embodiments of any of the above-described embodiments of Formula Ia, $R_3$ is selected from hydrogen, $C_{1-4}$alkyl and aryl (e.g., biphenyl).

In some embodiments of any of the above-described embodiments of Formula Ia, $R_4$ is selected from a substituted or unsubstituted, linear or branched alkyl, and a substituted or unsubstituted cycloalkyl, alkaryl, aryl, heteroaryl or heteroalicyclic.

In some of these embodiments, $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl.
Whenever the cycloalkyl, alkaryl, aryl, heteroaryl or heteroalicyclic is substituted, it comprises one or more (e.g., 1 to 3) substituents, each independently selected from $C_{1-4}$alkyl and halo-substituted-$C_{1-4}$alkyl.

For any of the embodiments described herein for Formula Ia, encompassed are also the N-oxide derivatives, prodrug derivatives, protected derivatives, individual isomers and mixture of isomers thereof; or the pharmaceutically acceptable salts and solvates (e.g. hydrates) of any of the described compounds.

In some embodiments, with reference to compounds of Formula Ia, L is selected from $—NR_{5a}(CH_2)_{0-3}—$, $—NR_{5a}CH(C(O)OCH_3)CH_2—$, $—NR_{5a}(CH_2)_2NR_{5b}—$, $—NR_{5a}(CH_2)_2S—$, $—NR_{5a}CH_2CH(CH_3)CH_2—$, $—NR_{5a}CH(CH_3)CH_2—$, $—(CH_2)_3—$, $—CH_2OCH_2—$, $—CH_2NR_{5a}CH_2—$, $—NR_{5a}C(O)CH_2—$ and $—NR_{5a}Y—$; wherein $R_{5a}$ and $R_{5b}$ are independently selected from hydrogen and methyl; and Y is selected from isoxazole and 1,3,4-oxadiazole.

In some of these embodiments, when L is $—NR_{5a}(CH_2)_{0-3}$, it is preferably $—NR_{5a}(CH_2)_{1-3}$ (where 1-3 herein means 1, 2 or 3).

In some embodiments, for any of the above-described embodiments for Formula Ia, $R_1$ is selected from hydrogen, phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl, and pyridin-3-yl; wherein said phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl or pyridin-3-yl of $R_1$ is optionally substituted with 1 to 3 substituents, each independently selected from cyano, methyl, methyl-sulfonyl, methoxy, halo, hydroxy, carboxyl, ethoxy-carbonyl, methyl-amino-carbonyl and amino; with the proviso that $R_1$ and $R_3$ are not both hydrogen.

In some embodiments, for any of the above-described embodiments for Formula Ia, $R_2$ is selected from amino-sulfonyl, methyl-carbonyl-amino, methyl-sulfonyl-amino, amino-sulfonyl-oxy, urea, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl;
wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl of $R_2$ is optionally substituted with hydroxy, methoxy, methyl, halo, amino, amino-sulfonyl, 5-((3aS,4S,6aR)-2-oxohexahydro-1H-thieno[3,4-d]imidazol-4-yl)pentanoyloxy-, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In some embodiments, for any of the above-described embodiments for Formula Ia, $R_3$ is selected from hydrogen, methyl, and biphenyl; and $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 substituents, each independently selected from methyl and trifluoromethyl.

Exemplary AHR antagonists encompassed by some embodiments of the present invention include, but are not limited to:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;

4-(2-(9-benzhydryl-2-(benzo[b]thiophen-3-yl)-9H-purin-6-ylamino)ethyl)phenol;
4-(2-(2-(benzo[b]thiophen-3-yl)-9-(tetrahydro-2H-pyran-3-yl)-9H-purin-6-yl amino)ethyl)phenol;
4-(2-(2-(benzo[b]thiophen-3-yl)-9-(4-(trifluoromethyl)benzyl)-9H-purin-6-yl amino)ethyl)phenol;
4-(2-(2-(benzo[b]thiophen-3-yl)-9-isobutyl-9H-purin-6-ylamino)ethyl)phenol;
4-(2-(2-(benzo[b]thiophen-3-yl)-9-methyl-9H-purin-6-ylamino)ethyl)phenol;
4-(2-(2-(benzo[b]thiophen-3-yl)-9-(4-methylbenzyl)-9H-purin-6-ylamino) ethyl)phenol;
N-(2-(1H-indol-3-yl)ethyl)-2-(benzo[b]thiophen-3-yl)-9-isopropyl-9H-purin-6-amine;
2-(benzo[b]thiophen-3-yl)-9-isopropyl-N-(2-(thiophen-3-yl)ethyl)-9H-purin-6-amine;
3-(2-(2-(benzo[b]thiophen-3-yl)-9-isopropyl-9H-purin-6-ylamino)ethyl)phenol;
2-(benzo[b]thiophen-3-yl)-N-(4-fluorophenethyl)-9-isopropyl-9H-purin-6-amine;
N-(4-aminophenethyl)-2-(benzo[b]thiophen-3-yl)-9-isopropyl-9H-purin-6-amine;
4-(2-(9-isopropyl-2-(pyrimidin-5-yl)-9H-purin-6-ylamino)ethyl)phenol;
4-(2-(9-isopropyl-2-(pyridin-3-yl)-9H-purin-6-ylamino)ethyl)phenol;
4-(2-(9-isopropyl-2-phenyl-9H-purin-6-ylamino)ethyl)phenol;
4-(2-(9-isopropyl-2-(thiophen-3-yl)-9H-purin-6-ylamino)ethyl)phenol;
4-(2-(2-(furan-3-yl)-9-isopropyl-9H-purin-6-ylamino)ethyl)phenol;
2-(benzo[b]thiophen-3-yl)-N-(4-fluorophenethyl)-9-phenyl-9H-purin-6-amine;
N-benzyl-8-(biphenyl-4-yl)-9-isopropyl-9H-purin-6-amine;
4-(2-(2-(benzo[b]thiophen-3-yl)-9-(nonan-2-yl)-9H-purin-6-ylamino)ethyl)phenol;
4-(2-(2-(benzo[b]thiophen-3-yl)-9-((4-pentylphenyl)(phenyl)methyl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
4-(2-(2-(benzo[b]thiophen-3-yl)-9-sec-butyl-9H-purin-6-ylamino)ethyl)phenol;
3-(2-(2-(benzo[b]thiophen-3-yl)-9-isopropyl-9H-purin-6-ylamino)ethyl)-1H-indol-5-ol;
3-(2-(2-(benzo[b]thiophen-3-yl)-9-isopropyl-9H-purin-6-ylamino)ethyl)-1H-indol-5-yl,
5-((3aS,4S,6aR)-2-oxohexahydro-1H-thieno[3,4-d]imidazol-4-yl)pentanoate;
N-(2-(2-(3-(2-(2-(benzo[b]thiophen-3-yl)-9-isopropyl-9H-purin-6-ylamino)ethyl)-1H-indol-5-yloxy)ethoxy)ethyl)-5-((3aS,4S,6aR)-2-oxohexahydro-1H-thieno[3,4-d]imidazol-4-yl)pentanamide;
N-(4-(4-(2-(3-(2-(2-(benzo[b]thiophen-3-yl)-9-isopropyl-9H-purin-6-ylamino)ethyl)-1H-indol-5-yloxy)acetamido)benzoyl)phenyl)hex-5-ynamide;
N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide;
4-(2-(9-isopropyl-2-(pyridin-4-yl)-9H-purin-6-ylamino)ethyl)phenol;
ethyl 5-(6-(4-hydroxyphenethylamino)-9-isopropyl-9H-purin-2-yl)nicotinate;
ethyl 5-(6-(4-hydroxyphenethylamino)-9-isopropyl-9H-purin-2-yl)nicotinate;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
4-(2-(9-isopropyl-2-(2-methoxypyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(pyrrolidin-1-yl)-9H-purin-6-ylamino)ethyl)phenol;
4-(2-(9-isopropyl-2-(1H-pyrazol-1-yl)-9H-purin-6-ylamino)ethyl)phenol;
4-(2-(2-(1H-imidazol-1-yl)-9-isopropyl-9H-purin-6-ylamino)ethyl)phenol;
4-(2-(9-isopropyl-2-(pyridazin-3-yl)-9H-purin-6-ylamino)ethyl)phenol;
4-(2-(9-isopropyl-2-(pyridazin-4-yl)-9H-purin-6-ylamino)ethyl)phenol;
4-(2-(9-isopropyl-2-(pyrazin-2-yl)-9H-purin-6-ylamino)ethyl)phenol;
4-(2-(9-isopropyl-2-(pyridin-2-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(9-isopropyl-2-(5-methylpyridin-3-yl)-9H-purin-6-ylamino)ethyl)phenol;
4-(2-(2-(2-chloropyridin-3-yl)-6-isopropyl-2,6-dihydroimidazo[4,5-c]pyrazol-3-ylamino)ethyl)phenol;
4-(2-(2-(4-chloropyridin-3-yl)-9-isopropyl-9H-purin-6-ylamino)ethyl)phenol;
4-(2-(9-isopropyl-2-(4-methoxypyridin-3-yl)-9H-purin-6-ylamino)ethyl)phenol;
4-(2-(2-(5-fluoropyridin-3-yl)-9-isopropyl-9H-purin-6-ylamino)ethyl)phenol;
4-(2-(9-isopropyl-2-(thiazol-4-yl)-9H-purin-6-ylamino)ethyl)phenol;
4-(2-(9-isopropyl-2-(1-methyl-1H-pyrazol-4-yl)-9H-purin-6-ylamino)ethyl)-phenol;
4-(2-(9-isopropyl-2-(1H-pyrazol-3-yl)-9H-purin-6-ylamino)ethyl)phenol;
4-(2-(9-isopropyl-2-(1H-pyrazol-4-yl)-9H-purin-6-ylamino)ethyl)phenol;
4-(2-(9-isopropyl-2-(thiophen-2-yl)-9H-purin-6-ylamino)ethyl)phenol;
4-(6-(4-hydroxyphenethylamino)-9-isopropyl-9H-purin-2-yl)thiophene-2-carboxylic acid;
4-(2-(2-(furan-2-yl)-9-isopropyl-9H-purin-6-ylamino)ethyl)phenol;
4-(2-(9-isopropyl-2-(4-methylthiophen-3-yl)-9H-purin-6-ylamino)ethyl)phenol;
4-(2-(9-isopropyl-2-(pyridin-3-yl)-9H-purin-6-ylamino)ethyl)-2-methoxy-phenol;
4-(2-(9-isopropyl-2-(pyridin-3-yl)-9H-purin-6-ylamino)ethyl)-2-methoxy phenol;
N-[2-(6-methoxy-1H-indol-3-yl)ethyl]-9-(propan-2-yl)-2-(pyridin-3-yl)-9H-purin-6-amine;
N-[2-(5-methyl-1H-indol-3-yl)ethyl]-9-(propan-2-yl)-2-(pyridin-3-yl)-9H-purin-6-amine;
N-[2-(piperidin-4-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)piperidin-4-ol;
methyl(2S)-3-(4-hydroxyphenyl)-2-{[9-(propan-2-yl)-2-(pyridin-3-yl)-9H-purin-6-yl]amino}propanoate;
4-(2-{[9-(propan-2-yl)-2-(pyridin-3-yl)-9H-purin-6-yl]amino}ethyl)benzene-1-sulfonamide;
2-{[2-(1-benzothiophen-3-yl)-9-(propan-2-yl)-9H-purin-6-yl]amino}ethane-1-sulfonamide;

4-(2-{[9-(propan-2-yl)-2-(pyridin-3-yl)-9H-purin-6-yl]amino}ethyl)benzene-1,2-diol;
N-[2-(1H-imidazol-4-yl)ethyl]-9-(propan-2-yl)-2-(pyridin-3-yl)-9H-purin-6-amine;
1-(2-{[9-(propan-2-yl)-2-(pyridin-3-yl)-9H-purin-6-yl]amino}ethyl)imidazolidin-2-one;
N-[2-(5-amino-1H-1,2,4-triazol-3-yl)ethyl]-9-(propan-2-yl)-2-(pyridin-3-yl)-9H-purin-6-amine;
N-(2-{[9-(propan-2-yl)-2-(pyridin-3-yl)-9H-purin-6-yl]amino}ethyl)pyridin-2-amine;
9-(propan-2-yl)-N-[3-(1H-pyrazol-4-yl)propyl]-2-(pyridin-3-yl)-9-H-purin-6-amine;
N-[2-({[9-(propan-2-yl)-2-(pyridin-3-yl)-9H-purin-6-yl]amino}methyl)propyl]acetamide;
4-(2-{[9-(propan-2-yl)-2-(pyridin-3-yl)-9H-purin-6-yl]amino}ethyl)piperazin-2-one;
N-{2-[(3-methyl-1H-1,2,4-triazol-5-yl)sulfanyl]ethyl}-9-(propan-2-yl)-2-(pyridin-3-yl)-9H-purin-6-amine;
N-[3-(3,5-dimethyl-1H-pyrazol-4-yl)propyl]-9-(propan-2-yl)-2-(pyridin-3-yl)-9H-purin-6-amine;
(2-{[9-(propan-2-yl)-2-(pyridin-3-yl)-9H-purin-6-yl]amino}ethyl)urea;
5-({[9-(propan-2-yl)-2-(pyridin-3-yl)-9H-purin-6-yl]amino}methyl)-2,3-dihydro-1H-1,3-benzodiazol-2-one;
2-(1-benzothiophen-3-yl)-N-[2-(1H-imidazol-4-yl)ethyl]-9-(propan-2-yl)-9H-purin-6-amine;
1-(2-{[2-(1-benzothiophen-3-yl)-9-(propan-2-yl)-9H-purin-6-yl]amino}ethyl)imidazolidin-2-one;
N-[2-(5-amino-1H-1,2,4-triazol-3-yl)ethyl]-2-(1-benzothiophen-3-yl)-9-(propan-2-yl)-9H-purin-6-amine;
N-(2-{[2-(1-benzothiophen-3-yl)-9-(propan-2-yl)-9H-purin-6-yl]amino}ethyl)pyridin-2-amine;
2-(1-benzothiophen-3-yl)-9-(propan-2-yl)-N-[3-(1H-pyrazol-4-yl)propyl]-9H-purin-6-amine;
N-[2-({[2-(1-benzothiophen-3-yl)-9-(propan-2-yl)-9H-purin-6-yl]amino}methyl)propyl]acetamide;
4-(2-{[2-(1-benzothiophen-3-yl)-9-(propan-2-yl)-9H-purin-6-yl]amino}ethyl)piperazin-2-one;
2-(1-benzothiophen-3-yl)-N-{2-[(3-methyl-1H-1,2,4-triazol-5-yl)sulfanyl]ethyl}-9-(propan-2-yl)-9H-purin-6-amine;
2-(1-benzothiophen-3-yl)-N-[3-(3,5-dimethyl-1H-pyrazol-4-yl)propyl]-9-(propan-2-yl)-9H-purin-6-amine;
(2-{[2-(1-benzothiophen-3-yl)-9-(propan-2-yl)-9H-purin-6-yl]amino}ethyl) urea;
5-({[2-(1-benzothiophen-3-yl)-9-(propan-2-yl)-9H-purin-6-yl]amino}methyl)-2,3-dihydro-1H-1,3-benzodiazol-2-one;
N-[2-(1H-indol-3-yl)ethyl]-9-(propan-2-yl)-2-(pyridin-3-yl)-9H-purin-6-amine;
N-(4-(2-(9-isopropyl-2-(pyridin-3-yl)-9H-purin-6-ylamino)ethyl)phenyl)methanesulfonamide;
4-(2-(2-(pyridin-3-yl)-9-(tetrahydrofuran-3-yl)-9H-purin-6-ylamino)ethyl)phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
5-(6-(4-hydroxyphenethylamino)-9-isopropyl-9H-purin-2-yl)-N-methyl nicotinamide;
6-(9-isopropyl-2-(pyridin-3-yl)-9H-purin-6-ylamino)-5,6,7,8-tetrahydronaphthalen-2-ol;
N-(2-(1H-indazol-3-yl)ethyl)-9-isopropyl-2-(pyridin-3-yl)-9H-purin-6-amine;
4-(2-((9-isopropyl-2-(pyridin-3-yl)-9H-purin-6-yl)(methyl)amino)ethyl)phenol;
4-(2-(9-isopropyl-8-methyl-2-(pyridin-3-yl)-9H-purin-6-ylamino)ethyl)phenol;
1-(2-(9-isopropyl-2-(pyridin-3-yl)-9H-purin-6-ylamino)ethyl)-1H-benzo[d]imidazol-2(3H)-one;
4-(3-(9-isopropyl-2-(pyridin-3-yl)-9H-purin-6-yl)propyl)phenol;
4-((((9-isopropyl-2-(pyridin-3-yl)-9H-purin-6-yl)methyl)(methyl)amino) methyl)phenol;
4-(((9-isopropyl-2-(pyridin-3-yl)-9H-purin-6-yl)methylamino)methyl)phenol;
4-(((9-isopropyl-2-(pyridin-3-yl)-9H-purin-6-yl)methoxy)methyl)phenol;
N-(2-(indolin-5-yl)ethyl)-9-isopropyl-2-(pyridin-3-yl)-9H-purin-6-amine;
4-(2-(9-(1-methylpiperidin-4-yl)-2-(pyridin-3-yl)-9H-purin-6-ylamino)ethyl)phenol;
4-(2-(9-(piperidin-4-yl)-2-(pyridin-3-yl)-9H-purin-6-ylamino)ethyl)phenol;
N-(2-(1H-indazol-5-yl)ethyl)-9-isopropyl-2-(pyridin-3-yl)-9H-purin-6-amine;
N-(2-(1H-benzo[d]imidazol-5-yl)ethyl)-9-isopropyl-2-(pyridin-3-yl)-9H-purin-6-amine;
5-(2-(9-isopropyl-2-(pyridin-3-yl)-9H-purin-6-ylamino)ethyl)indolin-2-one;
4-(2-(9-cyclopropyl-2-(pyridin-3-yl)-9H-purin-6-ylamino)ethyl)phenol;
4-(2-(9-(1-hydroxypropan-2-yl)-2-(pyridin-3-yl)-9H-purin-6-ylamino)ethyl)phenol;
4-(2-(9-isopropyl-2-(pyridin-3-yl)-9H-purin-6-ylamino)ethyl)phenyl sulfamate;
2-(4-hydroxyphenyl)-N-(9-isopropyl-2-(pyridin-3-yl)-9H-purin-6-yl)acetamide;
4-(5-(9-isopropyl-2-(pyridin-3-yl)-9H-purin-6-ylamino)isoxazol-3-yl)phenol;
4-(5-(9-isopropyl-2-(pyridin-3-yl)-9H-purin-6-ylamino)-1,3,4-oxadiazol-2-yl)phenol;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)-phenol; and
4-(2-(9-isopropyl-2-(thiazol-5-yl)-9H-purin-6-ylamino)ethyl)phenol.

In some embodiments, for any of the above-described embodiments of Formula Ia, $R_3$ is hydrogen, $R_1$ is benzothipohene, and L is an alkylamino such as ethylamino. Compounds encompassed by these embodiments can be collectively represented by Formula If:

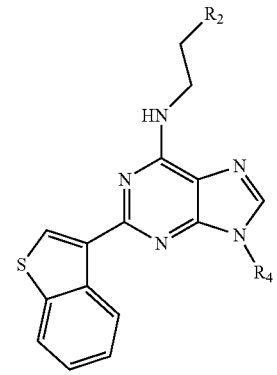

Formula If wherein:
$R_2$ is selected from a heteroaryl, preferably, 1H-indol-3-yl and aryl, preferably phenyl, each may optionally by substituted with hydroxy; and $R_4$ is selected from branched alkyl or alkaryl, preferably selected from isopropyl, sec-butyl, benzhydryl, and nonan-2-yl, and heteroalicyclic, preferably selected from oxetan-3-yl and tetrahydrofuran-3-yl.

Exemplary compounds encompassed by these embodiments include, but are not limited to:
4-(2-(2-(benzo[b]thiophen-3-yl)-9-isopropyl-9H-purin-6-ylamino)ethyl)phenol;
4-(2-(2-(benzo[b]thiophen-3-yl)-9-sec-butyl-9H-purin-6-ylamino)ethyl)phenol;
4-(2-(9-benzhydryl-2-(benzo[b]thiophen-3-yl)-9H-purin-6-ylamino)ethyl)phenol;
N-(2-(1H-indol-3-yl)ethyl)-2-(benzo[b]thiophen-3-yl)-9-isopropyl-9H-purin-6-amine;
4-(2-(2-(benzo[b]thiophen-3-yl)-9-(nonan-2-yl)-9H-purin-6-ylamino)ethyl)phenol;
N-(2-(1H-indol-3-yl)ethyl)-2-(benzo[b]thiophen-3-yl)-9-sec-butyl-9H-purin-6-amine;
4-(2-(2-(benzo[b]thiophen-3-yl)-9-(oxetan-3-yl)-9H-purin-6-ylamino)ethyl)phenol;
(S)-4-(2-(2-(benzo[b]thiophen-3-yl)-9-(tetrahydrofuran-3-yl)-9H-purin-6-yl amino)ethyl)phenol; and
(R)-4-(2-(2-(benzo[b]thiophen-3-yl)-9-(tetrahydrofuran-3-yl)-9H-purin-6-yl amino)ethyl)phenol.

In some embodiments, for any of the above-described embodiments of Formula Ia, $R_3$ is hydrogen, $R_1$ is a substituted or unsubstituted pyridine-3-yl, and L is an alkylamino such as ethylamino. Compounds encompassed by these embodiments can be collectively represented by Formula Ig:

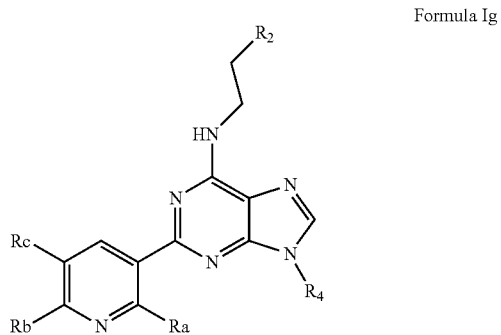

Formula Ig wherein:
$R_2$ is selected from a heteroaryl, preferably 1H-pyrrolo[2,3-b]pyridin-3-yl or 1H-indol-3-yl, which may optionally be substituted with 1 to 2 subsituents independently selected from halo, methyl and methoxy; and aryl, preferably phenyl, which may optionally be substituted with 1 to 2 subsituents independently selected from methyl, halo and hydroxy;
$R_4$ is selected from branched alkyl or alkaryl, preferably selected from isopropyl, sec-butyl, benzhydryl, and nonan-2-yl, and heteroalicyclic, preferably selected from oxetan-3-yl and tetrahydrofuran-3-yl; and
Ra, Rb and Rc are independently selected from hydrogen, cyano, methyl, halo, —$SO_2CH_3$ and trifluoromethyl.

Exemplary compounds encompassed by these embodiments include, but are not limited to:
4-(2-(9-isopropyl-2-(pyridin-3-yl)-9H-purin-6-ylamino) ethyl)phenol;
4-(2-(2-(6-fluoropyridin-3-yl)-9-isopropyl-9H-purin-6-ylamino)ethyl)phenol;
4-(2-(9-isopropyl-2-(4-methylpyridin-3-yl)-9H-purin-6-ylamino)ethyl)phenol;
5-(6-(4-hydroxyphenethylamino)-9-isopropyl-9H-purin-2-yl)nicotinonitrile;
4-(2-(9-isopropyl-2-(5-methylpyridin-3-yl)-9H-purin-6-ylamino)ethyl)phenol;
4-(2-(9-isopropyl-2-(5-(methylsulfonyl)pyridin-3-yl)-9H-purin-6-ylamino)ethyl)phenol;
4-(2-(2-(4-chloropyridin-3-yl)-9-isopropyl-9H-purin-6-ylamino)ethyl)phenol;
4-(2-(2-(5-fluoropyridin-3-yl)-9-isopropyl-9H-purin-6-ylamino)ethyl)phenol;
9-isopropyl-N-(2-(6-methoxy-1H-indol-3-yl)ethyl)-2-(pyridin-3-yl)-9H-purin-6-amine;
9-isopropyl-N-(2-(5-methyl-1H-indol-3-yl)ethyl)-2-(pyridin-3-yl)-9H-purin-6-amine;
N-(2-(1H-indol-3-yl)ethyl)-9-isopropyl-2-(pyridin-3-yl)-9H-purin-6-amine;
4-(2-(9-(oxetan-3-yl)-2-(pyridin-3-yl)-9H-purin-6-ylamino)ethyl)phenol;
4-(2-(9-(1-hydroxypropan-2-yl)-2-(pyridin-3-yl)-9H-purin-6-ylamino)ethyl)phenol;
4-(2-(2-(2-fluoropyridin-3-yl)-9-isopropyl-9H-purin-6-ylamino)ethyl)phenol;
5-(9-sec-butyl-6-(4-hydroxy-3-methylphenethylamino)-9H-purin-2-yl)nicotinonitrile;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino) ethyl)phenol;
5-(6-(2-(1H-indol-3-yl) ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)—N-(2-(1H-indol-3-yl)ethyl)-9-sec-butyl-2-(5-fluoropyridin-3-yl)-9H-purin-6-amine;
(S)—N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)—N-(2-(1H-indol-3-yl) ethyl)-9-sec-butyl-2-(5-methyl-pyridin-3-yl)-9H-purin-6-amine;
(S)—N-(2-(1H-indol-3-yl) ethyl)-9-sec-butyl-2-(5-methyl-pyridin-3-yl)-9H-purin-6-amine;
5-(6-(4-hydroxyphenethylamino)-9-(oxetan-3-yl)-9H-purin-2-yl)nicotinonitrile;
4-(2-(6-(5-fluoropyridin-3-yl)-1-isopropyl-1H-pyrazolo[3,4-d]pyrimidin-4-yl amino)ethyl)phenol;
3-(6-(4-hydroxyphenethylamino)-9-isopropyl-9H-purin-2-yl)isonicotinonitrile; 4-(2-(2-(5-fluoropyridin-3-yl)-7-isopropyl-7H-pyrrolo[2,3-d]pyrimidin-4-ylamino) ethyl) phenol;
4-(2-(9-isopropyl-2-(6-methylpyridin-3-yl)-9H-purin-6-ylamino)ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-fluoro-1H-indol-3-yl)ethyl)-9-isopropyl-2-(pyridin-3-yl)-9H-purin-6-amine;
N-(2-(5-chloro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino) ethyl)-2-methylphenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;

(R)—N-(2-(1H-indol-3-yl)ethyl)-2-(5-fluoropyridin-3-yl)-9-(tetrahydrofuran-3-yl)-9H-purin-6-amine;

4-(2-(6-(5-fluoropyridin-3-yl)-1-isopropyl-1H-imidazo[4,5-c]pyridin-4-yl amino)ethyl)phenol;

N-(2-(1H-indol-3-yl)ethyl)-2-(5-fluoropyridin-3-yl)-9-isopropyl-9H-purin-6-amine;

2-(5-fluoropyridin-3-yl)-9-isopropyl-N-(2-(6-methoxy-1H-indol-3-yl)ethyl)-9H-purin-6-amine;

2-(5-fluoropyridin-3-yl)-9-isopropyl-N-(2-(5-methoxy-1H-indol-3-yl)ethyl)-9H-purin-6-amine;

N-(2-(1H-indol-3-yl)ethyl)-2-(5-fluoropyridin-3-yl)-9-(prop-1-en-2-yl)-9H-purin-6-amine;

N-(2-(1H-pyrrolo[2,3-b]pyridin-3-yl)ethyl)-2-(5-fluoropyridin-3-yl)-9-isopropyl-9H-purin-6-amine;

4-(2-(5-(5-fluoropyridin-3-yl)-3-isopropyl-3H-imidazo[4,5-b]pyridin-7-yl amino)ethyl)phenol;

N-(2-(1H-indol-3-yl)ethyl)-9-isopropyl-2-(5-methylpyridin-3-yl)-9H-purin-6-amine;

2-(5-fluoropyridin-3-yl)-9-isopropyl-N-(2-(7-methyl-1H-indol-3-yl)ethyl)-9H-purin-6-amine;

N-(2-(1H-indol-3-yl)ethyl)-2-(5-fluoropyridin-3-yl)-9-(oxetan-3-yl)-9H-purin-6-amine;

N-(2-(1H-indol-3-yl)ethyl)-2-(5-methylpyridin-3-yl)-9-(oxetan-3-yl)-9H-purin-6-amine;

N-(2-(6-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(2-methyl-1H-indol-3-yl)ethyl)-9H-purin-6-amine;

2-(5-fluoropyridin-3-yl)-9-isopropyl-N-(2-(6-methyl-1H-indol-3-yl)ethyl)-9H-purin-6-amine;

N-(2-(4-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(4-methyl-1H-indol-3-yl)ethyl)-9H-purin-6-amine;

N-(2-(7-fluoro-1H-indol-3-yl)ethyl)-2-(5-fluoropyridin-3-yl)-9-isopropyl-9H-purin-6-amine; and 4-(2-(2-(5-fluoropyridin-3-yl)-9-(1-hydroxypropan-2-yl)-9H-purin-6-ylamino)ethyl)-2-methylphenol.

In some embodiments, the AHR antagonist has Formula Ia as depicted herein, wherein:

$R_3$ is hydrogen;

$R_1$ is selected from linear and branched alkyl, alkaryl, heteroalicyclic and aryl;

L is selected from substituted or unsubstituted alkylamino such as ethylamino and 1,ω-diaminoalkyl such as 1,2-diaminoethyl;

$R_2$ is selected from substituted or unsubstituted phenol, substituted or unsubstituted phenyl, substituted or unsubstituted heteroaryl such as, but not limited to, indole; and $R_4$ is selected from substituted or unsubstituted aryl and heteroaryl.

In some of these embodiments, $R_1$ is isopropyl and L, $R_2$ and $R_4$ are as defined herein.

In some of these embodiments, $R_1$ is sec-butyl and L, $R_2$ and $R_4$ are as defined herein.

$R_1$ is 2-nonyl and L, $R_2$ and $R_4$ are as defined herein.

In some of these embodiments, $R_2$ is phenol and L, $R_1$ and $R_4$ are as defined herein.

In some of these embodiments, $R_2$ is indole and L, $R_1$ and $R_4$ are as defined herein.

In some of these embodiments, $R_4$ is benzothiophene and L, $R_1$ and $R_2$ are as defined herein.

In some of these embodiments, $R_4$ is substituted or unsubstituted pyridine and L, $R_1$ and $R_2$ are as defined herein.

In some of these embodiments, L is a substituted or unsubstituted alkylamino such as ethylamino and $R_1$, $R_2$ and $R_4$ are as defined herein.

In some embodiments of any of the embodiments described herein for Formula If, $R_1$ is isopropyl, L is ethylamino, $R_2$ is phenol (substituting the second carbon atom in the ethyl moiety, $R_3$ is hydrogen and $R_4$ is benzothiophene.

A compound according to these embodiments is (4-(2-(2-(benzo[b]thiophen-3-yl)-9-isopropyl-9H-purin-6-ylamino) ethyl)phenol), and is also referred to herein and in the art as StemRegenin 1 or SR1.

StemReginin 1 has the following structure:

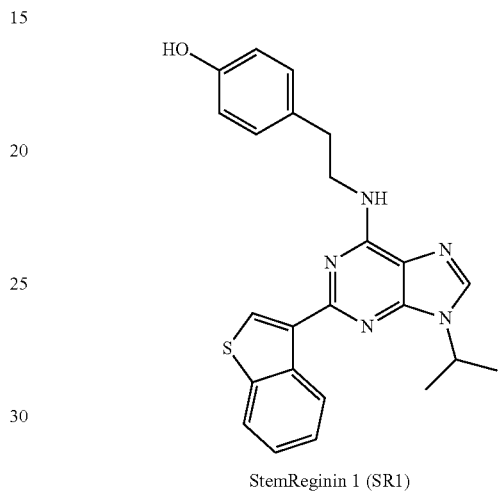

StemReginin 1 (SR1)

For any of the herein described AHR anyagonists, encompassed also are pharmaceutically acceptable salts, prodrugs, solvates, hydrates, and polymorphs thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more —NR—, —NH—, and —N=groups of the compound and one or more equivalents of an acid.

The acid addition salts may include a variety of organic and, inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Additional optional salts are described hereinbelow. Each of these acid addition salts can be either a mono-addition salt or a poly-addition salt, as these terms are defined herein.

In the context of some of the present embodiments, a pharmaceutically acceptable salt of the compounds described herein may optionally be a base addition salt comprising at least one group of the compound which is in a form of an anion, in combination with at least one counter ion (i.e., cation) that forms a pharmaceutically acceptable salt. Examples of suitable cations include metal cations of metals such as, but not limited to, sodium, potassium, magensium, and calcium or ammonium.

Each of these base addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be the AHR antagonist, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as polymorphs thereof, and further encompasses any pharmaceutically acceptable salts, prodrugs, solvates or hydrates of the stereoisomers and polymorphs.

As used herein, the term "amine" or "amino" describes both a —NR'R" group and a —NR'— group, wherein R' and R" can each independently be hydrogen, or substituted or unsubstituted alkyl, cycloalkyl, heteroalicyclic (bonded through a ring carbon), aryl or heteroaryl (bonded through a ring carbon). R' and R" are bound via a carbon atom thereof. Optionally, R' and R" are selected from hydrogen and alkyl comprising 1 to 4 carbon atoms. Optionally, R' and R" are hydrogen.

When one of R' and R" is an alkyl, the amino group is described herein as an aminoalkyl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine-oxide" or "N-oxide" describes a —N(OR')(R") or a —N(OR')— group, where R' and R" are as defined herein.

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a lower alkyl having 1 to 4 carbon atoms. The alkyl group may be substituted or unsubstituted, as indicated herein.

Herein, the term "alkyl" is also used to describe a group or a structural element of other groups, for example halo-substituted-alkyl and alkoxy, can be either straight-chained (linear) or branched. For example, alkyl includes methyl, ethyl, propyl, isopropyl, butyl, isobutyl, sec-butyl, t-butyl, etc.

$C_{1-4}$-alkoxy includes methoxy, ethoxy, and the like. Halo-substituted alkyl includes trifluoromethyl, pentafluoroethyl, and the like.

The term alkenyl, as used herein, describes an alkyl, as defined herein, which contains a carbon-to-carbon double bond.

The term alkynyl, as used herein, describes an alkyl, as defined herein, which contains carbon-to-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

Herein, the term "aryl" also means a monocyclic or fused bicyclic or tricyclic aromatic ring assembly containing six to 14 ring carbon atoms. For example, aryl may be phenyl or naphthyl, preferably phenyl. The term "arylene" means a divalent radical derived from an aryl group as defined herein.

As used herein, the term "heteroaryl" is also as defined for aryl where one or more of the ring members are a heteroatom or moiety selected from —O—, —N=, —NR—, —C(=O)—, —S—, —S(=O)— or —S(=O)$_2$—, wherein R is hydrogen, $C_{1-4}$alkyl or a nitrogen protecting group. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

Herein, the term "cycloalkyl" also means a saturated or partially unsaturated, monocyclic, fused bicyclic or bridged polycyclic ring assembly containing 3 to 20, or 3 to 16, or 3 to 12, or 3 to 10 ring atoms (optionally indicated). For example, $C_{3-10}$cycloalkyl includes cyclopropyl, cyclobutyl, cyclopentyl, cyclohexyl, etc.

Herein, the term "heterocycloalkyl" or "heteroalicyclic" also means cycloalkyl, as defined herein, provided that one or more of the ring carbons are replaced by a moiety selected from —O—, —N=., —NR—, —C(=O)—, —S—, —S(=O)— or —S(=O)$_2$—, wherein R is hydrogen, $C_{1-4}$alkyl or a nitrogen protecting group. For example, $C_{3-8}$heterocycloalkyl as used herein includes morpholino, pyrrolidinyl, piperazinyl, piperidinyl, piperidinylone, 2-Oxo-pyrrolidin-1-yl, 1,4-dioxa-8-aza-spiro[4.5]dec-8-yl, etc.

The term "piperazine" refers to a

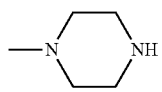

group or a

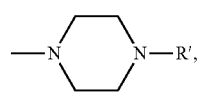

where R' as defined hereinabove.

The term "piperidine" refers to a

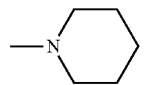

group.

The term "pyrrolidine" refers to a

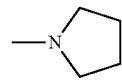

group.

The term "pyridine" refers to a

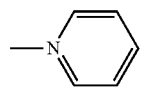

group.

The term "morpholine" refers to a

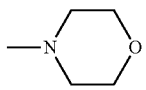

group, and encompasses also thiomorpholine.

The term "thiomorpholine" refers to a

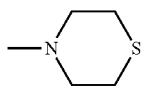

group.

The term "hexahydroazepine" refers to a

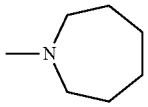

group.

Each of the alkyl, cycloalkyl, aryl, heteroaryl and heteroalicyclic groups described herein may be substituted by one or more substituents, whereby each substituent group can independently be, for example, halogen, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

Each of the cycloalkyl, aryl, heteroaryl and heteroalicyclic groups described herein can be connected to another group (for example, as indicated for $R_1$-$R_4$ in any of Formulae I and Ia-Ig herein) through any of its ring atoms.

For example, phenol can be connected to another group (for example to groups representing the variable L) via a carbon atom at the ortho, metal or para with respect to its OH group. Pyridine can be connected to another group (for example, as $R_4$) via a carbon atom at the ortho, para or meta position with respect to the nitrogen atom in its ring. A substituted pyridine can be connected to another group (for example, as $R_4$) via a carbon atom at the meta, ortho or para position with respect to the substituent. A benzothiophene can be connected to another group (for example, as $R_4$) via any carbon atom in its rings. Etc.

The term "phenol" describes a phenyl substituted by hydroxy.

The term "alkaryl" describes an alkyl substituted by one or more aryl, as defined herein. Examples include benzyl and benhydryl.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thio" describes a —S— group.

The term "thioalkoxy" describes both an —S-alkyl group, and a —S-cycloalkyl group, as defined herein.

The term "thioaryloxy" describes both an —S-aryl and a —S-heteroaryl group, as defined herein.

A "sulfinyl" group describes an —S(=O)—R' group, where R' is as defined herein.

A "sulfonyl" group describes an —S(=O)$_2$—R group, where Rx is as defined herein.

A "carbamyl" group describes an —OC(=O)—NR'R" group, where R' is as defined herein and R" is as defined for R'.

A "nitro" group refers to a —NO$_2$ group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "C-carboxylate" describes a —C(=O)—OR' or a —C(=O)—O—, where R' is as defined herein.

The term "O-carboxylate" describes a —OC(=O)R' or a —OC(=O)—, where R' is as defined herein.

The term "C-thiocarboxylate" describes a —C(=S)—OR' or a —C(=S)—O—, where R' is as defined herein.

The term "O-thiocarboxylate" describes a —OC(=S)R' or a —OC(=S)—, where R' is as defined herein.

The term "N-carbamate" describes an R"OC(=O)—NR'— or a —OC(=O)—NR'—, with R' and R" as defined herein.

The term "O-carbamate" describes an —OC(=O)—NR'R" or an —OC(=O)—NR'—, with R' and R" as defined herein.

The term "O-thiocarbamate" describes a —OC(=S)—NR'R" or a —OC(=S)—NR'—, with R' and R" as defined herein.

The term "N-thiocarbamate" describes an R"OC(=S)NR'— or a —OC(=S)NR'—, with R' and R" as defined herein.

The term "S-dithiocarbamate" describes a —SC(=S)—NR'R" or a —SC(=S)NR'—, with R' and R" as defined herein.

The term "N-dithiocarbamate" describes an R"SC(=S) NR'— or a —SC(=S)NR'—, with R' and R" as defined herein.

The term "urea", which is also referred to herein as "ureido", describes a —NR'C(=O)—NR"R'" or a —NR'C(=O)—NR"— group, where R' and R" are as defined herein and R'" is as defined herein for R' and R". The term "urea" is also referred to herein wherein each of R' and R" is hydrogen, whereby derivatives of urea are also defined as an urea in which one or more of R and R" is not hydrogen.

The term "thiourea", which is also referred to herein as "thioureido", describes a —NR'—C(=S)—NR"R'" or a —NR'—C(=S)—NR"—, with R', R" and R'" as defined herein.

The term "C-amide" describes a —C(=O)—NR'R" or a —C(=O)—NR'—, where R' and R" are as defined herein.

The term "N-amide" describes a R'C(=O)—NR"— or a R'C(=O)—N—, where R' and R" are as defined herein.

The term "guanyl" describes a R'R"NC(=N)— or a —R'NC(=N)-1, where R' and R" are as defined herein.

The term "guanidine" describes a —R'NC(=N)—NR"R'" or a —R'NC(=N)—NR"—, where R', R" and R'" are as defined herein.

The term "hydrazine" describes a —NR'—NR"R'" or a —NR'—NR"—, with R', R", and R'" as defined herein.

A "cyclic ring" encompasses an all-carbon ring structure, such as aryl or cycloalkyl, as defined herein, and further encompasses structures containing more than one ring (e.g., bicyclic structures).

A "heterocyclic ring" encompasses a ring structure that contains one or more heteroatoms such as nitrogen, oxygen, sulfur, and the like, such as heteroalicyclic and heteroaryl, as defined herein, and further encompasses structures containing more than one ring (e.g., bicyclic structures).

In any of the embodiments described herein, the AHR antagonist can be a commercially available compound (e.g., SR1) and can thus be obtained from commercial vendors, or, it can be prepared by methods known in the art.

Exemplary processes for preparing an AHR antagonist as described herein are provided in the following.

In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

The following reaction schemes 1-5 describe exemplary processes of preparing the AHR antagonists as described herein. It will be appreciated by one skilled in the art that, following introduction by the methods detailed below, any of the groups $R_1$, $R_2$, $R_3$, $R_4$, and $L_1$ may optionally be further elaborated by known transformations to arrive at the desired final compounds of Formula I.

Compounds of Formula I can be prepared according the following Reaction Scheme 1:

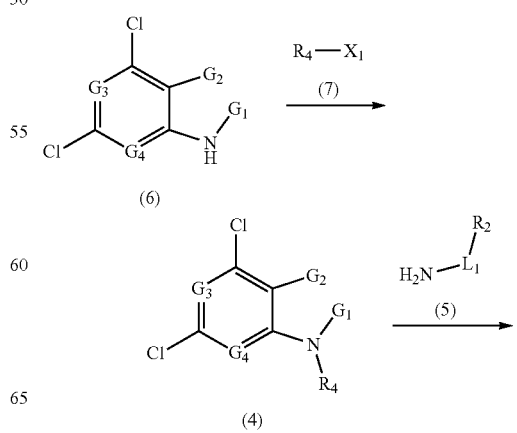

Reaction Scheme 1

-continued

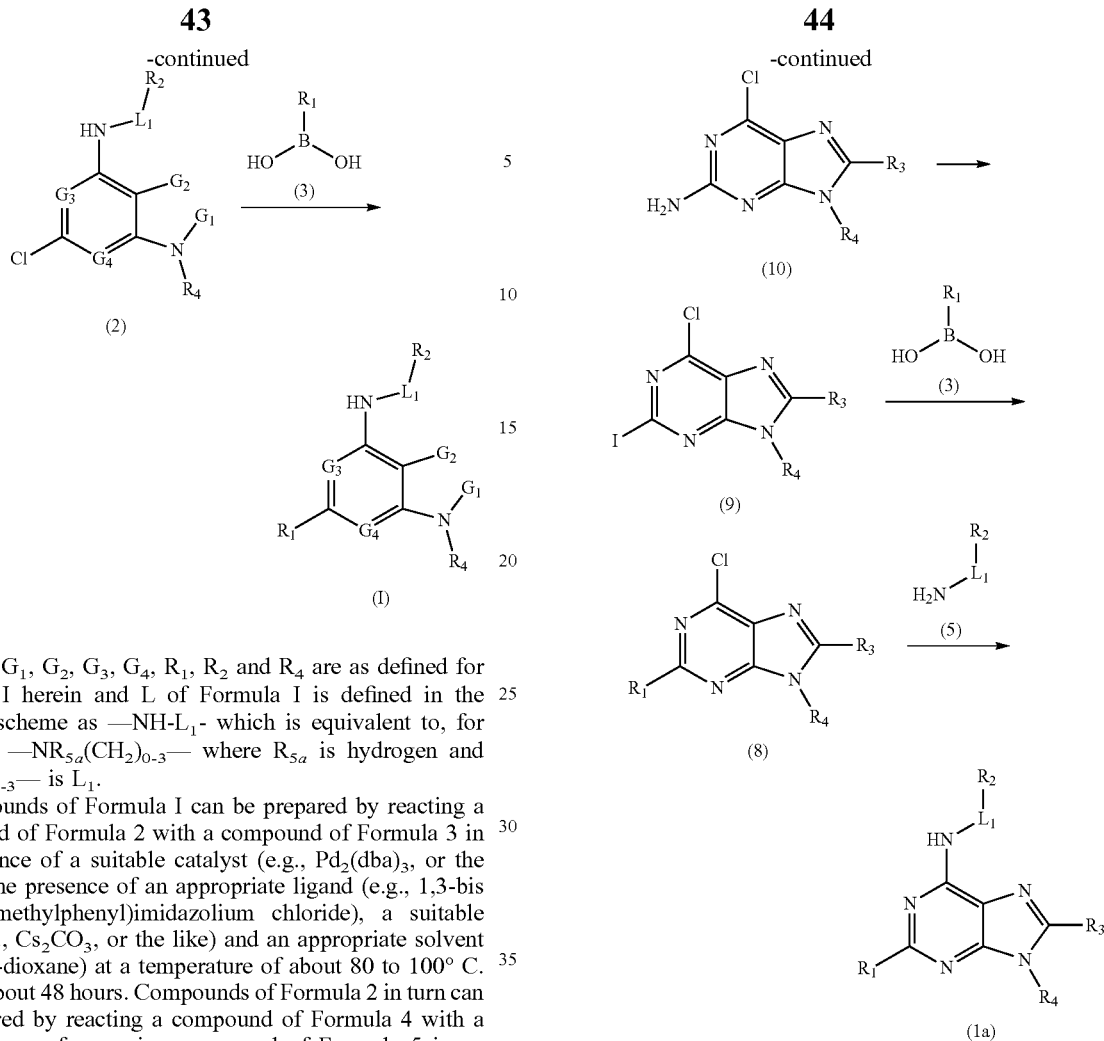

in which $G_1$, $G_2$, $G_3$, $G_4$, $R_1$, $R_2$ and $R_4$ are as defined for Formula I herein and L of Formula I is defined in the reaction scheme as —NH-$L_1$- which is equivalent to, for example, —N$R_{5a}$(CH$_2$)$_{0-3}$— where $R_{5a}$ is hydrogen and —(CH$_2$)$_{0-3}$— is $L_1$.

Compounds of Formula I can be prepared by reacting a compound of Formula 2 with a compound of Formula 3 in the presence of a suitable catalyst (e.g., Pd$_2$(dba)$_3$, or the like) in the presence of an appropriate ligand (e.g., 1,3-bis (2,4,6-trimethylphenyl)imidazolium chloride), a suitable base (e.g., Cs$_2$CO$_3$, or the like) and an appropriate solvent (e.g., 1,4-dioxane) at a temperature of about 80 to 100° C. for 2 to about 48 hours. Compounds of Formula 2 in turn can be prepared by reacting a compound of Formula 4 with a slight excess of an amine compound of Formula 5 in an appropriate solvent (e.g. isopropanol) at a temperature of about room temperature to about 80° C. Compounds of Formula 4 can be prepared by alkylation of a compound of Formula 6 with a suitable alkylating agent 7, in which $X_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol $R_4$—OH in the presence of a suitable phosphine (e.g. triphenylphosphine) and azodicarboxylate (e.g. diethylazodicarboxylate), in an inert solvent such as THF or toluene, at a temperature from about 0° C. to about room temperature.

Compounds of Formula Ia, in which $G_1$ is $CR_3$ and in which all other G groups are N, can also be prepared by proceeding as in the following Reaction Scheme 2:

Reaction Scheme 2

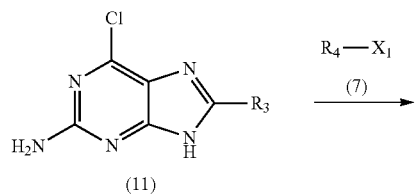

in which $R_1$, $R_2$, $R_3$ and $R_4$ are as defined for Formula I herein and L of Formula I is defined in the reaction scheme as —NH-$L_1$- which is equivalent to, for example, —N$R_{5a}$ (CH$_2$)$_{0-3}$— where $R_{5a}$ is hydrogen and —(CH$_2$)$_{0-3}$— is $L_1$.

Compounds of Formula I can be prepared by reacting a compound of Formula 8 with an amine compound of Formula 5 in an appropriate solvent (e.g. isopropanol) at a temperature of about room temperature to about 100° C. Compounds of Formula 8 can in turn be prepared by reacting a compound of Formula 9 with a compound of Formula 3 in the presence of a suitable catalyst (e.g., Pd(Ph$_3$P)$_4$, Pd$_2$ (dba)$_3$, or the like), optionally in the presence of an appropriate ligand (e.g., 1,3-bis(2,4,6-trimethylphenyl)imidazolium chloride), a suitable base (e.g., Cs$_2$CO$_3$, or the like) and an appropriate solvent (e.g., 1,4-dioxane) at a temperature of about 80 to 100° C. for 2 to about 48 hours. Compounds of Formula 9 in turn can be prepared by reacting a compound of Formula 10 with a mixture of di-iodomethane, copper(I) iodide, and an alkyl nitrite (e.g. isoamylnitrite), optionally in the presence of an inert solvent, at a temperature of about 50 to 100° C. Compounds of Formula 10 can be prepared by alkylation of a compound of Formula 11 with a suitable alkylating agent 7, in which $X_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol $R_4$—OH in the presence of a suitable phosphine (e.g. triphenylphosphine)

and azodicarboxylate (e.g. diethylazodicarboxylate), in an inert solvent such as THF or toluene, at a temperature from about 0° C. to about room temperature.

Compounds of Formula II, which are a subset of compounds of Formula I in which $R_1$ is N-linked heterocyclyl or N-linked heteroaryl, can be prepared as detailed in the following Reaction Scheme 3:

Reaction Scheme 3

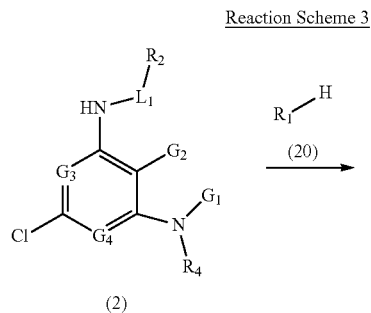

With $G_1$, $G_2$, $G_3$, $G_4$, $R_1$, $R_2$ and $R_4$ are as defined for Formula I herein and L of Formula I is defined in the reaction scheme as —NH-$L_1$- which is equivalent to, for example, —NR$_{5a}$(CH$_2$)$_{0-3}$— where $R_{5a}$ is hydrogen and —(CH$_2$)$_{0-3}$— is $L_1$. Compounds of Formula II can be prepared by reacting a compound of Formula 2 with a compound of Formula 20 in the presence of an excess of cyclic amine or NH-bearing heterocycle (for example, substituted pyrazole, substituted imidazole, and the like), at a temperature of about 50° C. to about 250° C., for about 1 to about 24 hours, optionally in the presence of a base such as sodium hydride or DBU.

Compounds of Formula 10 in which $G_1$ is CR$_3$, and in which all other G groups are N, can also be prepared by proceeding as in the following Reaction Scheme 4:

Reaction Scheme 4

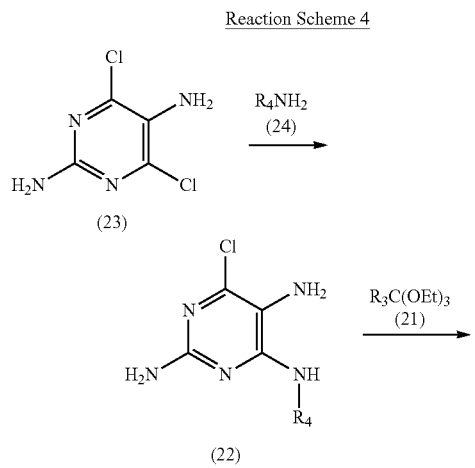

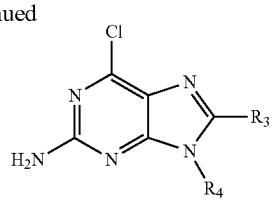

in which $R_3$ and $R_4$ are as defined for Formula I herein. Compounds of Formula 10 can be prepared according to procedures described in J. Med. Chem., 1972, 456, and J. Med. Chem., 1992, 3380. An orthoester compound of Formula 21 is reacted with a compound of Formula 22, optionally in the presence of an acid such as acetic acid, at a temperature of about room temperature to about 150° C., for about 1 to about 24 hours. A compound of Formula 22 can in turn be prepared by reacting a compound of Formula 23 with a primary amine compound of Formula 24, optionally in the presence of an acid such as pTSA, or a base such as triethylamine or DBU, at a temperature of about 50 to about 200° C.

Compounds of Formula IV can be prepared as detailed in the following Reaction Scheme 5:

Reaction Scheme 5

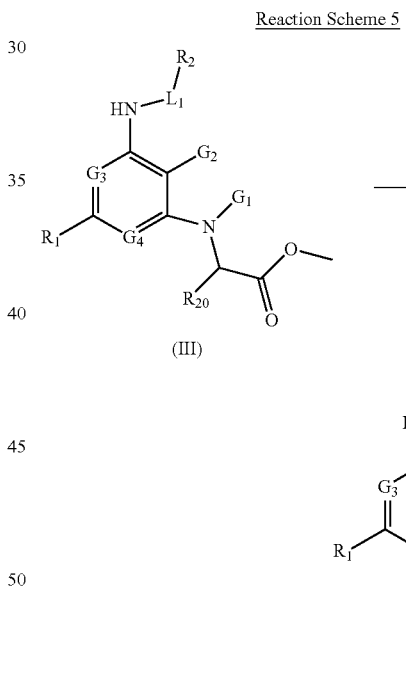

in which $G_1$, $G_2$, $G_3$, $G_4$, $R_1$ and $R_2$ are as defined for Formula I herein and L of Formula I is defined in the reaction scheme as —NH-$L_1$- which is equivalent to, for example, —NR$_{5a}$(CH$_2$)$_{0-3}$— where $R_{5a}$ is hydrogen and —(CH$_2$)$_{0-3}$— is $L_1$. $R_{20}$ and $R_{21}$ are independently selected from hydrogen and $C_{1-4}$alkyl. A compound of Formula IV, in which $R_{21}$ is hydrogen, can be prepared from a compound of Formula III by treatment with a suitable reducing agent such as lithium aluminum hydride or di-isobutyl aluminum hydride, in a suitable solvent such as THF or toluene, at a temperature of about −78° C. to about 50° C. The reaction takes about 0.5 to about 16 hours to complete. A compound of Formula IV, in which $R_{21}$ is lower alkyl, can be prepared by treatment of a compound of Formula III with an alkyl lithium or Grignard reagent, in a suitable solvent such as ether or tetrahydrofuran, at a temperature of about −78° C. to about 50° C. The reaction takes about 0.5 to about 16 hours to complete.

Any of the AHR antagonists as described herein can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds as described herein can be prepared using salts of the starting materials or intermediates.

For example, salt forms of 4-(2-(2-(benzo[b]thiophen-3-yl)-9-isopropyl-9H-purin-6-ylamino)ethyl)phenol (SR1) can be synthesized as follows:

Mesylate salt: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 50° C. Methanesulfonic acid (0.137 gram; 1.40 mmoles) is added drop wise. The crystallization takes place rapidly. The white suspension is allowed to cool over about 30 minutes with cooling to room temperature. The slurry is stirred for 18 hours at room temperature and filtered. The solid is washed with acetone (6 ml) in three portions and dried first for about 3 hours at 50° C./about 10 mbar and then for about 16 hours at 80° C./about 10 mbar. The material has a melting point at about 233° C. with a melting enthalpy of 98 g/J.

In another embodiment, a mesylate salt of SR1 is prepared. In a further embodiment, the mesylate salt of SR1 comprisES the following powder X-ray diffraction peaks (Angle 2-θ°): 6.4, 6.7, 18.3, 18.6, 26.9; and which in an additional embodiment comprises the following powder X-ray diffraction peaks (Angle 2-θ°): 6.4, 6.7, 10.3, 12.9, 16.4, 18.3, 25.8, 26.5, 26.9.

The tosylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml at 50° C. A solution of para-toluenesulfonic acid mono-hydrate (0.271 gram; 1.40 mmoles) in acetone (1.2 ml) is added drop wise. The solution is seeded at 50° C. and crystallization takes place quickly. The suspension is allowed to cool over about 30 minutes to room temperature and stirred for about 18 hours. After filtration the solid is washed with acetone (6 ml) in three portions and dried first for about 3 hours at 50° C./about 10 mbar and then for about 16 hours at 80° C./about 10 mbar. The material has a melting point at about 233° C. with a melting enthalpy of 88 g/J.

In another embodiment, a tosylate salt of R1 is prepared. In a further embodiment, the tosylate salt of SR1 comprisES the following powder X-ray diffraction peaks (Angle 2-θ°): 6.2, 13.3, 16.7, 19.5, 25.4; and which in an additional embodiment comprises the following powder X-ray diffraction peaks: 6.2, 7.6, 12.4, 13.3, 15.1, 16.7, 17.7, 19.5, 20.2, 24.6, 24.9, 25.4, 25.6.

The sulfate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 10 ml acetone and 1 ml water at about 55° C. A solution of sulfuric acid (0.280 gram; 2.79 mmoles) in 1 ml water is added drop wise. The crystallization takes place rapidly. The suspension is allowed to cool over about 30 minutes with cooling to room temperature, stirred for about 18 hours and filtered. The filter cake is washed with 6 ml acetone in three portions and dried first for about 3 hours at 50° C./about 10 mbar and then for about 16 hours at 80° C./about 10 mbar. The material has a melting point at about 224° C. with a melting enthalpy of 91 g/J.

In another embodiment, the sulfate salt of SR1 comprises the following powder X-ray diffraction peaks (Angle 2-θ°): 6.5, 6.8, 10.7, 13.5, 26.4, 27.6; and which in an additional embodiment comprises the following powder X-ray diffraction peaks (Angle 2-θ°): 6.5, 6.8, 10.7, 13.1, 13.5, 18.6, 18.8, 20.8, 26.4, 27.1, 27.6.

The esylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 50° C. Ethanesulfonic acid (0.155 gram; 1.40 mmoles) is added drop wise. The crystallization takes place quickly. The resulting white suspension is allowed to cool over about 30 minutes to room temperature. The suspension is stirred for about 18 hours at room temperature and filtered. The solid is washed with 6 ml acetone in three portions and dried first for about 3 hours at 50° C./about 10 mbar and then for about 16 hours at 80° C./about 10 mbar. The material has a melting point at about 231° C. with a melting enthalpy of 76 g/J.

In another embodiment, the i esylate salt of SR1 comprises the following powder X-ray diffraction peaks (Angle 2-θ°): 6.3, 9.9, 18.4, 25.3, 26.1; and which in an additional embodiment comprises the following powder X-ray diffraction peaks (Angle 2-θ°): 6.3, 9.9, 17.1, 17.9, 18.4, 19.0, 22.0, 25.3, 26.1, 27.1.

The hydrobromide salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 6 ml DMF at 65° C. Hydrobromic acid 48% (0.235 gram; 1.40 mmoles) is added drop wise. The solution is allowed to cool over about 30 minutes to room temperature. Seeds are added at 55° C. and crystallization takes place slowly. The suspension is stirred for about 18 hours at room temperature and filtered. The solid is washed with 4 ml DMF/water 1:1 and 6 ml water. The salt is dried as described herein for the other salts. The material has a melting point at about 285° C. with a melting enthalpy of 119 g/J.

In another embodiment, the i hydrobromide salt of SR1 comprises the following powder X-ray diffraction peaks (Angle 2-θ°): 7.0, 25.9, 26.8, 27.9; and which in an additional embodiment comprises the following powder X-ray diffraction peaks (Angle 2-θ°): 7.0, 11.4, 13.3, 21.4, 23.4, 25.9, 26.4, 26.8, 27.9.

The orotate salt of SR1 is prepared as follows: 4-(2-(2-(benzo[b]thiophen-3-yl)-9-isopropyl-9H-purin-6-ylamino) ethyl)phenol free base (0.60 gram; 1.40 mmoles) and orotic acid (0.222 gram; 1.40 mmoles) are dissolved in 7.8 ml NMP (1-Methyl-2-pyrrolidone) at 85° C. The solution is cooled to 60° C. and 6 ml water is added drop wise over about 5 minutes. The resulting white suspension is allowed to cool over about 30 minutes to room temperature and stirred for 18 hours. After filtration the filter cake is washed with 4 ml NMP/water 1:1 in two portions and 6 ml water in three portions. The solid is dried as described herein for other salts. The material has a melting point at about 240° C. with a melting enthalpy of 130 g/J.

In another embodiment, the i orotate salt of SR1 comprises the following powder X-ray diffraction peaks (Angle 2-θ°): 7.1, 16.3, 19.2, 23.5, 25.6, 26.9; and which in an additional embodiment comprises the following powder X-ray diffraction peaks (Angle 2-θ°): 7.1, 14.4, 16.3, 18.6, 19.2, 21.7, 23.0, 23.5, 25.6, 26.9, 28.7.

The hemi-fumarate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 18 ml methanol at 65° C. Fumaric acid (0.164 gram; 1.40 mmoles) and 6 ml methanol are added. The solution is allowed to cool over about 30 minutes to room temperature. Some seed crystals are added at 60° C. and crystallization takes place slowly. The suspension is stirred for 18 hours at room temperature and filtered. The solid is washed with 6 ml methanol in three portions and dried as described herein for the other salts. The material has a melting point at about 223° C. with a melting enthalpy of 83 g/J.

In another embodiment, the hemi-fumarate salt of SR1 comprises the following powder X-ray diffraction peaks (Angle 2-θ°): 7.2, 8.7, 14.4, 15.8, 17.4, 19.0, 23.7; and which in an additional embodiment comprises the following powder X-ray diffraction peaks (Angle 2-θ°): 7.2, 8.7, 10.8, 14.4, 15.8, 17.4, 17.8, 19.0, 20.1, 23.7, 27.5.

The besylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 50° C. A solution of benzenesulfonic acid (0.225 gram; 2.79 mmoles) in 1.2 ml acetone is added drop wise. Seed crystals are added at 48° C. and the crystallization takes place slowly. The suspension is allowed to cool over about 30 minutes to room temperature. The slurry is stirred for about 18 hours at room temperature and filtered. The salt is washed with 6 ml acetone in three portions and dried as described herein for other salts. The material has a melting point at about 219° C. with a melting enthalpy of 92 g/J.

In another embodiment, the besylate salt of SR1 comprises the following powder X-ray diffraction peaks (Angle 2-θ°.): 6.2, 7.7, 17.7, 25.5; and which in an additional embodiment comprises the following powder X-ray diffraction peaks (Angle 2-θ°): 6.2, 7.7, 15.2, 16.7, 17.1, 17.7, 19.8, 20.2, 24.9, 25.2, 25.5.

The napadisylate salt of SR1 can be prepared as follows: 4-(2-(2-(benzo[b]thiophen-3-yl)-9-isopropyl-9H-purin-6-ylamino)ethyl)phenol free base (0.60 gram; 1.40 mmoles) and 0.259 gram 1,5-naphthalenedisulfonic acid (0.70 mmoles) are dissolved in 9 ml DMF at 87° C. The clear solution is allowed to cool over about 30 minutes to room temperature. Seeds are added at 65° C. and crystallization takes place slowly. The suspension is stirred for about 18 hours at room temperature and filtered. The solid is washed with 4 ml DMF/water 1:1 in two portions and 6 ml water in three portions. The salt is dried as described herein for other salts. The material has a melting point at about 304° C. with a melting enthalpy of 83 g/J. A broad endothermic phenomenon is observed at 107° C. that might be attributed to the loss of water.

In another embodiment, the napadysilate salt of SR1 comprises the following powder X-ray diffraction peaks (Angle 2-θ°): 6.4, 9.6, 13.1, 15.7, 16.1, 26.0; and which in an additional embodiment comprises the following powder X-ray diffraction peaks (Angle 2-θ°): 9.6, 13.1, 15.7, 16.1, 16.4, 20.4, 20.9, 23.7, 26.0, 26.9.

The hydrochloride salt of SR1 is prepared as follows: 4-(2-(2-(benzo[b]thiophen-3-yl)-9-isopropyl-9H-purin-6-ylamino)ethyl)phenol free base (0.60 gram; 1.40 mmoles) are dissolved in 12 ml acetone at 55° C. Hydrochloric acid 37% (0.138 gram; 1.40 mmoles) is added drop wise. The crystallization takes place quickly. The white suspension is allowed to cool over about 30 minutes to room temperature and stirred for 18 hours. After filtration the solid is washed with 6 ml acetone in three portions and dried as described herein for the other salts. The material is exhibiting an exothermic event at about 162° C. with an enthalpy of −13.8 J/g. This phenomenon might be attributed to a solid transformation into a more stable modification. An endothermic event is then seen at about 259° C. with an enthalpy of 99.7 J/g.

In another embodiment, the hydrochloride salt of SR1 comprises the following powder X-ray diffraction peaks (Angle 2-θ°): 6.1, 7.0, 19.8, 26.1; and which in an additional embodiment comprises the following powder X-ray diffraction peaks (Angle 2-θ°): 6.1, 7.0, 18.1, 19.8, 24.7, 26.1, 27.0, 27.7.

free acid or free base forms of the AHR antagonists as described herein can be prepared from the corresponding base addition salt or acid addition salt form, respectively. For example, an AHR antagonist in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc.). The nitrate salt of SR1 can be made using methods known to the skilled person.

AHR antagonists in unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the AHR antagonists as described herein can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the AHR antagonists as described herein can be made by means known to those of ordinary skill in the art. A detailed description of techniques applicable to the creation of protecting groups and their removal can be found in T. W. Greene, "Protecting Groups in Organic Chemistry", 3.sup.rd edition, John Wiley and Sons, Inc., 1999.

The AHR antagonists as described herein can be conveniently prepared as solvates (e.g., hydrates). Hydrates of the AHR antagonists as described herein can be conveniently prepared by recrystallization from an aqueous/organic solvent mixture, using organic solvents such as dioxin, tetrahydrofuran or methanol.

The AHR antagonists as described herein can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981. Compounds of the invention can also be prepared as their individual stereoisomers by using chiral chromatography techniques, in particular, by use of HPLC or SFC chromatography using a chiral stationary phase.

In summary, the AHR antagonists as described herein can be made by a process, which involves:

(a) those of reaction schemes 1-5; and (b) optionally converting a AHR antagonist as described herein into a pharmaceutically acceptable salt;

(c) optionally converting a salt form of an AHR antagonist as described herein to a non-salt form;

(d) optionally converting an unoxidized form of an AHR antagonist as described herein into a pharmaceutically acceptable N-oxide;

(e) optionally converting an N-oxide form of the AHR antagonist to its unoxidized form;

(f) optionally resolving an individual isomer of an AHR antagonist as described herein from a mixture of isomers;

(g) optionally converting a non-derivatized AHR antagonist as described herein into a pharmaceutically acceptable prodrug derivative; and (h) optionally converting a prodrug derivative of an AHR antagonist as described herein to its non-derivatized form.

Insofar as the production of the starting materials is not particularly described, the compounds are known or can be prepared analogously to methods known in the art.

In another embodiment, an agent capable of down-regulating the activity and/or expression of aryl hydrocarbon receptor is an antisense oligonucleotide or a small interfering RNA molecule (siRNA), capable of down-regulating AHR protein expression or the protein expression of one or more down-stream effectors of AHR.

Design of antisense oligonucleotides which can be used to efficiently inhibit the AHR protein expression must be effected in a way that such oligonucleotides specifically bind the designated mRNA within cells in a way which inhibits translation thereof. Sequence suitable for use in design and synthesis of antisense oligonucleotides which specifically bind to AHR mRNA, genomic DNA and/or its promoter or other control sequences are available in published sequence of AHR, in particular human AHR. In addition, algorithms for identifying sequences with the highest predicted binding affinity for their target mRNA based on thermodynamic cycle that accounts for the energetics of structural alterations in both the target mRNA and the oligonucleotides are also available.

Synthesis of RNAi molecules suitable for in the context of the present embodiments can be affected as follows: First, the AHR mRNA sequence (or one or more of its downstream effectors) is scanned downstream of the AUG start codon for AA-dinucleotide sequences. Occurrence of each AA and the 19 3'-adjacent is recorded as a potential siRNA target site. Then, potential target sites are compared to an appropriate genomic database (e.g, human, mouse, rat, etc.) using any sequence alignment software. Putative target site that exhibit significant homology to other coding sequences are filtered out. Preferred sequences are then those including low G/C content, in particular sequences with G/C content lower than 55%. Several target sites are then selected along the length of the target gene. Methods or algorithms to identify putative target site of siRNA are described for example in (Tilesi, et al., Curr. Opin. Mol. Ther. 11:156, 2009).

Examples of siRNA molecules which are capable of down-regulating the expression of AHR include, but are not limited to, AHR 111S, 5' GCG GCA TAG AGA CCG ACT TAA TTT CAA GAG AAT TAA GTC GGT CTC TAT GCC GCT TTT TTG G 3' (SEQ ID NO: 1); AHR 111AS, 5' CGC GCC AAA AAA GCG GCA TAG AGA CCG ACT TAA TTC TCT TGA AAT TAA GTC GGT CTC TAT GCC GC 3' (SEQ ID NO: 2); AHR 242S, 5' GGC TTC TTT GAT GTT GCA TTA ATT CAA GAG ATT AAT GCA ACA TCA AAG AAG CCT TTT TTG G 3' (SEQ ID NO: 3); AHR 242AS, 5' CGC GCC AAA AAA GGC TTC TTT GAT GTT GCA TTA ATC TCT TGA ATT AAT GCA ACA TCA AAG AAG CC 3' (SEQ ID NO: 4).

According to a specific embodiment the AHR antagonist, e.g., SR1 is supplied to the medium at a concentration range of 10-2500, 500-2500, 100-2500, 100-1500, 100-1000, 200-2000 or 100-2000 nM.

According to a specific embodiment the AHR antaogonist, e.g., SR1 is supplied to the medium at a concentration range of 100-1000 nM.

According to a specific embodiment the SR1 is supplied to the medium at a concentration range of 100-500 nM.

As mentioned, other factors may be added to the culture medium.

The addition of other factors may be in the presence of the aryl hydrocarbon receptor antagonist or in its absence, e.g., the medium comprising the antagonist is replaced to a fresh medium which doesn't include the antagonist, but includes nicotinamide and optionally FGF4. Alternatively and as mentioned, all the factors are included in the same medium.

As used herein "nicotinamide" refers to nicotinamide as well as to products that are derived from nicotinamide, analogs thereof and metabolites of nicotinamide or nicotinamide analogs, such as, for example, NAD, NADH and NADPH.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid, α-amino-3-indolepropionic acid, and inhibitors of sirtuin family of histone/protein deacetylases.

Examples of nitotinamide analog derivatives include, but are not limited to substituted benzamides, substituted nicotinamides and nicotinethioamides and N-substituted nicotinamides and nicotinthioamides.

In a particular embodiment, the nicotinamide is supplied at a concentration of at least about 1 mM to 20 mM. In other embodiment, the nicotinamide concentration is supplied at a concentration of at least about 1 mM to 10 mM, e.g. about 5 mM.

Fibroblast growth factor 4, the FGF4 (map locus 11q13.3) gene product, FGF-4/HBGF-4/KFGF, is a 176 AA long protein derived by cleavage of the N-terminal 30 AAs of the precursor protein. FGF-4 contains a single N-linked glycosylation site. Unglycosylated FGF-4 is cleaved into two NH2-terminally truncated peptides (13 and 15 kDa) that are more active with higher heparin affinity than wild-type protein.

According to a particular embodiment, the FGF4 is human FGF4.

Recombinant FGF4 protein is commercially available (e.g. from Sigma Aldrich, where it is produced in baculovirus and cleaved at the N-terminal to yield a 148 AA protein; or from Invitrogen where it is produced in *E. coli*).

In a particular embodiment, the FGF4 is supplied at a concentration of at least about 1-1000 ng/ml. In other embodiment, the FGF4 concentration is supplied at a concentration of at least about 10-100 ng/ml, e.g. about 50 ng/ml.

According to a particular embodiment, the culturing medium comprising both nicotinamide and FGF4 is devoid of additional growth factors such as PDGF, HB-EGF or bFGF.

It will be appreciated that when referring to a medium being devoid of a particular component, the present invention contemplates that the medium comprises this component, but at a concentration which is below its minimal activity on mesenchymal stem cells. Thus, for example, certain media may comprise trace amounts of the above described growth factors, however, the methods of the present invention relate to a medium being devoid of exogenously added growth factor beyond what is included in a commercial medium's formula, or that resulting from overall adjustment of medium component concentrations. Thus, according to a particular embodiment, the medium which comprises nicotinamide and FGF4 may comprise any one of the above mentioned additional growth factors but at a concentration less than 1 ng/ml.

The nicotinamide and/or growth factor are added to the medium (typically the same medium as including the aryl hydrocarbon receptor antagonist, as described above).

It will be noted that many of the culture media contain nicotinamide as a vitamin supplement for example, MEMα (8.19 μM nicotinamide), RPMI (8.19 μM nicotinamide), DMEM (32.78 μM nicotinamide) and Glasgow's medium (16.39 μM nicotinamide), however, the methods of the present invention relate to exogenously added nicotinamide supplementing any nicotinamide and/or nicotinamide moiety included the medium's formula, or that resulting from overall adjustment of medium component concentrations.

In an embodiment of the invention, the cell culture medium has a high calcium concentration of more than about 1.8 mM, more than about 2 mM, or more than about 5 mM. It will be appreciated that the calcium concentration is calculated as the total calcium concentration including that already present in the culture medium.

Thus, for example, if the medium is Dulbecco's modified MEM (DMEM) (which already has a calcium ion concentration of about 1.8 mM), no additional calcium needs to be added. If the cell medium is Ham's F12 which has a calcium ion concentration of about 0.9 mM, additional calcium should be added so the total calcium concentration is above 1.8 mM. In one embodiment, the source of the additional calcium may be serum.

During the culturing, the medium can contain supplements required for cellular metabolism such as glutamine and other amino acids, vitamins, minerals and useful proteins such as transferrin, and the like. The medium may also contain antibiotics to prevent contamination with yeast, bacteria, and fungi, such as penicillin, streptomycin, gentamicin, and the like. If cells are to be cultured, conditions should be close to physiological conditions (preferably, a pH of about 6 to about 8, and a temperature of about 30° C. to about 40° C.).

Normoxia or hypoxia conditions are also contemplated.

The culturing according to this aspect of the present invention may be effected for a limited amount of time, such that no expansion takes place (e.g. during the seeding stage only) or may be effected for longer periods of time so as to allow for mesenchymal stem cell expansion (i.e. cell propagation), thereby obtaining increased quantities thereof.

For each round of propagation, adherent cells may be harvested using trypsin/EDTA or by cell scraping, and dissociated by passage through a narrow Pasteur plastic pipette, and preferably replated at a density of about 100 to about 10,000 cells/cm$^2$.

According to this aspect of the present invention, a period of time sufficient for cell expansion may be taken to mean the length of time required for at least one cell to divide.

According to one embodiment, the culturing is effected for at least one day, at least two days, at least three days, at least four days, at least five days, at least six days, at least one week, at least two weeks, at least three weeks, at least four weeks or at least five weeks.

According to another embodiment, the culturing is not effected for more than ten weeks.

According to still another embodiment, the cells are allowed to expand for at least two population doublings, at least four population doublings, at least six population doublings, at least eight population doublings, at least ten population doublings, at least 15 population doublings, at least 20 population doublings, at least 25 population doublings, at least 30 population doublings, at least 35 population doublings, at least 40 population doublings, or at least 45 population doublings.

According to another embodiment, the cells are not allowed to expand for more than 50 population doublings.

According to a further aspect of the invention there is provided a method of expanding a population of mesenchymal stem cells. The method comprising culturing a seeded population of mesenchymal stem cells for a period of time sufficient for cell expansion, wherein said culturing is in a medium comprising an aryl hydrocarbon receptor antagonist, thereby generating an expanded population of mesenchymal stem cells.

It will be appreciated that this method too can be effected in the presence of nicorinamide and FGF4.

According to a specific embodiment, at least a portion of the period of time the culturing is effected in a medium devoid of nicotinamide; and for at least a second portion of the period of time, the culturing is effected in a medium comprising nicotinamide and FGF4, thereby generating an expanded population of mesenchymal stem cells.

The term "expanding" as used herein refers to increasing the number of cells in the cell population due to cell replication.

The seeded population of undifferentiated mesenchymal stem cells may be a heterogeneous population of cells or a purified population of mesenchymal stem cells, as further described herein above.

As mentioned, a medium being devoid of nicotinamide refers to a medium comprising less than the minimal effective amount of nicotinamide (e.g. less than 0.5 mM, or more preferably less than 0.05 mM). Thus mediums comprising trace amounts of nicotinamide (as described herein above) may be used for this aspect of the present invention.

According to one embodiment, the MSCs are at least 50% purified, at least 75% purified or at least 90% purified (e.g., 90% MSCs and 10% other cells e.g., blood cells).

The population of mesenchymal stem cells may be seeded (and also cultured) in any medium including those described herein above or those disclosed in U.S. Patent Application No. 20050260748, incorporated herein by reference.

The time ratio of culturing in the presence of nicotinamide and FGF4: culturing in the absence of nicotinamide may vary and may include all ratios from 1:99; 2:98; 3:97; 4:96; 5:95; 6:94; 7:93; 8:92; 9:91; 10:90; 11:89; 12:88; 13:87; 14:86; 15:85; 16:84; 17:83; 18:82; 19:81; 20:80; 21:79; 22:78; 23:77; 24:76; 25:75; 26:74 27:73; 28:72; 29:71; 30:70; 31:69; 32:68; 33:67; 34:66; 35:65; 36:64; 37:63; 38:62; 39:61; 40:60; 33:59; 42:58; 43:57; 44:56; 45:55; 46:54; 47:53; 48:52; 49:51; 50:50; 51:49; 52:48; 53:47; 54:46; 55:45; 56:44; 57:43; 58:42; 59:33; 60:40; 61:39; 62:38; 63:37; 64:36; 65:35; 66:34; 67:33; 68:32; 69:31; 70:30; 71:29; 72:28; 73:27; 74:26; 75:25; 76:24; 77:23; 78:22; 79:21; 80:29; 81:19; 82:18; 83:17; 84:16; 85:15; 86:14; 87:13; 88:12; 89:11; 90:10; 91:9; 92:8; 93:7; 94:6; 95:5; 96:4; 97:3; 98:2; 99:1.

According to one embodiment, at least one full round of propagation is effected in the presence of nicotinamide.

It will be appreciated that the culturing in the medium comprising nicotinamide may be effected prior or following the culturing in the medium devoid of nicotinamide.

According to embodiments of the present invention, the medium which is devoid of nicotinamide comprises FGF4 (either at the same or a different concentration as the medium which comprises nicotinamide).

According to other embodiments of the present invention, the medium which is devoid of nicotinamide is further devoid of FGF4.

Further, the present inventors contemplate more than one culturing stage in the presence of nicotinamide and FGF4 interspersed with culturing stages in the absence of the nicotinamide and vice versa.

According to one embodiment, the culturing in the presence of nicotinamide and FGF4 is effected for at least one day, at least two days, at least three days, at least four days, at least five days, at least six days, at least one week, at least two weeks, at least three weeks, at least four weeks or at least five weeks.

According to another embodiment, the culturing in the absence of nicotinamide is effected for at least one day, at least two days, at least three days, at least four days, at least five days, at least six days, at least one week, at least two weeks, at least three weeks, at least four weeks or at least five weeks.

The number of cells that may be cultured according to any of the methods of the present invention may be any number including small batches—e.g. $100 \times 10^4$ cells to larger batches—e.g. $100 \times 10^{12}$ or $100 \times 10^{13}$ cells.

When large batches are required, the cells are typically cultured in a bioreactor (or in multi-level industrial flasks), the size of which is selected according to the number of cells being cultured.

Examples of flasks and plates that may be used for growing MSCs in commercial quantities include for example Corning HYPERFlask™ Cell Culture Vessel, Corning CellSTACK™ Chambers, Corning HYPERStack™ Cell Culture Vessel, 40 stack chambers and NUNC Automatic Cell Factory Manipulator.

As used herein, the term "bioreactor" refers to any device in which biological and/or biochemical processes develop under monitored and controlled environmental and operating conditions, for example, pH, temperature, pressure, nutrient supply and waste removal. According to one embodiment of the invention, the basic classes of bioreactors suitable for use with the present invention include static bioreactors, stirred flask bioreactors, rotating wall bioreactors, hollow fiber bioreactors and direct perfusion bioreactors, as further described in WO 2005/007799, the contents of which are incorporated by reference.

The cultured population of cells generated using the methods described herein may be further treated following the culturing or stored (e.g. cryopreserved) in the presence of a cryopreservant. Such cryopreservants include dimethyl sulfoxide (DMSO), glycerol, and the like.

The cell populations generated following the culturing and/or the expansion method of the present invention may be used for a variety of purposes including research, for screening agents which affect the differentiation thereof and for therapeutic uses. Additionally, or alternatively, the cell populations may be stored (e.g. frozen) until required.

According to one embodiment, the mesenchymal stem cell populations generated using the methods disclosed herein may be used for further differentiation protocols.

Methods of differentiating mesenchymal stem cells towards various cell lineages are known in the art.

Differentiating cells may be obtained by culturing or differentiating MSC in a growth environment that enriches for cells with the desired phenotype, e.g. osteoblasts, adipocytes, etc. The culture may comprise agents that enhance differentiation to a specific lineage.

Osteogenic differentiation may be performed by plating cells and culturing to confluency, then culturing in medium comprising .beta.-glycerol phosphate, ascorbic acid and retinoic acid (see Cowan et al. (2005) Tissue engineering 11, 645-658).

To induce adipogenic differentiation detached cells may be reseeded in 24 well plates ($7 \times 10^4$ cells/ml) and treated with adipogenic medium for three weeks. Two exemplary adipogenic mediums are provided: DMEM supplemented with 0.05 mg/ml Gentamicin, 2 mM L-glutamine, 10% FBS, 0.5 µM 3-isobutyl-1-methylxanthine (IBMX, Sigma), 0.5 µM hydrocortisone (Sigma) and 60 µM indomethacin (Sigma), or MSC adipogenic stimulatory supplements purchased from StemCell Technologies, as per manufacturer's instructions. Adipogenic differentiation may be assessed by oil-red staining: cells are fixed with methanol at −20° C. for 10 minutes and treated with 60% isopropanol for 3 minutes. Plates may be stained in oil-red-O (Sigma) for 10 minutes and rinsed in tap water. After rinsing plates may be counterstained with Mayer hematoxylin (Sigma) for 1 minute and rinsed in tap water.

Myocyte differentiation may be performed by plating cells and culturing to confluency, then culturing in medium comprising horse serum, dexamethasone, and hydrocortisone (see Eun et al. (2004) Stem Cells 22:617-624); or 5-azacytidine (see Fukuda et al. (2001) Artificial Organs 25:187).

Chondrocyte differentiation may be performed by plating cells and culturing to confluency, then culturing in medium comprising dexamethasone, ascorbic acid 2-phosphate, insulin, transferrin, selenous acid, with or without TGF-$\beta_1$ (see Williams et al. (2003) Tissue Engineering 9(4):679).

Neuronal differentiation is known in the art. For example, generation of neurons and or oligodendrocytes from mesenchymal stem cells may be effected as described in U.S. Patent Publication Nos. 20100021434 and 20090257987.

Alternatively, or additionally, the mesenchymal stem cells may be genetically modified so as to express an agent (e.g. a polypeptide, siRNA or miRNA) that is useful for treating a disease or alternatively that drives its differentiation towards a certain lineage.

Thus, for example, the mesenchymal stem cells may be genetically modified to express bone morphogenic factor 2 (BMP2) in order to promote differentiation into bone.

Alternatively, the mesenchymal stem cells may be genetically modified to express Pd-x in order to promote differentiation into pancreatic cells.

Since mesenchymal stem cells are known to home and migrate towards wounds, the cells may be used as carriers, transporting useful molecules to the site of injury. The useful molecules may be molecules that are inherently found inside the mesenchymal stem cells (e.g. growth factors) or may be artificially placed inside the cells (i.e. proteins or polynucleotides transfected into the cells).

Both the differentiated and non-differentiated mesenchymal stem cell populations described herein may be used to treat a myriad of disorders, the particular disorders being selected according to the differentiation status of the cells.

Thus, according to another aspect of the present invention there is provided a method of treating a disease or disorder, the method comprising transplanting to a subject in need thereof a therapeutically effective amount of the isolated population of cells the present invention.

According to one embodiment, the disease or disorder is selected from the group consisting of a bone or cartilage disease, a neurodegenerative disease, a cardiac disease, a hepatic disease, cancer, nerve damage, wound healing, autoimmune disease, graft versus host disease, spinal cord injury and tissue regeneration.

Bone defects suitable for treatment using the cells of the present invention include, but are not limited to osteogenesis imperfecta, fracture, congenital bone defects, and the like.

Further, the mesenchymal stem cells of the present invention can be implanted in a subject to provide osseous and connective tissue support of orthopedic and other (e.g. dental) prosthetic devices, such as joint replacements and/or tooth implants.

The mesenchymal stem cells of the present invention can be used to treat CNS diseases.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, ALS, Multiple Sclerosis, Huntingdon's disease, autoimmune encephalomyelitis, diabetic neuropathy, glaucomatous neuropathy, macular degeneration, action tremors and tardive dyskinesia, panic, anxiety, depression, alcoholism, insomnia, manic behavior, Alzheimer's and epilepsy.

As mentioned, since MSCs can differentiate into cartilage, the mesenchymal stem cells of the present invention may be suitable for the treatment of joint conditions including, but not limited to osteoarthritis, rheumatoid arthritis, inflammatory arthritis, chondromalacia, avascular necrosis, traumatic arthritis and the like.

Bone marrow-derived mesenchymal stem cells (MSCs) are known to interact with hematopoietic stem cells (HSCs) and immune cells, and represent potential cellular therapy to enhance allogeneic hematopoietic engraftment and prevent graft-versus-host disease (GVHD). When hematopoietic stem cell numbers were limited, human engraftment of NOD-SCID mice was observed only after co-infusion of unrelated human MSCs, but not with co-infusion of mouse mesenchymal cell line. Unrelated human MSCs did not elicit T-cell activation in vitro and suppressed T-cell activation by Tuberculin and unrelated allogeneic lymphocytes in a dose-dependent manner. Cell-free MSC culture supernatant, mouse stromal cells and human dermal fibroblasts did not elicit this effect. These preclinical data suggest that unrelated, human bone marrow-derived, culture-expanded MSCs may improve the outcome of allogeneic transplantation by promoting hematopoietic engraftment and limiting GVHD (Maitra B, et al Bone Marrow Transplant. 2004 33(6):597-604).

It is known that when MSCs are introduced into the infarcted heart, they can prevent deleterious remodeling and improve recovery. MSCs have been injected directly into the infarct, or they have been administered intravenously and seen to home to the site of injury. Examination of the interaction of allogeneic MSCs with cells of the immune system indicates little rejection by T cells. Persistence of allogeneic MSCs in vivo suggests their potential "off the shelf" therapeutic use for multiple recipients (Pittenger M F, et al Circ Res. 2004 Jul. 9; 95(1):9-20).

The use of ex-vivo expanded mesenchymal cells for transplantation has the following advantages:

It reduces the volume of blood or other tissue required for reconstitution of a recipient adult tissue system.

It enables storage of small number of unexpanded mesenchymal cells, for example, form cord blood or peripheral blood, for potential future use.

In the case of autologous transplantation of recipients with malignancies, contaminating tumor cells in autologous infusion often contribute to the recurrence of the disease. Selecting and expanding mesenchymal cells will reduce the load of tumor cells in the final transplant.

Tissue regeneration: Mesenchymal cell populations of the present invention can be used for the promotion of tissue regeneration. Transplantation of mesenchymal stem cells has great promise for benefits in regenerative medicine, autoimmune diseases, inflammatory conditions, acute and chronic ischemic conditions reconstructive surgery, tissue engineering, regenerating new tissues and naturally healing diseased or injured organs.

Gene therapy: For successful long-term gene therapy, a high frequency of genetically modified cells with transgenes stably integrated within their genome is an obligatory requirement. Presently, gene transfer into fresh stem and/or progenitor cells is highly inefficient. The ability to store and process a selected population of mesenchymal cells ex-vivo, and enhance their homing and engraftment potential would provide for an increased probability of the successful use of genetically modified cell transplantation [Palmiter Proc Natl Acad Sci USA 91(4): 1219-1223, (1994)].

In any of the methods described herein the cells may be obtained from an autologous, semi-autologous or non-autologous (i.e., allogeneic or xenogeneic) human donor or embryo or cord/placenta. For example, cells may be isolated from a human cadaver or a donor subject.

The term semi-autologous refers to donor cells which are partially-mismatched to recipient cells at a major histocompatibility complex (MHC) class I or class II locus.

The cells of the present invention can be administered to the treated individual using a variety of transplantation approaches, the nature of which depends on the site of implantation.

According to one embodiment, the cells are not transplanted into the body in a medium comprising an agent selected from the group consisting of aryl hydrocarbone receptor antagonist, FGF4 and nicotinamide.

The cells may be transplanted to a damaged or healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

The term or phrase "transplantation", "cell replacement" or "grafting" are used interchangeably herein and refer to the introduction of the cells of the present invention to target tissue. As mentioned, the cells can be derived from the recipient or from an allogeneic, semi-allogeneic or xenogeneic donor. Other xeno-origins are also contemplated.

Cells of the present invention may be transplanted by means of direct injection into an organ, injection into the bloodstream, intraperitoneal injection, injection directly to lymphoid organs etc. Suitable methods of transplantation can be determined by monitoring the homing and engraftment of the implanted cells to the desired organ, the expression of desired organ-specific genes or markers, and the function of the derived organ of the subject. In the pancreas, for example, maintenance of euglycemia, secretion of insulin and/or C peptide can be a measure of the restoration of function to a diabetic host animal following cell replacement therapy as disclosed hereinbelow. In the liver, for example, albumin synthesis can be monitored.

MSCs typically down regulate MHC class 2 and are therefore less immunogenic. Embryonal or newborn cells obtained from the cord blood, cord's Warton's jelly or placenta are further less likely to be strongly immunogenic and therefore less likely to be rejected, especially since such cells are immunosuppressive and immunoregulatory to start with.

Notwithstanding, since non-autologous cells may induce an immune reaction when administered to the body several approaches may be taken to reduce the likelihood of rejection of non-autologous cells. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immunoisolating, semipermeable membranes before transplantation. Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnam-ylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylide-neacetate). J. Microencapsul. 2000, 17: 245-51.

For example, microcapsules are prepared by complexing modified collagen with a ter-polymer shell of 2-hydroxy-ethyl methylacrylate (HEMA), methacrylic acid (MAA) and methyl methacrylate (MMA), resulting in a capsule thickness of 2-5 .mu.m. Such microcapsules can be further encapsulated with additional 2-5 .mu.m ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 .mu.m (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Cell populations of the present invention can be provided per se, along with the culture medium containing same, isolated from the culture medium, and combined with a pharmaceutically acceptable carrier as well as with additional agents which may promote cell engraftment and/or organ function (e.g., immunosuppressing agents, antibiotics, growth factor). Hence, cell populations of the invention can be administered in a pharmaceutically acceptable carrier or diluent, such as sterile saline and aqueous buffer solutions. The use of such carriers and diluents is well known in the art.

Compositions of the present invention may, if desired, be presented in a pack or dispenser device, such as an FDA-approved kit, which may contain one or more unit dosage forms containing the active ingredient (e.g., cells). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The cells prepared according to the methods of the present invention can be administered to the subject per se, seeded on a scaffold and/or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein believed to be well known in the art and are provided for the convenience of the reader. All the information contained therein is incorporated herein by reference.

MATERIALS AND METHODS

Isolation—Human bone marrow derived mesenchymal cells were isolated based on their plastic adherence potential in expansion medium containing: High glucose DMEM and 10% Fetal Bovine Serum (FBS, Hyclone, Logan, Utah, USA), 0.05 mg/ml Gentamicin (Sigma) and 2 mM L-glutamine (Biological Industries, Israel). Cells were allowed to adhere for 3-4 days and non-adherent cells were washed out with medium changes.

Expansion—Mesenchymal stem cells were isolated using plastic adherence method, as described above and cultured for several passages in a medium which comprises fetal bovine serum in the presence or absence of SR1 for three passages (StemRegenin1, BioVision cat#1967-1).

Three concentrations 250, 1000 and 2500 nM of SR1 were examined.

The experimental groups were as follows:

Group 1: Control (Ctrl)

Group 2: 250 nM SR1

Group 3: 1000 nM SR1

Group 4: 2500 nM SR1

At about 80% confluence, adherent cells were collected following trypsin treatment, counted, characterized and re-seeded at a concentration of $1 \times 10^3$ cells/cm$^2$.

Measurement of CD45, CD105 and VCAM1/CD106: following Trypsin treatment the cells were analyzed for CD45, CD105 or CD106 expression in FACS using anti-human CD45 FITC, CD105 PE or CD106 APC antibodies.

Results

Figure 2:
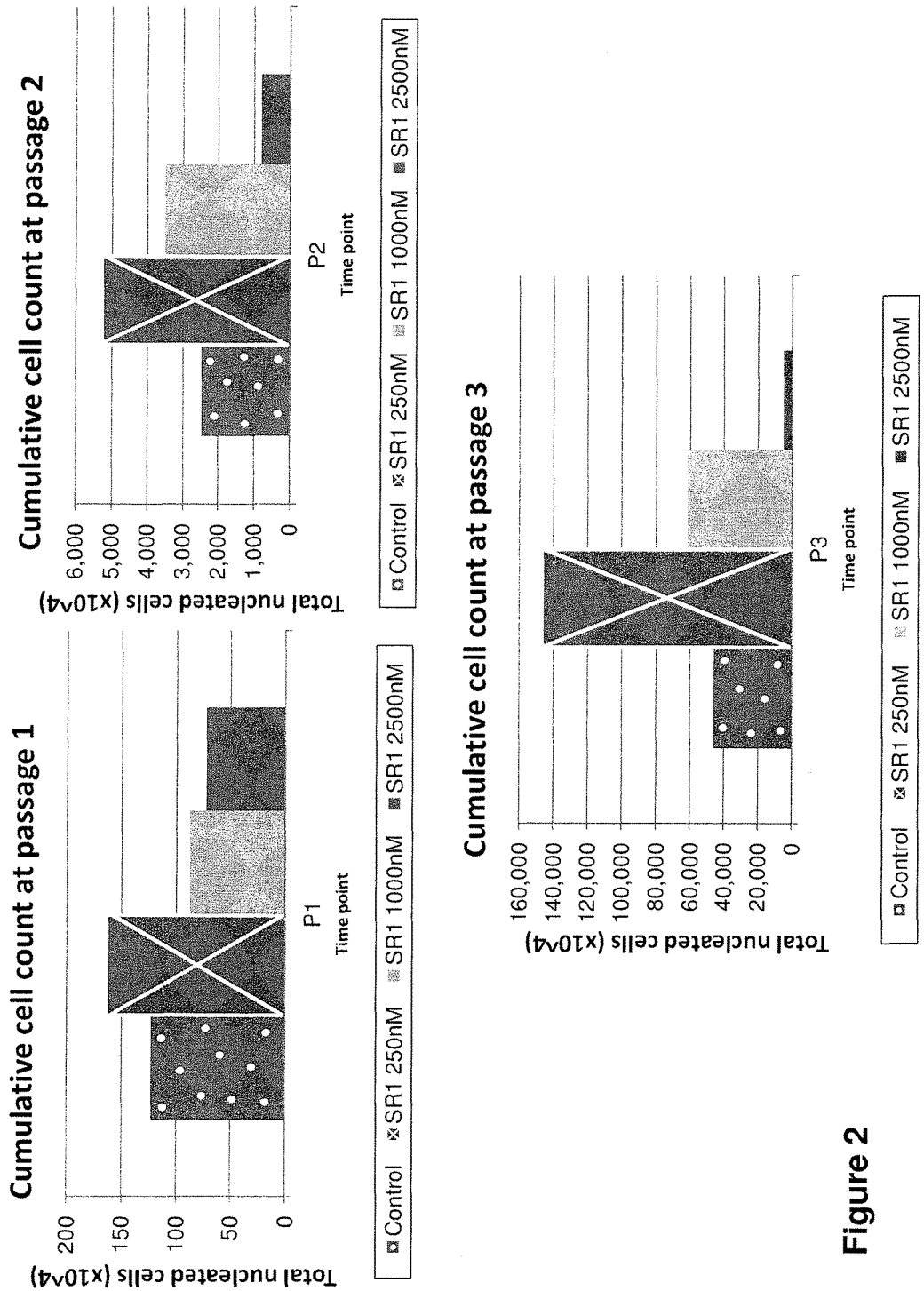
FIG. 2 is a bar graph showing cumulative count of mesenchymal stem cells in the absence or presence of SR1 at the indicated concentrations on the indicated passages.
Figure 3:
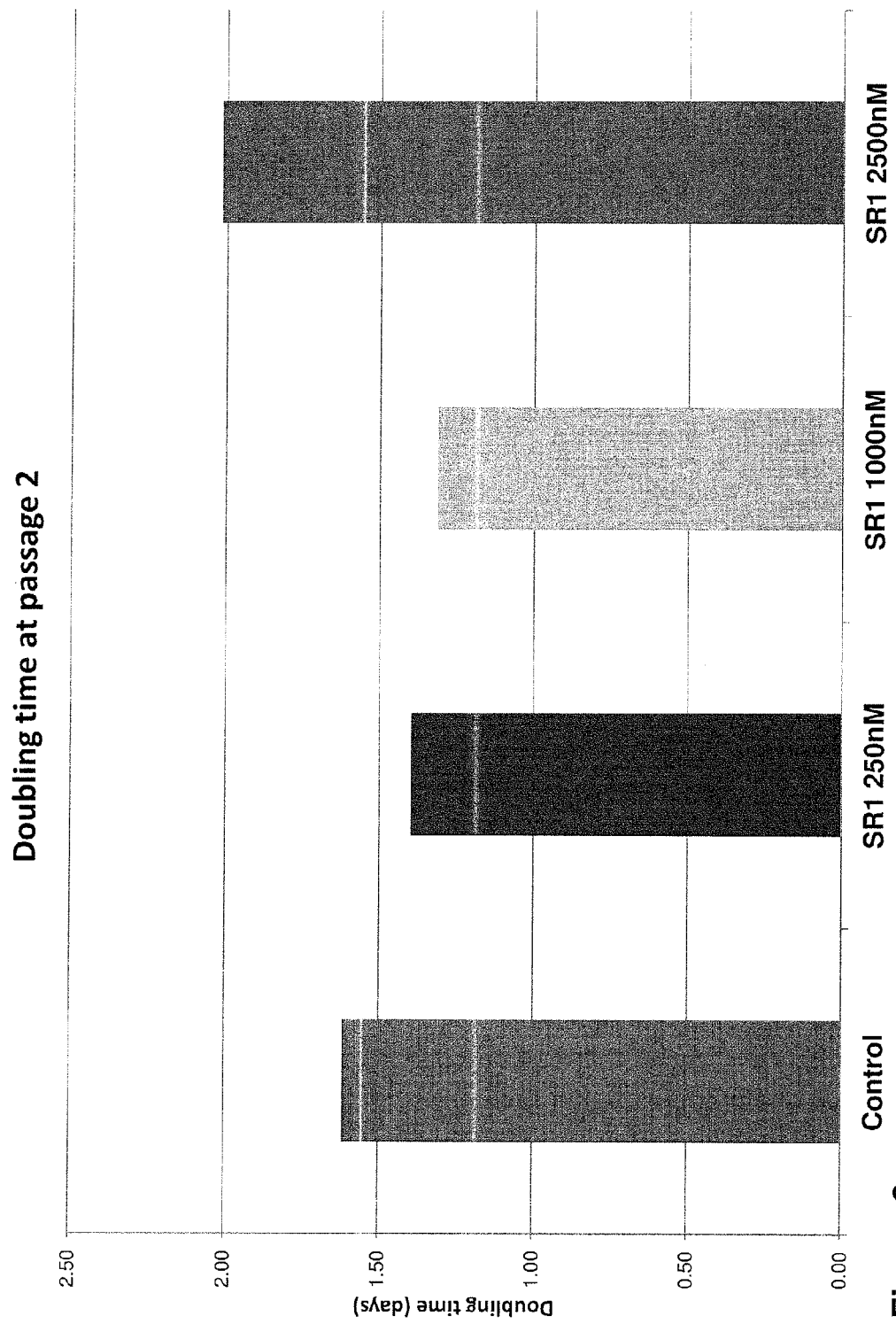
FIG. 3 is a bar graph showing doubling time of mesenchymal stem cells in the absence or presence of SR1 at passage 2.

FIGS. 1-3 illustrate that SR1 has a positive effect on the proliferation of mesenchymal stem cells. The most effective concentration was 250 nM.

Figure 4:
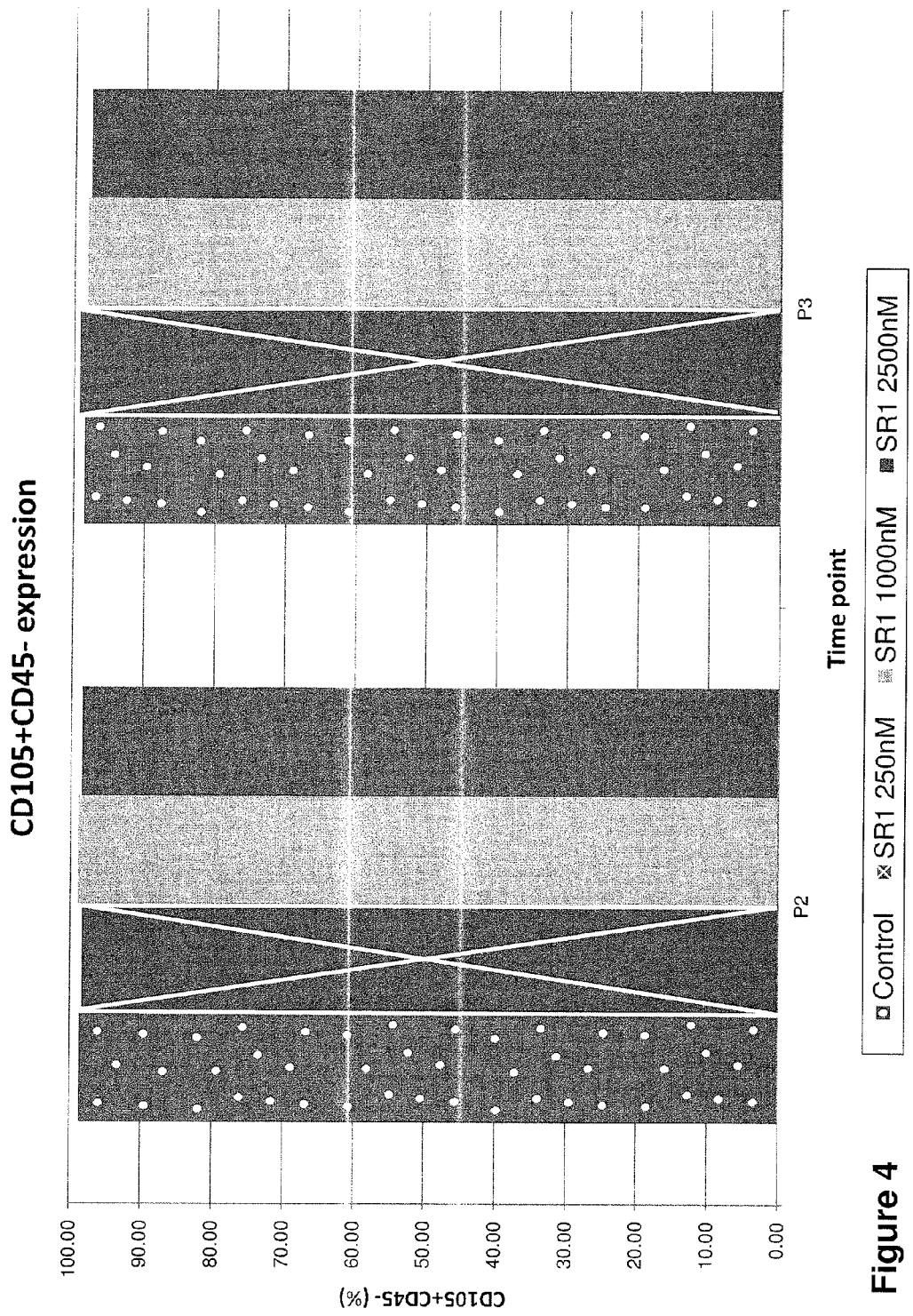
FIG. 4 is a bar graph showing percentage of CD105$^+$ CD45$^-$ cells in the absence or presence of SR1 at the indicated concentrations on the indicated passages.

FIG. 4 illustrates that mesenchymal stem cells grown in the presence of SR1 express the same CD45 and CD105 levels as mesenchymal stem cells grown in the absence of SR1 under identical conditions.

Figure 5:
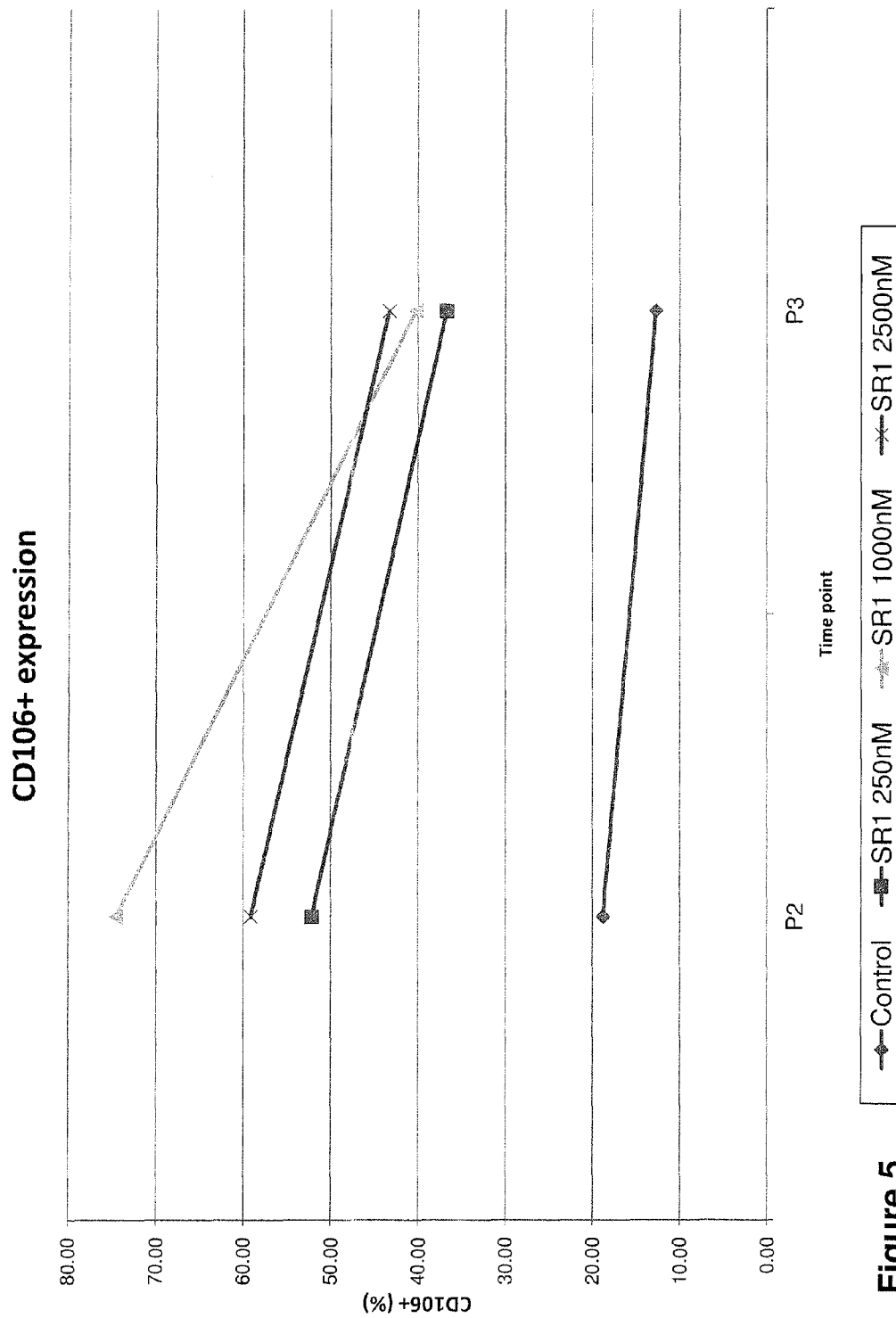
FIG. 5 is a bar graph showing percentage of CD106$^+$ cells in the absence or presence of SR1 at the indicated concentrations on the indicated passages.

FIG. 5 illustrates that mesenchymal stem cells grown in the presence of SR1 express more VCAM1/CD106 adhesion molecule than mesenchymal stem cells grown in the absence of SR1 under identical conditions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of culturing mesenchymal stem cells (MSCs) comprising culturing a population of the MSCs in a medium comprising an aryl hydrocarbon receptor antagonist, thereby culturing MSCs, wherein said aryl hydrocarbon receptor inhibitor comprises 4-(2-(2-(benzo[b]thiophen-3-yl)-9-isopropyl-9H-purin-6-ylamino) ethyl) phenol (StemReginin 1, SR1).

2. A method of expanding a population of mesenchymal stem cells, the method comprising culturing a seeded population of mesenchymal stem cells for a period of time sufficient for cell expansion, wherein said culturing is in a medium comprising an aryl hydrocarbon receptor antagonist, thereby generating an expanded population of mesenchymal stem cells, and wherein said aryl hydrocarbon receptor inhibitor comprises 4-(2-(2-(benzo[b]thiophen-3-yl)-9-isopropyl-9H-purin-6-ylamino) ethyl) phenol (StemReginin 1, SR1).

3. A method of generating cells useful for transplantation into a subject, the method comprising:
   (a) culturing mesenchymal stem cells according to the method of claim 1 to generate a population of cultured mesenchymal stem cells;
   (b) contacting said population of cultured mesenchymal stem cells with a differentiating agent, thereby generating cells useful for transplantation into a subject.

4. A method of generating cells useful for transplantation, the method comprising:
   (a) expanding mesenchymal stem cells according to the method of claim 2; and
   (b) contacting the mesenchymal stem cells with a differentiating agent, thereby generating cells useful for transplantation.

5. A cell culture, comprising mesenchymal stem cells and a medium which comprises an aryl hydrocarbon receptor antagonist, wherein said aryl hydrocarbon receptor inhibitor comprises 4-(2-(2-(benzo[b]thiophen-3-yl)-9-isopropyl-9H-purin-6-ylamino) ethyl) phenol (StemReginin 1, SR1).

6. The cell culture of claim 5, wherein said medium further comprises at least one of nicotinamide and a growth factor.

7. The method of claim 1, wherein the mesenchymal stem cells are derived from a tissue selected from the group consisting of bone marrow, adipose tissue, placenta and umbilical cord blood.

8. The method of claim 1, wherein the concentration of said SR1 in said medium is at a range of 100-1000 nM.

9. The method of claim 2, wherein the concentration of said SR1 in said medium is at a range of 100-1000 nM.

10. The method of claim 1, wherein said medium further comprises nicotinamide at a range of 1-20 mM.

11. The method of claim 10, wherein said medium further comprises FGF-4.

12. The method of claim 1, wherein a calcium concentration of said medium is greater than 1.8 mM.

13. The method of claim 1, wherein said culturing is effected on a plastic surface.

14. The method of claim 1, wherein said medium is devoid of platelet derived growth factor (PDGF).

15. The method of claim 2, wherein said expanding is effected under conditions that do not induce differentiation of said mesenchymal stem cells.

16. The method of claim 2, wherein said seeded population of mesenchymal stem cells were seeded in an absence of nicotinamide.

17. The method of claim 2, wherein said seeded population of mesenchymal stem cells were seeded in a presence of nicotinamide.

18. The method of claim 3, wherein said differentiation agent comprises a growth factor.

19. The cell culture of claim 5, wherein the concentration of said SR1 in said medium is at a range of 100-1000 nM.

* * * * *

UNITED STATES PATENT AND TRADEMARK OFFICE
CERTIFICATE OF CORRECTION

PATENT NO. : 9,567,569 B2
APPLICATION NO. : 13/946272
DATED : February 14, 2017
INVENTOR(S) : Tony Peled et al.

It is certified that error appears in the above-identified patent and that said Letters Patent is hereby corrected as shown below:

On the Title Page

Item (56) References Cited, Other Publications, Page 4, Column 2:
"Alter. "Fetal Erythropoiesis in Stress Hematopoiesis." Exp. Hematol. 7.55 (1979):200-209"
Should read:
-- Alter. "Fetal Erythropoiesis in Stress Hematopoiesis." Exp. Hematol. 7.S5 (1979):200-209 --

Item (56) References Cited, Other Publications, Page 5, Column 2:
"Burgada et al. "Synthesis of New Phosphonated Tripod Ligands as Putative New Therapeutic Agents in the Chelation Treatment of Metal Intoxications." Eur. J. Chem. (2001):349-352."
Should read:
-- Burgada et al. "Synthesis of New Phosphonated Tripod Ligands as Putative New Therapeutic Agents in the Chelation Treatment of Metal Intoxications." Eur. J.Org. Chem. (2001):349-352. --

Item (56) References Cited, Other Publications, Page 6, Column 1:
"Còtéet al. "Response to Histone Deacetylase Inhibition of Novel""
Should read:
-- Còté et al. "Response to Histone Deacetylase Inhibition of Novel --

Item (56) References Cited, Other Publications, Page 8, Column 2:
"Kawa et al. "Stem Cell Factor and/or Endothelin-3 Dependent Immortal Melanoblast and Melanocyte Populations Derived from Mouse Neural Crest Cells." Pigment Cell Res. 13.58(2000):73-80."
Should read:
-- Kawa et al. "Stem Cell Factor and/or Endothelin-3 Dependent Immortal Melanoblast and Melanocyte Populations Derived from Mouse Neural Crest Cells." Pigment Cell Res. 13.S8(2000):73-80. --

Signed and Sealed this
Twenty-eighth Day of November, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,567,569 B2

Item (56) References Cited, Other Publications, Page 8, Column 2:
"Khachigian. "DNAzymes: Cutting a Path to a New Class of Therapeutics." Curr. Opin. Mot Ther. 4.2(2002): 119-121."
Should read:
-- Khachigian. "DNAzymes: Cutting a Path to a New Class of Therapeutics." Curr. Opin. Mol Ther. 4.2(2002):119-121. --

Item (56) References Cited, Other Publications, Page 11, Column 1:
"Peled et al. "Copper Chelators Enable Long Term CFU and CD34'"
Should read:
-- Peled et al. "Copper Chelators Enable Long Term CFU and CD34$^+$ --

Item (56) References Cited, Other Publications, Page 12, Column 1:
"Roberts. "Mesenchymal Stem Cells." Vox Sanguinis. 87.S2(2004):S38-541."
Should read:
-- Roberts. "Mesenchymal Stem Cells." Vox Sanguinis. 87.S2(2004):S38-S41. --